United States Patent
Wickham et al.

(10) Patent No.: US 6,951,755 B2
(45) Date of Patent: *Oct. 4, 2005

(54) VECTORS AND METHODS FOR GENE TRANSFER

(75) Inventors: Thomas J. Wickham, Germantown, MD (US); Imre Kovesdi, Rockville, MD (US); Douglas E. Brough, Gaithersburg, MD (US)

(73) Assignee: GenVec, Inc., Gaithersburg, MD (US)

( * ) Notice: Subject to any disclaimer, the term of this patent is extended or adjusted under 35 U.S.C. 154(b) by 339 days.

This patent is subject to a terminal disclaimer.

(21) Appl. No.: 09/999,724

(22) Filed: Oct. 24, 2001

(65) Prior Publication Data

US 2003/0022355 A1 Jan. 30, 2003

Related U.S. Application Data

(63) Continuation of application No. 09/101,751, filed as application No. PCT/US96/19150 on Nov. 27, 1996, now Pat. No. 6,465,253, which is a continuation-in-part of application No. 08/563,368, filed on Nov. 28, 1995, now Pat. No. 5,965,541, and a continuation-in-part of application No. 08/701,124, filed on Aug. 21, 1996, now Pat. No. 5,846,782, and a continuation-in-part of application No. 08/700,846, filed on Aug. 21, 1996, now Pat. No. 5,962,311, which is a continuation-in-part of application No. 08/634,060, filed on Apr. 17, 1996, now Pat. No. 5,712,136, which is a continuation-in-part of application No. 08/303,162, filed on Sep. 8, 1994, now Pat. No. 5,559,099.

(51) Int. Cl.[7] .......................... C12N 15/861; C12N 7/01
(52) U.S. Cl. .................. 435/320.1; 435/235.1
(58) Field of Search ........................ 435/320.1, 235.1

(56) References Cited

U.S. PATENT DOCUMENTS

| 4,487,829 A | 12/1984 | Sharp et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |

(Continued)

FOREIGN PATENT DOCUMENTS

| EP | 0 259 212 A | 3/1988 |
| EP | 0 846 772 A | 6/1998 |
| JP | 2078631 A | 3/1990 |
| WO | WO 88/05077 A | 7/1988 |
| WO | WO 90/12087 A | 10/1990 |

(Continued)

OTHER PUBLICATIONS

Aggarwal et al., *Journal of Biological Chemistry*, 260(4), 2345–2354 (1985).

Albiges–Rizo et al., *Journal of Biological Chemistry*, 266, (6), 3961–3967 (1991).

Athappilly et al., *J. Mol. Biol.*, 242(4), 430–455 (1994).

Bai et al., *Journal of Virology*, 67(9), 5198–5205 (1993).

Ball–Goodrich et al., *Virology*, 184, 175–186 (1991).

(Continued)

Primary Examiner—Terry McKelvey
Assistant Examiner—Nancy Vogel
(74) Attorney, Agent, or Firm—Leydig, Voit & Mayer, Ltd.

(57) ABSTRACT

The present invention provides a recombinant adenovirus comprising coat proteins that lack native binding. In particular, the present invention provides a recombinant adenovirus comprising a penton base protein and a fiber protein, wherein the penton base protein and the fiber protein lack native binding. The present invention further provides a recombinant adenovirus comprising (a) a penton base protein that lacks native binding and (b) a nonnative amino acid sequence that binds a cell-surface binding site.

15 Claims, 30 Drawing Sheets

U.S. PATENT DOCUMENTS

| | | | |
|---|---|---|---|
| 4,792,525 A | 12/1988 | Ruoslahti et al. | |
| 4,797,368 A | 1/1989 | Carter et al. | |
| 4,956,281 A | 9/1990 | Wallner | |
| 5,024,939 A | 6/1991 | Gorman | |
| 5,096,815 A | 3/1992 | Ladner et al. | |
| 5,166,320 A | 11/1992 | Wu et al. | |
| 5,198,346 A | 3/1993 | Ladner et al. | |
| 5,204,445 A | 4/1993 | Plow et al. | |
| 5,223,394 A | 6/1993 | Wallner | |
| 5,223,409 A | 6/1993 | Ladner et al. | |
| 5,240,846 A | 8/1993 | Collins et al. | |
| 5,246,921 A | 9/1993 | Reddy et al. | |
| 5,332,567 A | 7/1994 | Goldenberg | |
| 5,349,053 A | 9/1994 | Landolfi | |
| 5,403,484 A | 4/1995 | Ladner et al. | |
| 5,436,146 A | 7/1995 | Shenk et al. | |
| 5,443,953 A | 8/1995 | Hansen et al. | |
| 5,474,935 A | 12/1995 | Chatterjee et al. | |
| 5,521,291 A | 5/1996 | Curiel et al. | |
| 5,534,423 A | 7/1996 | Palsson et al. | |
| 5,543,328 A | 8/1996 | McClelland et al. | |
| 5,547,932 A | 8/1996 | Curiel et al. | |
| 5,552,311 A | 9/1996 | Sorscher et al. | |
| 5,559,099 A * | 9/1996 | Wickham et al. | 514/44 |
| 5,571,698 A | 11/1996 | Ladner et al. | |
| 5,622,699 A | 4/1997 | Ruoshlahti et al. | |
| 5,661,133 A | 8/1997 | Leiden et al. | |
| 5,672,344 A | 9/1997 | Kelley et al. | |
| 5,674,722 A | 10/1997 | Mulligan et al. | |
| 5,693,509 A | 12/1997 | Cotton et al. | |
| 5,695,991 A | 12/1997 | Lindholm et al. | |
| 5,712,136 A * | 1/1998 | Wickham et al. | 435/456 |
| 5,731,190 A * | 3/1998 | Wickham et al. | 435/320.1 |
| 5,756,086 A | 5/1998 | McClelland et al. | |
| 5,770,442 A | 6/1998 | Wickham et al. | |
| 5,965,541 A * | 10/1999 | Wickham et al. | 514/44 |
| 6,465,253 B1 * | 10/2002 | Wickham et al. | 435/456 |

FOREIGN PATENT DOCUMENTS

| | | |
|---|---|---|
| WO | WO 91/00360 A | 1/1991 |
| WO | WO 91/05805 A | 5/1991 |
| WO | WO 91/05871 A | 5/1991 |
| WO | WO 92/02553 A | 2/1992 |
| WO | WO 92/06180 A | 4/1992 |
| WO | WO 92/13081 A | 8/1992 |
| WO | WO 93/03769 A | 3/1993 |
| WO | WO 93/06223 A | 4/1993 |
| WO | WO 93/07282 A | 4/1993 |
| WO | WO 93/07283 A | 4/1993 |
| WO | WO 93/25234 A | 12/1993 |
| WO | WO 94/06920 A | 3/1994 |
| WO | WO 94/08026 A | 4/1994 |
| WO | WO 94/10323 A | 5/1994 |
| WO | WO 94/11506 A | 5/1994 |
| WO | WO 94/15644 A | 7/1994 |
| WO | WO 94/17832 A | 8/1994 |
| WO | WO 94/24299 A | 10/1994 |
| WO | WO 94/26915 A | 11/1994 |
| WO | WO 95/05201 A | 2/1995 |
| WO | WO 95/06745 A | 3/1995 |
| WO | WO 95/14785 A | 6/1995 |
| WO | WO 95/16037 A | 6/1995 |
| WO | WO 95/21259 A | 8/1995 |
| WO | WO 95/26412 A | 10/1995 |
| WO | WO 95/27071 A | 10/1995 |
| WO | WO 95/31187 A | 11/1995 |
| WO | WO 95/31566 A | 11/1995 |
| WO | WO 96/00790 A | 1/1996 |
| WO | WO 96/07734 A | 3/1996 |
| WO | WO 96/07739 A | 3/1996 |
| WO | WO 96/10087 A | 4/1996 |
| WO | WO 96/13597 A | 5/1996 |
| WO | WO 96/14837 A | 5/1996 |
| WO | WO 96/17073 A | 6/1996 |
| WO | WO 96/18740 A | 6/1996 |
| WO | WO 96/26281 A | 8/1996 |
| WO | WO 97/20051 A | 6/1997 |
| WO | WO 97/24453 A | 7/1997 |
| WO | WO 97/38723 A | 10/1997 |
| WO | WO 98/07865 A | 2/1998 |
| WO | WO 98/11221 A | 3/1998 |
| WO | WO 98/13499 A | 4/1998 |
| WO | WO 98/22609 A | 5/1998 |
| WO | WO 98/32842 A | 7/1998 |
| WO | WO 98/40509 A | 9/1998 |

OTHER PUBLICATIONS

Barinaga et al., *Science*, 266, p. 1326 (Nov. 25, 1994).
Batra et al., *Gene Therapy*, 1, 255–260 (1994).
Boursnell et al., *Gene*, 13, 311–317 (1981).
Caillet–Boudin et al., *Journal of Molecular Biology*, 217, 477–486 (1991).
Chroboczek et al., *Virology*, 186, 280–285 (1992).
Chu et al., *Gene Therapy*, 1, 292–299 (1994).
Cotten et al., *Proc. Natl. Acad. Sci. USA*, 87, 4033–4037 (1990).
Cotten et al., *Proc. Natl. Acad. Sci. USA*, 89, 6094–6098 (1992).
Crawford–Miksza et al., *Journal of Virology*, 70 (3), 1836–1844 (1996).
Crompton et al., *Journal of General Virology*, 75 (1), 133–139 (1994).
Crystal, *Science*, 270, 404–410 (Oct. 20, 1995).
Curiel et al., *Human Gene Therapy*, 3, 147–154 (1992).
Curiel et al., *Proc. Natl. Acad. Sci. USA*, 88, 8850–8854 (1991).
Defer et al., *Journal of Virology*, 64(8), 3661–3673 (1990).
Dupuit et al., *Human Gene Therapy*, 6, 1185–1193 (1995).
Etienne–Julan et al., *Journal of General Virology*, 73, 3251–3255 (1992).
Falck–Pedersen, Abstract of National Institutes of Health Grant Application No. 1 PO1 HL51746–01UB:0004 entitled "Gene Therapy For Cystic Fibrosis" (1994).
Falgout et al., *Journal of Virology*, 62 (2), 622–625 (1988).
Gall et al., *Journal of Virology*, 70, 2116–2123 (1996).
Goeddel et al., *Cold Spring Harbor Symposia on Quantitative Biology*, 51 (1986).
Greber et al., *Cell*, 75, 477–486 (1993).
Green et al., *EMBO Journal*, 2 (8), 1357–1365 (1983).
Grubb et al., *Nature*, 371, 802–806 (1994).
Han et al., *Proc. Natl. Acad. Sci. USA*, 92, 9747–9751 (1995).
Henry et al., *Journal of Virology* 68 (8), 5239–5246 (1994).
Hong et al., *Virology*, 185 (2), 758–767 (1991).
Horvath et al., *Journal of Virology*, 62 (1), 341–345 (1988).
Huang et al., *Journal of Virology*, 69 (4), 2257–2263 (1995).
Javier et al., *Science*, 257, 1267–1271 (Aug. 28, 1992).
Jolly, *Cancer Gene Therapy*, 1 (1), 51–64 (1994).
Karayan et al., *Virology*, 202, 782–785 (1994).
Kass–Eisler et al., *Proc. Natl Acad. Sci. USA*, 90, 11498–11502 (1993).
Kinloch et al., *Journal of Biological Chemistry*, 259 (10), 6431–6436 (1984).
Komoriya et al., *Journal of Biological Chemistry*, 266 (23), 15075–15079 (1991).

Maraveyas et al., *Acta Oncologica*, 32 (7/8), 741–746 (1993).
Marshall, *Science*, 269, 1050–1055 (Aug. 25, 1995).
Mastrangeli et al., *Human Gene Therapy*, 7, 79–87 (1996).
Mastrangeli et al., *Ped. Pulm. Suppl.*, 12, 230, Abst. No. 180 (1995).
Mathias et al., *Journal of Virology*, 68 (10), 6811–6814 (1994).
Michael et al., *Adenovirus Workshop: St. Andrews University*, 52, 13–15 (1995).
Michael et al., *Gene Therapy*, 2 (9), 660–668 (Nov. 1995).
Michael et al., *Journal of Biological Chemistry*, 268 (10), 686–6869 (1993).
Miller et al., *FASEB Journal*, 9, 190–199 (1995).
Neda et al., *Journal of Biological Chemistry*, 266 (22), 14143–14146 (1991).
Nemerow et al., in *Biology of Vitronectins and Their Receptors* (Preissner et al., eds), 177–184 (Elsevier Science Publishers, 1993).
Nemerow et al., *Trends in Cell Biology*, 4, 52–55 (1994).
Novelli et al., *Virology*, 185, 365–376 (1991).
Orkin et al., *Report and Recommendations to the Panel to Assess NIH Investment in Research on Gene Therapy* (1995).
Peteranderl et al., *Biochemistry*, 31, 12272–12276 (1992).
Roberts et al., *Science*, 232, 1148–1151 (1986).
Russell et al., *Nucleic Acids Research*, 21 (5), 1081–1085 (1993).
Signas et al., *Journal of Virology*, 53 (2), 672–678 (1985).
Silver et al., *Virology*, 165, 377–387 (1988).
Stewart et al., *EMBO Journal*, 12 (7), 2589–2599 (1993).
Toogood et al., *Journal of General Virology*, 73, 1429–1435 (1992).
Wagner et al., *Proc. Natl. Acad. Sci. USA*, 89, 6099–6103 (1992).
Watkins et al., presented at *Keystone Symposium on Molecular and Cellular Biology*, Abst. No. 336 (Taos, New Mexico (US), Feb. 22–28, 1996).
Watson et al., *Journal of Virology*, 69, 525–535 (1988).
Wickham et al., *Cell*, 73, 309–319 (1993).
Wickham et al., *Gene Therapy*, 2, 750–756 (1995).
Wickham et al., *Journal of Cell Biology*, 127 (1), 257–264 (1994).
Wickham et al., *Journal of Virology*, 70, 6831–6838 (1996).
Xia et al., *Structure*, 2, 1259–1270 (1994).
Hong et al., *Tumor Virus Meeting on SV40, Polyoma, and Adenoviruses*, Aug. 15–19, 1990, Cold Spring Harbor, NY, p. 146 (1990).

* cited by examiner

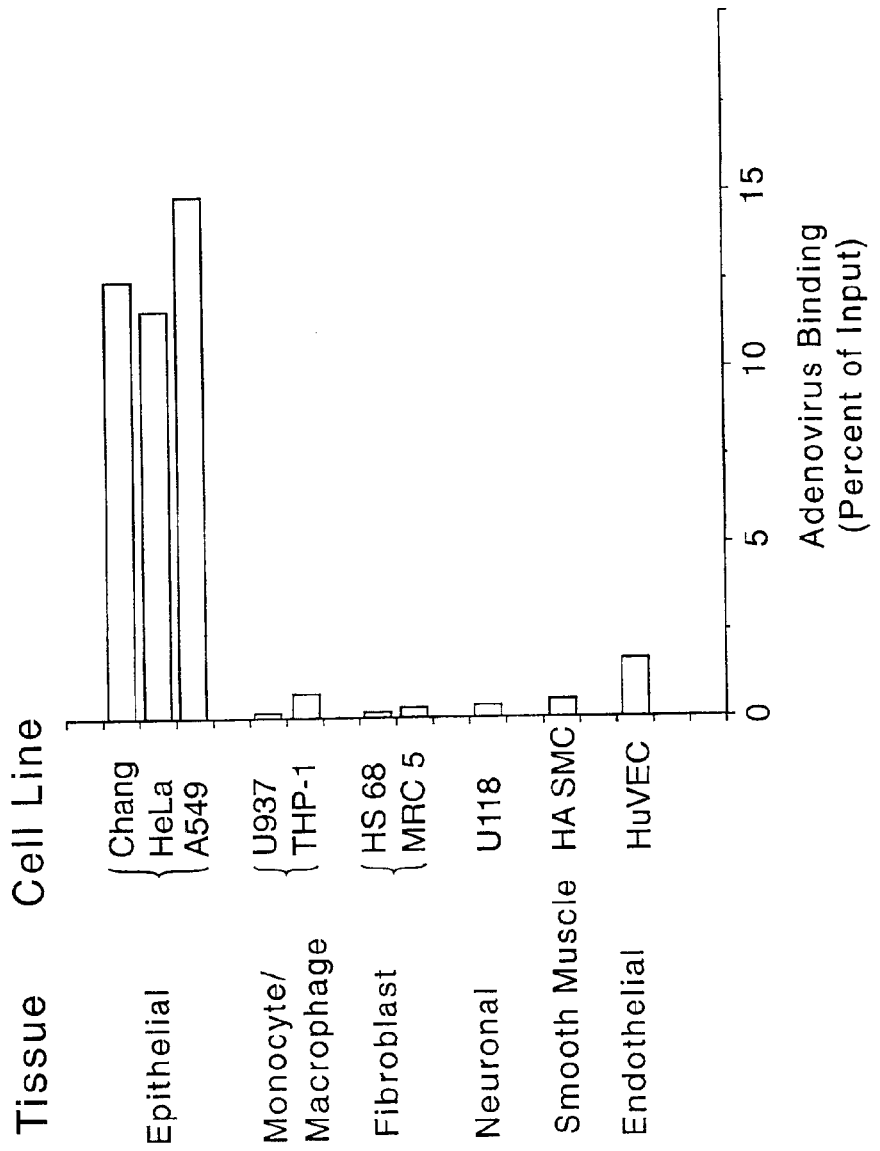

Ala Gln Glu *
GCC CAA GAA TAA AGA ATC GTT TGT GTT ATG TTT CAA CGT    [SEQ ID NO:13]

TRANSCRIPTION

GCC CAA GAA UAA AGA AUC GUU UGU GUU AUG UUU CAA AAA AAA AAA AAA AAA ..... [SEQ ID NO:14]

TRANSLATION

Ala Gln Glu *

FIG. 2A

Ala Gln Glu Gly Ser Asn Lys Glu Ser Phe Val Leu Cys [SEQ ID NO:16]

GCC CAA GAA GGA TCC AAT AAA GAA TCG TTT GTG TTA TGT [SEQ ID NO:15]
              BamHI    PolyA

TRANSCRIPTION

GCC CAA GAA GGA UCC AAU AAA GAA UCG UUU GUG UUA AAA AAA AAA AAA AAA AAA... [SEQ ID NO:17]

TRANSLATION

Ala Gln Glu Gly Ser Asn Lys Glu Ser Phe Val Leu Lys Lys Lys Lys Lys... [SEQ ID NO:18]

FIG. 2B

TAT GGA GGA TCC AAT AAA GAA TCG TTT GTG TTA TGT TTC AAC GTG TTT ATT TTT C [SEQ ID NO:9]
Ndel   BamHI   PolyA                                    polyA     MunI

FIG. 4A

AAT TGA AAA ATA AAC ACG TTG AAA CAT AAC ACA AAC GAT TCT TTA TTG GAT CCT CCA [SEQ ID NO:10]
MunI   PolyA                                              BamHI   Ndel

FIG. 4B

TCCC CCCGGG TCTAGA TTA GGA TCC TCC TTG GGC AAT GTA TGA [SEQ ID NO:11]
     XmaI   XbaI         BamHI

FIG. 4C

CGT GTA TCC ATA TGA CAC AGA [SEQ ID NO:12]
             Ndel

FIG. 4D

WT UTV 62 kD →  ▬  ▬

FIG. 5

GGATCAGGATCAGGTTCAGGGAGTGGCTCTAAAAAGAAGAAAAGAAGAAGTAA    [SEQ ID NO:21]
GlySerGlySerGlySerGlySerGlySerLysLysLysLysLysLysLys      [SEQ ID NO:22]

pBSS75-100ΔE3 pGS (null) (9972)

```
          BamHI                                           SpeI
GCCCAAGAAGGATCCGGTTCAGGATCTGGCAGTGGCTGACTAGTTAA    [SEQ ID NO:23]
AlaGlnGluGlySerGlySerGlySerGlySerThrSer            [SEQ ID NO:24]
```

BamHI

GCCCAAGAAGGATCCGGTTCAGGATCTGGCAGTGGCTCGACTAGAAAGAAGAACGCAAAAAGAAGACTAGTTAA [SEQ ID NO:25]
AlaGlnGluGlySerGlySerGlySerGlySerGlySerThrArgLysLysLysArgLysLysLysThrSer [SEQ ID NO:26]

Spel

BamHI
GCCCAAGAAGGATCCGGTTCAGGATCTGGCTCAGTGGCTCGACTAGAAAGAAGAAGCCAAAAAAAAGAAGAAGACTAGTTAA [SEQ ID NO:27]
AlaGlnGluGlySerGlySerGlySerGlySerGlySerGlySerThrArgLysLysLysArgLysLysLysArgLysLysLysThrSer [SEQ ID NO:28]
                                                                                    SpeI

SpeI
ATTACACTTAATGGCACTAGTGAATCCACAGAAACT [SEQ ID NO:29]
IleThrLeuAsnGlyThrSerGluSerThrGluThr [SEQ ID NO:30]

ATTACACTTAATGGCACTAGAAAAGAAGAAACGCAAAAGAAGAAGACTAGTGAATCCACAGAAACT [SEQ ID NO:31]
IleThrLeuAsnGlyThrArgLysLysArgLysLysLysThrSerGluSerThrGluThr [SEQ ID NO:32]
                 SpeI                                   SpeI

SpeI [SEQ ID NO:33]
[SEQ ID NO:34]

CTTAATGGCACTAGAAAGAAGAAGCGCAAAAAAAAAAGAAGAAGAAGACTAGTGAATCCACA
LeuAsnGlyThrArgLysLysLysArgLysLysLysLysLysLysArgLysLysLysThrSerGluSerThr

XbaI
ACCGCATCTAGAGGTGATAACTTG   [SEQ ID NO:39]
ThrAlaSerArgGlyAspAsnLeu   [SEQ ID NO:40]

XbaI        Ppu10I          SpeI        Ppu10I          XbaI
TCTAGAGCAGCTATGCATGAAGGACTAGTGGAGAGATGCATGCAGCCTCTAGA  [SEQ ID NO:43]
 SerArgAlaAlaMetHisGluGlyThrSerGlyGluMetHisAlaAlaSerArg [SEQ ID NO:44]

XbaI                 ⓙ
TCT AGA GCA GCT ATG CAG GCG GCC GCA GAA GCT GAA GAG GCA GCC
Ser Arg Ala Ala Met Gln Ala Ala Ala Glu Ala Glu Glu Ala Ala
ACA CGG GCT GAG GAG AAG CGC GCT GAG GCC GAA GCA GCG GCC GAA
Thr Arg Ala Glu Glu Lys Arg Ala Glu Ala Glu Ala Ala Ala Glu
GCT GCC GCC CCC GCT GCC CAA CCC GAG GTC GAG AAG CCT CAG AAG
Ala Ala Ala Pro Ala Ala Gln Pro Glu Val Glu Lys Pro Gln Lys
AAA CAG GCT AAC GCT AAG GCC GAA GCT GTG CAG GCG GCC GCA GAA
Lys Gln Ala Asn Ala Lys Ala Glu Ala Val Gln Ala Ala Ala Glu
GCT GAA GAG GCA GCC ACA CGG GCT GAG GAG AAG CGC GCT GAG GCC
Ala Glu Glu Ala Ala Thr Arg Ala Glu Glu Lys Arg Ala Glu Ala
GAA GCA GCG GCC GAA GCT GCC GCC CCC GCT GCG CAA CCC GAG GTC
Glu Ala Ala Ala Glu Ala Ala Ala Pro Ala Ala Gln Pro Glu Val
                                                          ⓙ
GAG AAG CCT CAG AAG AAA CAG GCT AAC GCT AAG GCC GAA GCT GTG
Glu Lys Pro Gln Lys Lys Gln Ala Asn Ala Lys Ala Glu Ala Val
         SpeI       ⓙ
CAT GAA GGG ACT AGT GGA GAG ATG CAG GCG GCC GCA GAA GCT GAA
His Glu Gly Thr Ser Gly Glu Met Gln Ala Ala Ala Glu Ala Glu
GAG GCA GCC ACA CGG GCT GAG GAG AAG CGC GCT GAG GCC GAA GCA
Glu Ala Ala Thr Arg Ala Glu Glu Lys Arg Ala Glu Ala Glu Ala
GCG GCC GAA GCT GCC GCC CCC GCT GCG CAA CCC GAG GTC GAG AAG
Ala Ala Glu Ala Ala Ala Pro Ala Ala Gln Pro Glu Val Glu Lys
CCT CAG AAG AAA CAG GCT AAC GCT AAG GCC GAA GCT GTG CAG GCG
Pro Gln Lys Lys Gln Ala Asn Ala Lys Ala Glu Ala Val Gln Ala
GCC GCA GAA GCT GAA GAG GCA GCC ACA CGG GCT GAC GAG AAG CGC
Ala Ala Glu Ala Glu Glu Ala Ala Thr Arg Ala Glu Glu Lys Arg
GCT GAG GCC GAA GCA GCG GCC GAA GCT GCC GCC CCC GCT GCG CAA
Ala Glu Ala Glu Ala Ala Ala Glu Ala Ala Ala Pro Ala Ala Gln
CCC GAG GTC GAG AAG CCT CAG AAG AAA CAG GCT AAC GCT AAG GCC
Pro Glu Val Glu Lys Pro Gln Lys Lys Gln Ala Asn Ala Lys Ala
         ⓙ               XbaI
GAA GCT GTG CAT GCA GCC TCT AGA     [SEQ ID NO:47]
Glu Ala Val His Ala Ala Ser Arg     [SEQ ID NO:48]

FIG. 27 Cont.

SEQUENCE LISTING

```
<160> NUMBER OF SEQ ID NOS: 94

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Lys Lys Lys Lys Lys Lys Lys Lys
 1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Arg Arg Arg Arg Arg Arg Arg Arg
 1               5
```

```
<210> SEQ ID NO 3
<211> LENGTH: 8
<212> TYPE: PRT
<213> ORGANISM: Artificial Sequence
<220> FEATURE:
<223> OTHER INFORMATION: Synthetic
<221> NAME/KEY: misc_feature
<222> LOCATION: (1)..(8)
<223> OTHER INFORMATION: "Xaa" is "Lys" or "Arg"

<400> SEQUENCE: 3

Xaa Xaa Xaa Xaa Xaa Xaa Xaa Xaa
  1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Gly Ser Asn Lys Glu Ser Phe Val Leu Lys Lys Lys Lys Lys Lys
  1               5                  10                  15

<210> SEQ ID NO 5
<211> LENGTH: 18
<212> TYPE: PRT
<213> ORGANISM: Artificial Sequence
<220> FEATURE:
<223> OTHER INFORMATION: Synthetic

<400> SEQUENCE: 5

Ala Gly Ser Asn Lys Asn Lys Glu Ser Phe Val Leu Lys Lys Lys
  1               5                  10                  15

Lys Lys

<210> SEQ ID NO 6
<211> LENGTH: 8
<212> TYPE: DNA
<213> ORGANISM: Artificial Sequence
<220> FEATURE:
<223> OTHER INFORMATION: Synthetic

<400> SEQUENCE: 6 ggatccaa                                                              8

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
ggatccaata aagaatcgtt tgtgttatgt                                     30

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
gccggatcca acaagaataa agaatcgttt gtgtta                              36
```

```
<210> SEQ ID NO 9
<211> LENGTH: 55
<212> TYPE: DNA
<213> ORGANISM: Artificial Sequence
<220> FEATURE:
<223> OTHER INFORMATION: Synthetic

<400> SEQUENCE: 9
tatggaggat ccaataaaga atcgtttgtg ttatgtttca acgtgtttat ttttc          55

<210> SEQ ID NO 10
<211> LENGTH: 57
<212> TYPE: DNA
<213> ORGANISM: Artificial Sequence
<220> FEATURE:
<223> OTHER INFORMATION: Synthetic

<400> SEQUENCE: 10
aattgaaaaa taaacacgtt gaaacataac acaaacgatt ctttattgga tcctcca       57

<210> SEQ ID NO 11
<211> LENGTH: 43
<212> TYPE: DNA
<213> ORGANISM: Artificial Sequence
<220> FEATURE:
<223> OTHER INFORMATION: Synthetic

<400> SEQUENCE: 11
tcccccgggg tctagattag gatccttctt gggcaatgta tga                       43

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
cgtgtatcca tatgacacag a                                               21

<210> SEQ ID NO 13
<211> LENGTH: 39
<212> TYPE: DNA
<213> ORGANISM: Artificial Sequence
<220> FEATURE:
<223> OTHER INFORMATION: Synthetic

<400> SEQUENCE: 13
gcccaagaat aaagaatcgt tgtgttatg tttcaacgt                             39

<210> SEQ ID NO 14
<211> LENGTH: 48
<212> TYPE: RNA
<213> ORGANISM: Artificial Sequence
<220> FEATURE:
<223> OTHER INFORMATION: Synthetic

<400> SEQUENCE: 14
gcccaagaau aaagaaucgu uuguguuaaa aaaaaaaaa aaaaaaaa                   48

<210> SEQ ID NO 15
<211> LENGTH: 39
<212> TYPE: DNA
<213> ORGANISM: Artificial Sequence
```

```
<220> FEATURE:
<223> OTHER INFORMATION: Synthetic
<221> NAME/KEY: CDS
<222> LOCATION: (1)..(39)

<400> SEQUENCE: 15 gcc caa gaa gga tcc aat aaa gaa tcg ttt gtg tta tgt          39
Ala Gln Glu Gly Ser Asn Lys Glu Ser Phe Val Leu Cys
 1               5                  10

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16

Ala Gln Glu Gly Ser Asn Lys Glu Ser Phe Val Leu Cys
 1               5                  10

<210> SEQ ID NO 17
<211> LENGTH: 51
<212> TYPE: RNA
<213> ORGANISM: Artificial Sequence
<220> FEATURE:
<223> OTHER INFORMATION: Synthetic
<221> NAME/KEY: CDS
<222> LOCATION: (1)..(51)

<400> SEQUENCE: 17 gcc cca gaa gaa ucc aau aaa gaa ucg uuu gug uua aaa aaa aaa          48
Ala Pro Glu Glu Ser Asn Lys Glu Ser Phe Val Leu Lys Lys Lys
 1               5                  10                  15 aaa                                                                  51
Lys

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Ala Pro Glu Glu Ser Asn Lys Glu Ser Phe Val Leu Lys Lys Lys Lys
 1               5                  10                  15

Lys

<210> SEQ ID NO 19
<211> LENGTH: 24
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(24)

<400> SEQUENCE: 19 tca tac att gcc caa gaa gaa tcc                              24
Ser Tyr Ile Ala Gln Glu Glu Ser
 1               5

<210> SEQ ID NO 20
<211> LENGTH: 8
<212> TYPE: PRT
<213> ORGANISM: Artificial Sequence
```

-continued

<220> FEATURE:
<223> OTHER INFORMATION: Synthetic

<400> SEQUENCE: 20

Ser Tyr Ile Ala Gln Glu Glu Ser
 1               5

<210> SEQ ID NO 21
<211> LENGTH: 54
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(54)

<400> SEQUENCE: 21 gga tca gga tca ggt tca ggg agt ggc tct aaa aag aag aaa aag aag     48
Gly Ser Gly Ser Gly Ser Gly Ser Gly Ser Lys Lys Lys Lys Lys Lys
 1               5                  10                  15 aag taa                                                              54
Lys

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Gly Ser Gly Ser Gly Ser Gly Ser Gly Ser Lys Lys Lys Lys Lys Lys
 1               5                  10                  15

Lys

<210> SEQ ID NO 23
<211> LENGTH: 48
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(48)

<400> SEQUENCE: 23 gcc caa gaa gga tcc ggt tca gga tct ggc agt ggc tcg act agt taa     48
Ala Gln Glu Gly Ser Gly Ser Gly Ser Gly Ser Gly Ser Thr Ser
 1               5                  10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Ala Gln Glu Gly Ser Gly Ser Gly Ser Gly Ser Gly Ser Thr Ser
 1               5                  10                  15

<210> SEQ ID NO 25
<211> LENGTH: 75
<212> TYPE: DNA
<213> ORGANISM: Artificial Sequence

```
<220> FEATURE:
<223> OTHER INFORMATION: Synthetic
<221> NAME/KEY: CDS
<222> LOCATION: (1)..(75)

<400> SEQUENCE: 25 gcc caa gaa gga tcc ggt tca gga tct ggc agt ggc tcg act aga aag      48
Ala Gln Glu Gly Ser Gly Ser Gly Ser Gly Ser Thr Arg Lys
 1               5                  10                  15 aag aaa cgc aaa aag aag act agt taa                                  75
Lys Lys Arg Lys Lys Lys Thr Ser
            20

<210> SEQ ID NO 26
<211> LENGTH: 24
<212> TYPE: PRT
<213> ORGANISM: Artificial Sequence
<220> FEATURE:
<223> OTHER INFORMATION: Synthetic

<400> SEQUENCE: 26

Ala Gln Glu Gly Ser Gly Ser Gly Ser Gly Ser Thr Arg Lys
 1               5                  10                  15

Lys Lys Arg Lys Lys Lys Thr Ser
            20

<210> SEQ ID NO 27
<211> LENGTH: 86
<212> TYPE: DNA
<213> ORGANISM: Artificial Sequence
<220> FEATURE:
<223> OTHER INFORMATION: Synthetic

<400> SEQUENCE: 27
gcccaagaag gatccggttc aggatctggc agtggctcga ctagaaagaa gaagcgcaaa    60 aaaaagaaa gaagaagact agttaa                                          86

<210> SEQ ID NO 28
<211> LENGTH: 28
<212> TYPE: PRT
<213> ORGANISM: Artificial Sequence
<220> FEATURE:
<223> OTHER INFORMATION: Synthetic

<400> SEQUENCE: 28

Ala Gln Glu Gly Ser Gly Ser Gly Ser Gly Ser Thr Arg Lys
 1               5                  10                  15

Lys Lys Arg Lys Lys Arg Lys Lys Lys Thr Ser
            20                  25

<210> SEQ ID NO 29
<211> LENGTH: 36
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(36)

<400> SEQUENCE: 29 att aca ctt aat ggc act agt gaa tcc aca gaa act                      36
Ile Thr Leu Asn Gly Thr Ser Glu Ser Thr Glu Thr
 1               5                  10
```

<210> SEQ ID NO 30
<211> LENGTH: 12
<212> TYPE: PRT
<213> ORGANISM: Artificial Sequence
<220> FEATURE:
<223> OTHER INFORMATION: Synthetic

<400> SEQUENCE: 30

Ile Thr Leu Asn Gly Thr Ser Glu Ser Thr Glu Thr
1               5                   10

<210> SEQ ID NO 31
<211> LENGTH: 63
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(63)

<400> SEQUENCE: 31 att aca ctt aat ggc act aga aag aag aaa cgc aaa aag aag act agt     48
Ile Thr Leu Asn Gly Thr Arg Lys Lys Lys Arg Lys Lys Lys Thr Ser
1               5                   10                  15 gaa tcc aca gaa act                                                 63
Glu Ser Thr Glu Thr
            20

<210> SEQ ID NO 32
<211> LENGTH: 21
<212> TYPE: PRT
<213> ORGANISM: Artificial Sequence
<220> FEATURE:
<223> OTHER INFORMATION: Synthetic

<400> SEQUENCE: 32

Ile Thr Leu Asn Gly Thr Arg Lys Lys Lys Arg Lys Lys Lys Thr Ser
1               5                   10                  15

Glu Ser Thr Glu Thr
            20

<210> SEQ ID NO 33
<211> LENGTH: 60
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(60)

<400> SEQUENCE: 33 ctt aat ggc act aga aag aag aag cgc aaa aaa aaa aga aag aag act     48
Leu Asn Gly Thr Arg Lys Lys Lys Arg Lys Lys Lys Arg Lys Lys Thr
1               5                   10                  15 agt gaa tcc aca                                                     60
Ser Glu Ser Thr
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic

```
<400> SEQUENCE: 34

Leu Asn Gly Thr Arg Lys Lys Lys Arg Lys Lys Arg Lys Lys Thr
 1               5                  10                  15

Ser Glu Ser Thr
            20

<210> SEQ ID NO 35
<211> LENGTH: 57
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(57)

<400> SEQUENCE: 35 aac gat act aga aag aag aag cgc aaa aaa aaa aga aag aag aag act      48
Asn Asp Thr Arg Lys Lys Lys Arg Lys Lys Lys Arg Lys Lys Lys Thr
 1               5                  10                  15 agt gcc aca                                                          57
Ser Ala Thr <210> SEQ ID NO 36
<211> LENGTH: 19
<212> TYPE: PRT
<213> ORGANISM: Artificial Sequence
<220> FEATURE:
<223> OTHER INFORMATION: Synthetic

<400> SEQUENCE: 36

Asn Asp Thr Arg Lys Lys Lys Arg Lys Lys Lys Arg Lys Lys Lys Thr
 1               5                  10                  15

Ser Ala Thr

<210> SEQ ID NO 37
<211> LENGTH: 45
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(45)

<400> SEQUENCE: 37 aac gat act aga aag aag aag aga aag aag aag act agt gcc aca          45
Asn Asp Thr Arg Lys Lys Lys Arg Lys Lys Lys Thr Ser Ala Thr
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Asn Asp Thr Arg Lys Lys Lys Arg Lys Lys Lys Thr Ser Ala Thr
 1               5                  10                  15

<210> SEQ ID NO 39
<211> LENGTH: 24
<212> TYPE: DNA
<213> ORGANISM: Artificial Sequence
```

```
<220> FEATURE:
<223> OTHER INFORMATION: Synthetic
<221> NAME/KEY: CDS
<222> LOCATION: (1)..(24)

<400> SEQUENCE: 39 acc gca tct aga ggt gat aac ttg                                              24
Thr Ala Ser Arg Gly Asp Asn Leu
  1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Thr Ala Ser Arg Gly Asp Asn Leu
  1               5

<210> SEQ ID NO 41
<211> LENGTH: 51
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(51)

<400> SEQUENCE: 41 acc gca tct aga aag aag aaa cgc aaa aag aag act aga ggt gat aac              48
Thr Ala Ser Arg Lys Lys Lys Arg Lys Lys Lys Thr Arg Gly Asp Asn
  1               5                  10                  15 ttg                                                                          51
Leu <210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Thr Ala Ser Arg Lys Lys Lys Arg Lys Lys Lys Thr Arg Gly Asp Asn
  1               5                  10                  15

Leu

<210> SEQ ID NO 43
<211> LENGTH: 54
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(54)

<400> SEQUENCE: 43 tct aga gca gct atg cat gaa ggg act agt gga gac atg cat gca gcc              48
Ser Arg Ala Ala Met His Glu Gly Thr Ser Gly Asp Met His Ala Ala
  1               5                  10                  15 tct aga                                                                      54
Ser Arg
```

```
<210> SEQ ID NO 44
<211> LENGTH: 18
<212> TYPE: PRT
<213> ORGANISM: Artificial Sequence
<220> FEATURE:
<223> OTHER INFORMATION: Synthetic

<400> SEQUENCE: 44

Ser Arg Ala Ala Met His Glu Gly Thr Ser Gly Asp Met His Ala Ala
 1               5                  10                  15
Ser Arg

<210> SEQ ID NO 45
<211> LENGTH: 354
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(354)

<400> SEQUENCE: 45 tct aga gca gct atg cag gcg gcc gca gaa gct gaa gag gca gcc aca        48
Ser Arg Ala Ala Met Gln Ala Ala Ala Glu Ala Glu Glu Ala Ala Thr
 1               5                  10                  15 cgg gct gag gag aag cgc gct gag gcc gaa gca gcg gcc gaa gct gcc        96
Arg Ala Glu Glu Lys Arg Ala Glu Ala Glu Ala Ala Ala Glu Ala Ala
            20                  25                  30 gcc ccc gct gcg caa ccc gag gtc gag aag cct cag aag aaa cag gct       144
Ala Pro Ala Ala Gln Pro Glu Val Glu Lys Pro Gln Lys Lys Gln Ala
        35                  40                  45 aac gct aag gcc gaa gct gtg cag gcg gcc gca gaa gct gaa gag gca       192
Asn Ala Lys Ala Glu Ala Val Gln Ala Ala Ala Glu Ala Glu Glu Ala
    50                  55                  60 gcc aca cgg cct gag gag aag cgc gct gag gcc gaa gca gcg gcc gaa       240
Ala Thr Arg Pro Glu Glu Lys Arg Ala Glu Ala Glu Ala Ala Ala Glu
65                  70                  75                  80 gct gcc gcc ccc gct gcg caa ccc gag gtc gag aag cct gag aag aaa       288
Ala Ala Ala Pro Ala Ala Gln Pro Glu Val Glu Lys Pro Glu Lys Lys
                85                  90                  95 cag gct aac gct aag gcc gaa gct gtg cat gaa ggg act agt gga gag       336
Gln Ala Asn Ala Lys Ala Glu Ala Val His Glu Gly Thr Ser Gly Glu
            100                 105                 110 atg cat gca gcc tct aga                                               354
Met His Ala Ala Ser Arg
        115

<210> SEQ ID NO 46
<211> LENGTH: 118
<212> TYPE: PRT
<213> ORGANISM: Artificial Sequence
<220> FEATURE:
<223> OTHER INFORMATION: Synthetic

<400> SEQUENCE: 46

Ser Arg Ala Ala Met Gln Ala Ala Ala Glu Ala Glu Glu Ala Ala Thr
 1               5                  10                  15

Arg Ala Glu Glu Lys Arg Ala Glu Ala Glu Ala Ala Ala Glu Ala Ala
            20                  25                  30

Ala Pro Ala Ala Gln Pro Glu Val Glu Lys Pro Gln Lys Lys Gln Ala
        35                  40                  45

Asn Ala Lys Ala Glu Ala Val Gln Ala Ala Ala Glu Ala Glu Glu Ala
    50                  55                  60
```

```
Ala Thr Arg Pro Glu Glu Lys Arg Ala Glu Ala Glu Ala Ala Glu
 65                  70                  75                  80

Ala Ala Ala Pro Ala Ala Gln Pro Glu Val Glu Lys Pro Glu Lys Lys
                 85                  90                  95

Gln Ala Asn Ala Lys Ala Glu Ala Val His Glu Gly Thr Ser Gly Glu
            100                 105                 110

Met His Ala Ala Ser Arg
            115

<210> SEQ ID NO 47
<211> LENGTH: 654
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(654)

<400> SEQUENCE: 47 tct aga gca gct atg cag gcg gcc gca gaa gct gaa gag gca gcc aca        48
Ser Arg Ala Ala Met Gln Ala Ala Ala Glu Ala Glu Glu Ala Ala Thr
  1               5                  10                  15 cgg gct gag gag aag cgc gct gag gcc gaa gca gcg gcc gaa gct gcc        96
Arg Ala Glu Glu Lys Arg Ala Glu Ala Glu Ala Ala Ala Glu Ala Ala
             20                  25                  30 gcc ccc gct gcc caa ccc gag gtc gag aag cct cag aag aaa cag gct       144
Ala Pro Ala Ala Gln Pro Glu Val Glu Lys Pro Gln Lys Lys Gln Ala
         35                  40                  45 aac gct aag gcc gaa gct gtg cag gcg gcc gca gaa gct gaa gag gca       192
Asn Ala Lys Ala Glu Ala Val Gln Ala Ala Ala Glu Ala Glu Glu Ala
     50                  55                  60 gcc aca cgg gct gag gag aag cgc gct gag gcc gaa gca gcg gcc gaa       240
Ala Thr Arg Ala Glu Glu Lys Arg Ala Glu Ala Glu Ala Ala Ala Glu
 65                  70                  75                  80 gct gcc gcc ccc gct gcg caa ccc gag gtc gag aag cct cag aag aaa       288
Ala Ala Ala Pro Ala Ala Gln Pro Glu Val Glu Lys Pro Gln Lys Lys
                 85                  90                  95 cag gct aac gct aag gcc gaa gct gtg cat gaa ggg act agt gga gag       336
Gln Ala Asn Ala Lys Ala Glu Ala Val His Glu Gly Thr Ser Gly Glu
            100                 105                 110 atg cag gcg gcc gca gaa gct gaa gag gca gcc aca cgg gct gag gag       384
Met Gln Ala Ala Ala Glu Ala Glu Glu Ala Ala Thr Arg Ala Glu Glu
            115                 120                 125 aag cgc gct gag gcc gaa gca gcg gcc gaa gct gcc gcc ccc gct gcg       432
Lys Arg Ala Glu Ala Glu Ala Ala Ala Glu Ala Ala Ala Pro Ala Ala
        130                 135                 140 caa ccc gag gtc gag aag cct cag aag aaa cag gct aac gct aag gcc       480
Gln Pro Glu Val Glu Lys Pro Gln Lys Lys Gln Ala Asn Ala Lys Ala
145                 150                 155                 160 gaa gct gtg cag gcg gcc gca gaa gct gaa gag gca gcc aca cgg gct       528
Glu Ala Val Gln Ala Ala Ala Glu Ala Glu Glu Ala Ala Thr Arg Ala
                165                 170                 175 gac gag aag cgc gct gag gcc gaa gca gcg gcc gaa gct gcc gcc ccc       576
Asp Glu Lys Arg Ala Glu Ala Glu Ala Ala Ala Glu Ala Ala Ala Pro
            180                 185                 190 gct gcg caa ccc gag gtc gag aag cct cag aag aaa cag gct aac gct       624
Ala Ala Gln Pro Glu Val Glu Lys Pro Gln Lys Lys Gln Ala Asn Ala
        195                 200                 205 aag gcc gaa gct gtg cat gca gcc tct aga                               654
Lys Ala Glu Ala Val His Ala Ala Ser Arg
    210                 215
```

<210> SEQ ID NO 48
<211> LENGTH: 218
<212> TYPE: PRT
<213> ORGANISM: Artificial Sequence
<220> FEATURE:
<223> OTHER INFORMATION: Synthetic

<400> SEQUENCE: 48

Ser Arg Ala Ala Met Gln Ala Ala Glu Ala Glu Ala Ala Thr
 1               5                  10                  15

Arg Ala Glu Glu Lys Arg Ala Glu Ala Glu Ala Ala Glu Ala Ala
                20                  25                  30

Ala Pro Ala Ala Gln Pro Glu Val Glu Lys Pro Gln Lys Gln Ala
            35                  40                  45

Asn Ala Lys Ala Glu Ala Val Gln Ala Ala Glu Ala Glu Glu Ala
        50                  55                  60

Ala Thr Arg Ala Glu Glu Lys Arg Ala Glu Ala Glu Ala Ala Glu
65                  70                  75                  80

Ala Ala Ala Pro Ala Ala Gln Pro Glu Val Glu Lys Pro Gln Lys Lys
                85                  90                  95

Gln Ala Asn Ala Lys Ala Glu Ala Val His Glu Gly Thr Ser Gly Glu
                100                 105                 110

Met Gln Ala Ala Ala Glu Ala Glu Glu Ala Ala Thr Arg Ala Glu Glu
            115                 120                 125

Lys Arg Ala Glu Ala Glu Ala Ala Glu Ala Ala Pro Ala Ala
130                 135                 140

Gln Pro Glu Val Glu Lys Pro Gln Lys Lys Gln Ala Asn Ala Lys Ala
145                 150                 155                 160

Glu Ala Val Gln Ala Ala Glu Ala Glu Glu Ala Ala Thr Arg Ala
                165                 170                 175

Asp Glu Lys Arg Ala Glu Ala Glu Ala Ala Glu Ala Ala Ala Pro
            180                 185                 190

Ala Ala Gln Pro Glu Val Glu Lys Pro Gln Lys Lys Gln Ala Asn Ala
                195                 200                 205

Lys Ala Glu Ala Val His Ala Ala Ser Arg
    210                 215

<210> SEQ ID NO 49
<211> LENGTH: 6
<212> TYPE: PRT
<213> ORGANISM: Artificial Sequence
<220> FEATURE:
<223> OTHER INFORMATION: Synthetic
<223> OTHER INFORMATION: Synthetic
<221> NAME/KEY: misc_feature
<222> LOCATION: (1)..(6)
<223> OTHER INFORMATION: "Asx" is a basic amino acid (e.g., Lys, Arg,
      etc.) and "Xaa" is any other amio acid.

<400> SEQUENCE: 49

Xaa Asx Asx Xaa Asx Xaa
 1               5

<210> SEQ ID NO 50
<211> LENGTH: 8
<212> TYPE: PRT
<213> ORGANISM: Artificial Sequence

```
<220> FEATURE:
<223> OTHER INFORMATION: Synthetic
<221> NAME/KEY: PEPTIDE
<222> LOCATION: (1)..(8)
<223> OTHER INFORMATION: "Asx" is a basic amino acid (e.g., Lys, Arg,
      etc.) and "Xaa" is any other amio acid.

<400> SEQUENCE: 50

Xaa Asx Asx Asx Xaa Xaa Asx Xaa
  1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic

<400> SEQUENCE: 51

Leu Ile Gly Arg Lys Lys Thr
  1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic

<400> SEQUENCE: 52

Leu Ile Gly Arg Lys
  1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic

<400> SEQUENCE: 53

Leu Ile Gly Arg Arg
  1               5

<210> SEQ ID NO 54
<211> LENGTH: 22
<212> TYPE: PRT
<213> ORGANISM: Artificial Sequence
<220> FEATURE:
<223> OTHER INFORMATION: Synthetic

<400> SEQUENCE: 54

Asn Val Ser Pro Pro Arg Arg Ala Arg Val Thr Asp Ala Thr Glu Thr
  1               5                  10                  15

Thr Ile Thr Ile Ser Trp
             20

<210> SEQ ID NO 55
<211> LENGTH: 8
<212> TYPE: PRT
<213> ORGANISM: Artificial Sequence
<220> FEATURE:
<223> OTHER INFORMATION: Synthetic

<400> SEQUENCE: 55

Thr Glu Thr Thr Ile Thr Ile Ser
  1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Synthetic

<400> SEQUENCE: 56

Gly Val Glu Phe Val Cys Cys Pro
 1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Pro Arg Ala Arg Ile
 1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic

<400> SEQUENCE: 58

Trp Gln Pro Pro Arg Ala Arg Ile
 1               5

<210> SEQ ID NO 59
<211> LENGTH: 28
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(18)

<400> SEQUENCE: 59 tca tac att gcc caa gaa taaaaagaa                            28
Ser Tyr Ile Ala Gln Glu
 1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Ser Tyr Ile Ala Gln Glu
 1               5

<210> SEQ ID NO 61
<211> LENGTH: 54
<212> TYPE: DNA
<213> ORGANISM: Artificial Sequence
<220> FEATURE:
<223> OTHER INFORMATION: Synthetic

<400> SEQUENCE: 61
gatcaggatc aggttcaggg agtggctcta aaagaagaa aaagaagaaa taag     54
```

<210> SEQ ID NO 62
<211> LENGTH: 54
<212> TYPE: DNA
<213> ORGANISM: Artificial Sequence
<220> FEATURE:
<223> OTHER INFORMATION: Synthetic

<400> SEQUENCE: 62
gatccttact tcttcttttt cttcttttta gagccactcc ctgaacctga tcct           54

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
caggttgaat actagggttc t                                              21

<210> SEQ ID NO 64
<211> LENGTH: 39
<212> TYPE: DNA
<213> ORGANISM: Artificial Sequence
<220> FEATURE:
<223> OTHER INFORMATION: Synthetic

<400> SEQUENCE: 64
gatccggttc aggatctggc agtggctcga ctagttaaa                           39

<210> SEQ ID NO 65
<211> LENGTH: 39
<212> TYPE: DNA
<213> ORGANISM: Artificial Sequence
<220> FEATURE:
<223> OTHER INFORMATION: Synthetic

<400> SEQUENCE: 65
gatccttaac tagtcgagcc actgccagat cctgaaccg                           39

<210> SEQ ID NO 66
<211> LENGTH: 27
<212> TYPE: DNA
<213> ORGANISM: Artificial Sequence
<220> FEATURE:
<223> OTHER INFORMATION: Synthetic

<400> SEQUENCE: 66
ctagaaagaa gaaacgcaaa aagaaga                                        27

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
ctagtcttct ttttgcgttt cttcttt                                        27

<210> SEQ ID NO 68
<211> LENGTH: 39
<212> TYPE: DNA
<213> ORGANISM: Artificial Sequence
<220> FEATURE:
<223> OTHER INFORMATION: Synthetic

```
<400> SEQUENCE: 68
ctagaaagaa gaagcgcaaa aaaaaaagaa agaagaaga                                    39

<210> SEQ ID NO 69
<211> LENGTH: 42
<212> TYPE: DNA
<213> ORGANISM: Artificial Sequence
<220> FEATURE:
<223> OTHER INFORMATION: Synthetic

<400> SEQUENCE: 69
ctagtcttct tctttctttt tttttgcgc ttcttcttct tt                                 42

<210> SEQ ID NO 70
<211> LENGTH: 42
<212> TYPE: DNA
<213> ORGANISM: Artificial Sequence
<220> FEATURE:
<223> OTHER INFORMATION: Synthetic

<400> SEQUENCE: 70
ctagttatgg gagaaaaaag cgcaggcaac gaagacgggc at                                42

<210> SEQ ID NO 71
<211> LENGTH: 42
<212> TYPE: DNA
<213> ORGANISM: Artificial Sequence
<220> FEATURE:
<223> OTHER INFORMATION: Synthetic

<400> SEQUENCE: 71
ctagatgccc gtcttcgttg cctgcgcttt tttctcccat aa                                42

<210> SEQ ID NO 72
<211> LENGTH: 48
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(48)

<400> SEQUENCE: 72 act agt tat ggg aga aaa aag cgc agg caa cga aga cgg gca tct agt              48
Thr Ser Tyr Gly Arg Lys Lys Arg Arg Gln Arg Arg Arg Ala Ser Ser
 1               5                  10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic

<400> SEQUENCE: 73

Thr Ser Tyr Gly Arg Lys Lys Arg Arg Gln Arg Arg Arg Ala Ser Ser
 1               5                  10                  15

<210> SEQ ID NO 74
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 74

Arg Lys Lys Lys Arg Lys Lys Lys
 1               5

<210> SEQ ID NO 75
<211> LENGTH: 33
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(33)

<400> SEQUENCE: 75 tct aga aaa aaa aaa cgc aag aag aag act agt                33
Ser Arg Lys Lys Lys Arg Lys Lys Lys Thr Ser
 1               5                  10

<210> SEQ ID NO 76
<211> LENGTH: 11
<212> TYPE: PRT
<213> ORGANISM: Artificial Sequence
<220> FEATURE:
<223> OTHER INFORMATION: Synthetic

<400> SEQUENCE: 76

Ser Arg Lys Lys Lys Arg Lys Lys Lys Thr Ser
 1               5                  10

<210> SEQ ID NO 77
<211> LENGTH: 45
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(45)

<400> SEQUENCE: 77 tct aga aag aag aag cgc aaa aaa aaa aga aag aag aag act agt      45
Ser Arg Lys Lys Lys Arg Lys Lys Lys Arg Lys Lys Lys Thr Ser
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Ser Arg Lys Lys Lys Arg Lys Lys Lys Arg Lys Lys Lys Thr Ser
 1               5                  10                  15

<210> SEQ ID NO 79
<211> LENGTH: 39
<212> TYPE: DNA
<213> ORGANISM: Artificial Sequence
<220> FEATURE:
<223> OTHER INFORMATION: Synthetic

<400> SEQUENCE: 79
ctagaaagaa gaagcgcaaa aaaaaagaa agaagaaga                  39
```

```
<210> SEQ ID NO 80
<211> LENGTH: 39
<212> TYPE: DNA
<213> ORGANISM: Artificial Sequence
<220> FEATURE:
<223> OTHER INFORMATION: Synthetic

<400> SEQUENCE: 80
ctagtcttct tctttctttt tttttgcgc ttcttcttt                        39

<210> SEQ ID NO 81
<211> LENGTH: 35
<212> TYPE: DNA
<213> ORGANISM: Artificial Sequence
<220> FEATURE:
<223> OTHER INFORMATION: Synthetic

<400> SEQUENCE: 81
ggacaggggc cctacttta agccctactc tggca                            35

<210> SEQ ID NO 82
<211> LENGTH: 59
<212> TYPE: DNA
<213> ORGANISM: Artificial Sequence
<220> FEATURE:
<223> OTHER INFORMATION: Synthetic

<400> SEQUENCE: 82
atcttcactg tacaatacca ctttaggagt caagttatca cctctagatg cggtcgcct  59

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Thr Glu Ala Thr Gly Asn Gly Asp Asn Leu
  1               5                  10

<210> SEQ ID NO 84
<211> LENGTH: 36
<212> TYPE: DNA
<213> ORGANISM: Artificial Sequence
<220> FEATURE:
<223> OTHER INFORMATION: Synthetic

<400> SEQUENCE: 84
ggactagtag catttaataa aaagaagat aagcgc                            36

<210> SEQ ID NO 85
<211> LENGTH: 28
<212> TYPE: DNA
<213> ORGANISM: Artificial Sequence
<220> FEATURE:
<223> OTHER INFORMATION: Synthetic

<400> SEQUENCE: 85
ccggatcctc attcttgggc gatatagg                                    28

<210> SEQ ID NO 86
<211> LENGTH: 53
<212> TYPE: DNA
<213> ORGANISM: Artificial Sequence
<220> FEATURE:
<223> OTHER INFORMATION: Synthetic
```

<400> SEQUENCE: 86
gggctgcagg cggccgcaga agctgaagag gcagccacac gggctgagga gaa    53

<210> SEQ ID NO 87
<211> LENGTH: 58
<212> TYPE: DNA
<213> ORGANISM: Artificial Sequence
<220> FEATURE:
<223> OTHER INFORMATION: Synthetic

<400> SEQUENCE: 87
ggggtgcaca cagcttcggc cttagcgtta gcctgtttct tctgaggctt ctcgacct    58

<210> SEQ ID NO 88
<211> LENGTH: 32
<212> TYPE: PRT
<213> ORGANISM: Artificial Sequence
<220> FEATURE:
<223> OTHER INFORMATION: Synthetic

<400> SEQUENCE: 88

Ala Thr Arg Ala Glu Glu Asp Arg Ala Glu Ala Glu Ala Ala Ala Glu
 1               5                  10                  15

Ala Ala Ala Pro Ala Ala Gln Pro Glu Val Glu Lys Pro Gln Lys Lys
            20                  25                  30

<210> SEQ ID NO 89
<211> LENGTH: 306
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(306)

<400> SEQUENCE: 89 ctg cag gcg gcc gca gaa gct gaa gag gca gcc aca cgg gct gag gag    48
Leu Gln Ala Ala Ala Glu Ala Glu Glu Ala Ala Thr Arg Ala Glu Glu
 1               5                  10                  15 aag cgc gct gag gcc gaa gca gcg gcc gaa gct gcc gcc ccc gct gcg    96
Lys Arg Ala Glu Ala Glu Ala Ala Ala Glu Ala Ala Ala Pro Ala Ala
             20                  25                  30 caa ccc gac gtc gag aag cct cag aag aaa cag gct aac gct aag gcc   144
Gln Pro Asp Val Glu Lys Pro Gln Lys Lys Gln Ala Asn Ala Lys Ala
         35                  40                  45 gaa gct gtg cag gcg gcc gca gaa gct gaa gag gca gcc aca cgg gct   192
Glu Ala Val Gln Ala Ala Ala Glu Ala Glu Glu Ala Ala Thr Arg Ala
     50                  55                  60 gag gag aag cgc gct gag gcc gaa gca gcg gcc gaa gct gcc gcc ccc   240
Glu Glu Lys Arg Ala Glu Ala Glu Ala Ala Ala Glu Ala Ala Ala Pro
 65                  70                  75                  80 gct gcg caa ccc gag gtc gag aag cct cag aag aaa cag gct aac gct   288
Ala Ala Gln Pro Glu Val Glu Lys Pro Gln Lys Lys Gln Ala Asn Ala
                 85                  90                  95 aag gcc gaa gct gtg cac                                           306
Lys Ala Glu Ala Val His
            100

<210> SEQ ID NO 90
<211> LENGTH: 102
<212> TYPE: PRT
<213> ORGANISM: Artificial Sequence
<220> FEATURE:
<223> OTHER INFORMATION: Synthetic -continued

```
<400> SEQUENCE: 90

Leu Gln Ala Ala Glu Ala Glu Ala Ala Thr Arg Ala Glu Glu
1               5                   10                  15

Lys Arg Ala Glu Ala Glu Ala Ala Glu Ala Ala Pro Ala Ala
                20                  25                  30

Gln Pro Asp Val Glu Lys Pro Gln Lys Gln Ala Asn Ala Lys Ala
            35                  40                  45

Glu Ala Val Gln Ala Ala Glu Ala Glu Ala Ala Thr Arg Ala
        50                  55                  60

Glu Glu Lys Arg Ala Glu Ala Glu Ala Ala Glu Ala Ala Pro
65                  70                  75                  80

Ala Ala Gln Pro Glu Val Glu Lys Pro Gln Lys Gln Ala Asn Ala
                85                  90                  95

Lys Ala Glu Ala Val His
            100

<210> SEQ ID NO 91
<211> LENGTH: 48
<212> TYPE: DNA
<213> ORGANISM: Artificial Sequence
<220> FEATURE:
<223> OTHER INFORMATION: Synthetic

<400> SEQUENCE: 91
ctagagcagc tatgcatgaa gggactagtg gagagatgca tgcagcct                48

<210> SEQ ID NO 92
<211> LENGTH: 48
<212> TYPE: DNA
<213> ORGANISM: Artificial Sequence
<220> FEATURE:
<223> OTHER INFORMATION: Synthetic

<400> SEQUENCE: 92
ctagaggctg catgcatctc tccactagtc ccttcatgca tagctgct                48

<210> SEQ ID NO 93
<211> LENGTH: 14
<212> TYPE: PRT
<213> ORGANISM: Artificial Sequence
<220> FEATURE:
<223> OTHER INFORMATION: Synthetic

<400> SEQUENCE: 93

Ser Ala Cys Asp Cys Arg Gly Asp Cys Phe Cys Gly Thr Ser
1               5                   10

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Arg Lys Lys Lys Arg Lys Lys Lys
1               5
```

VECTORS AND METHODS FOR GENE TRANSFER

CROSS REFERENCE TO RELATED PATENT APPLICATIONS

The present application is a continuation of U.S. patent application Ser. No. 09/101,751, filed Jul. 15, 1998 now U.S. Pat. No. 6,465,253, which, in turn, is the national phase of International Patent Application PCT/US96/19150, designating the U.S. and filed Nov. 27, 1996, a continuation-in-part of U.S. patent application Ser. No. 08/563,368, filed Nov. 28, 1995, now U.S. Pat. No. 5,965,541, and a continuation-in-part of U.S. patent application Ser. No. 08/701,124, filed Aug. 21, 1996, now U.S. Pat. No. 5,846,782, and a continuation-in-part of U.S. patent application Ser. No. 08/700,846, filed Aug. 21, 1996, now U.S. Pat. No. 5,962,311, which, in turn, is a continuation-in-part of U.S. patent application Ser. No. 08/634,060, filed Apr. 17, 1996, now U.S. Pat. No. 5,712,136, which, in turn, is a continuation-in-part of U.S. patent application Ser. No. 08/303,162, filed Sep. 8, 1994, now U.S. Pat. No. 5,559,099.

TECHNICAL FIELD OF THE INVENTION

The present invention pertains to a chimeric adenovirus coat protein which is able to direct entry into cells of a vector comprising the coat protein that is more efficient than a similar vector having a wild-type adenovirus coat protein. Such a chimeric coat protein is a fiber, hexon, or penton protein. The present invention also pertains to a recombinant vector comprising such a chimeric adenoviral coat protein, and to methods of constructing and using such a vector.

BACKGROUND OF THE INVENTION

Adenoviruses belong to the family Adenoviridae, which is divided into two genera, namely *Mastadenovirus* and *Aviadenovirus*. Adenoviruses are nonenveloped, regular icosahedrons of about 65 to 80 nanometers in diameter (Home et al., *J. Mol. Biol.*, 1, 84–86 (1959)). The adenoviral capsid is composed of 252 capsomeres of which 240 are hexons and 12 are pentons (Ginsberg et al., *Virology*, 28, 782–783 (1966)). The hexons and pentons are derived from three different viral polypeptides (Maizel et al., *Virology*, 36, 115–125 (1968); Weber et al., *Virology*, 76, 709–724 (1977)). The hexon comprises three identical polypeptides of 967 amino acids each, namely polypeptide II (Roberts et al., *Science*, 232, 1148–1151 (1986)). The penton contains a penton base, which is bound to the capsid, and a fiber, which is noncovalently bound to and projects from the penton base. The fiber protein comprises three identical polypeptides of 582 amino acids each, namely polypeptide IV. The adenovirus serotype 2 (Ad2) penton base protein is a ring-shaped complex composed of five identical protein subunits of 571 amino acids each, namely polypeptide III (Boudin et al., *Virology*, 92, 125–138 (1979)). Proteins IX, VI, and IIIa are also present in the adenoviral coat and are thought to stabilize the viral capsid (Stewart et al., *Cell*, 67, 145–154 (1991); Stewart et al., *EMBO J.*, 12(7), 2589–2599 (1993)).

Once an adenovirus attaches to a cell, it undergoes receptor-mediated internalization into clathrin-coated endocytic vesicles of the cell (Svensson et al., *J. Virol.*, 51, 687–694 (1984); Chardonnet et al., *Virology*, 40, 462–477 (1970)). Virions entering the cell undergo a stepwise disassembly in which many of the viral structural proteins are shed (Greber et al., *Cell*, 75, 477–486 (1993)). During the uncoating process, the viral particles cause disruption of the cell endosome by a pH-dependent mechanism (Fitzgerald et al., *Cell*, 32, 607–617 (1983)), which is still poorly understood. The viral particles are then transported to the nuclear pore complex of the cell (Dales et al., *Virology*, 56, 465–483 (1973)), where the viral genome enters the nucleus, thus initiating infection.

An adenovirus uses two separate cellular receptors, both of which must be present, to efficiently attach to and infect a cell (Wickham et al., *Cell*, 73, 309–319 (1993)). First, the Ad2 fiber protein attaches the virus to a cell by binding to an as yet unidentified receptor. Then, the penton base binds to $\alpha_v$ integrins, which are a family of heterodimeric cell-surface receptors that mediate cellular adhesion to the extracellular matrix molecules, as well as other molecules (Hynes, *Cell*, 69, 11–25 (1992)).

The fiber protein is a trimer (Devaux et al., *J. Molec. Biol.*, 215, 567–588 (1990)) consisting of a tail, a shaft, and a knob. The fiber shaft region is composed of repeating 15 amino acid motifs, which are believed to form two alternating β-strands and β-bends (Green et al., *EMBO J.*, 2, 1357–1365 (1983)). The overall length of the fiber shaft region and the number of 15 amino-acid repeats differ between adenoviral serotypes. For example, the Ad2 fiber shaft is 37 nanometers long and contains 22 repeats, whereas the Ad3 fiber is 11 nanometers long and contains 6 repeats. The receptor binding domain of the fiber protein is localized in the knob region encoded by the last 200 amino acids of the protein (Henry et al., *J. Virology*, 68(8), 5239–5246 (1994)). The regions necessary for trimerization are also located in the knob region of the protein (Henry et al. (1994), supra). A deletion mutant lacking the last 40 amino acids does not trimerize and also does not bind to penton base (Novelli et al., *Virology*, 185, 365–376 (1991)). Thus, trimerization of the fiber protein is necessary for penton base binding. Nuclear localization signals that direct the protein to the nucleus to form viral particles following its synthesis in the cytoplasm are located in the N-terminal region of the protein (Novelli et al. (1991), supra). The fiber, together with the hexon, are the main antigenic determinants of the virus and also determine the serotype specificity of the virus (Watson et al., *J. Gen. Virol.*, 69, 525–535 (1988)).

Recombinant adenoviral vectors have been used for the cell-targeted transfer of one or more recombinant genes to diseased cells or tissue in need of treatment. Such vectors are characterized by the advantage of not requiring host cell proliferation for expression of adenoviral proteins (Horwitz et al., *In Virology*, Raven Press, New York, vol. 2, pp. 1679–1721 (1990); and Berkner, *BioTechniques*, 6, 616 (1988)). Moreover, if the targeted tissue for somatic gene therapy is the lung, these vectors have the added advantage of being normally trophic for the respiratory epithelium (Straus, In *Adenoviruses*, Plenum Press, New York, pp. 451–496 (1984)).

Other advantages of adenoviruses as potential vectors for human gene therapy are: (i) recombination is rarely observed with use of such vectors; (ii) there are no known associations of human malignancies with adenoviral infections despite common human infection with adenoviruses; (iii) the adenoviral genome (which is a linear, double-stranded DNA) can be manipulated to accommodate foreign genes that range in size; (iv) an adenoviral vector does not insert its DNA into the chromosome of a cell, so its effect is impermanent and unlikely to interfere with the cell's normal function; (v) the adenovirus can infect non-dividing or terminally differentiated cells, such as cells in the brain and lungs; and (vi) live adenovirus, having as an essential characteristic the ability to replicate, has been safely used as a human vaccine (Horwitz et al. (1990), sura; Berkner et al.

(1988), supra; Straus et al. (1984), supra; Chanock et al., *JAMA*, 195, 151 (1966); Haj-Ahmad et al., *J. Virol.*, 57, 267 (1986); and Ballay et al., *EMBO*, 4, 3861 (1985); PCT patent application WO 94/17832).

A drawback to adenovirus-mediated gene therapy is that significant decreases in gene expression are observed after two weeks following administration of the vector. In many therapeutic applications, the loss of expression requires re-administration of the viral vector. However, following re-administration, neutralizing antibodies are raised against both the fiber and hexon proteins of the viral vector (Wohlfart, *J. Virology*, 62, 2321–2328 (1988); Wohlfart et al., *J. Virology*, 56, 896–903 (1985)). This antibody response against the virus can prevent effective re-administration of the viral vector.

Another drawback of using recombinant adenovirus in gene therapy is that certain cells are not readily amenable to adenovirus-mediated gene delivery. For instance, lymphocytes, which lack the $\alpha_v$ integrin adenoviral receptors, are impaired in the uptake of adenoviruses (Silver et al., *Virology* 165, 377–387 (1988); Horvath et al., *J. Virology*, 62(1), 341–345 (1988)). This lack of ability to infect all cells has lead researchers to seek out ways to introduce adenovirus into cells that cannot be infected by adenovirus, e.g. due to lack of adenoviral receptors. In particular, the virus can be coupled to a DNA-polylysine complex containing a ligand (e.g., transferrin) for mammalian cells (e.g., Wagner et al., *Proc. Natl. Acad. Sci.*, 89, 6099–6103 (1992); PCT patent application WO 95/26412). Similarly, adenoviral fiber protein can be sterically blocked with antibodies, and tissue-specific antibodies can be chemically linked to the viral particle (Cotten et al., *Proc. Natl. Acad. Sci. USA*, 89, 6094–6098 (1992)).

However, these approaches are disadvantageous in that they require additional steps that covalently link large molecules, such as polylysine, receptor ligands, and antibodies, to the virus (Cotten (1992), supra; Wagner et al., *Proc. Natl. Acad. Sci.*, 89, 6099–6103 (1992)). This adds to the size of the resultant vector as well as its cost of production. Moreover, the targeted particle complexes are not homogeneous in structure, and their efficiency is sensitive to the relative ratios of viral particles, linking molecules, and targeting molecules used. Thus, this approach for expanding the repertoire of cells amenable to adenoviral-mediated gene therapy is less than optimal.

Recently, the efficiency of adenovirus-mediated gene transfer in vivo to even those cells which adenovirus has been reputed to enter with high efficiency has been called into question (Grubb et al., *Nature*, 371, 802–806 (1994); Dupuit et al., *Human Gene Therapy*, 6, 1185–1193 (1995)). The fiber receptor by means of which adenovirus initially contacts cells has not been identified, and its representation in different tissues has not been examined. It is generally assumed that epithelial cells in the lung and gut produce sufficient levels of the fiber receptor to allow their optimal transduction. However, no studies have confirmed this point to date. In fact, studies have suggested that adenovirus gene delivery to differentiated lung epithelium is less efficient than delivery to proliferating or to undifferentiated cells (Grubb et al., supra; Dupuit et al., supra).

Similarly, adenovirus has been shown to transduce a large number of tissues including lung epithelial cells (Rosenfeld et al., *Cell*, 68, 143–155 (1992)), muscle cells (Quantin et al., *Proc. Natl. Acad. Sci.*, 89, 2581–2584 (1992)), endothelial cells (Lemarchand et al, *Proc. Natl. Acad. Sci.*, 89, 6482–6486 (1992), fibroblasts (Anton et al., *J. Virol.*, 69, 4600–4606 (1995), and neuronal cells (LaSalle et al., *Science*, 259, 988–990 (1993)). However, in many of these studies, very high levels of virus particles have been used to achieve transduction, often exceeding 100 plaque forming units (pfu)/cell, and corresponding to a multiplicity of infection (MOI) of 100. The requirement for a high MOI to achieve transduction is disadvantageous inasmuch as any immune response associated with adenoviral infection necessarily would be exacerbated with use of high doses.

Accordingly, there remains a need for vectors, such as adenoviral vectors, that are capable of infecting cells with a high efficiency, especially at lower MOIs, and that demonstrate an increased host cell range of infectivity. The present invention seeks to overcome at least some of the aforesaid problems of recombinant adenoviral gene therapy. In particular, it is an object of the present invention to provide a vector (such as an adenoviral vector) having a broad host range, and an ability to enter cells with a high efficiency, even at a reduced MOI, thereby reducing the amount of recombinant adenoviral vector administered and any side-effects/complications resulting from such administration. A further object of the present invention is to provide a method of gene therapy involving the use of a homogeneous adenovirus, wherein the viral particle is modified at the level of the adenoviral genome, without the need for additional chemical modifications of viral particles. These and other objects and advantages of the present invention, as well as additional inventive features, will be apparent from the following detailed description.

BRIEF SUMMARY OF THE INVENTION

The present invention provides a chimeric adenoviral coat protein (e.g., a fiber, hexon or penton protein), which differs from the wild-type (i.e., native) fiber protein by the introduction of a nonnative amino acid sequence, preferably at or near the carboxyl terminus. The resultant chimeric adenovirus coat protein is able to direct entry into cells of a vector comprising the coat protein that is more efficient than entry into cells of a vector that is identical except for comprising a,wild-type adenovirus coat protein rather than the chimeric adenovirus coat protein. One direct result of this increased efficiency of entry is that the chimeric adenovirus coat protein enables the adenovirus to bind to and enter numerous cell types which adenovirus comprising wild-type coat protein typically cannot enter or can enter with only a low efficiency. The present invention also provides an adenoviral vector that comprises the chimeric adenovirus coat protein, and methods of constructing and using such a vector.

BRIEF DESCRIPTION OF THE FIGURES

FIG. 1 is a bar graph depicting the binding (percent of input) of wild-type adenovirus to cells derived from different tissues.

FIGS. 2A–B depict attachment of a nucleic acid sequence at the end of the wild-type adenoviral fiber gene (FIG. 2A) to derive a chimeric adenoviral fiber protein (FIG. 2B) comprising a nonnative amino acid sequence at the carboxy terminus. As indicated, the length of the polyA tail, and, consequently, the number of lysines in the resultant protein, can vary.

FIGS. 4A–D depict the oligonucleotides employed for construction of GV10 UTV, i.e., the primers SEQ ID NO:9 (FIG. 4A), SEQ ID NO:10 (FIG. 4B), SEQ ID NO:11 (FIG. 4C), and SEQ ID NO:12 (FIG. 4D).

FIG. 5 depicts a Western blot showing the size increase of the chimeric adenoviral fiber protein (UTV) as compared with the wild-type fiber protein (WT).

DETAILED DESCRIPTION OF THE INVENTION

Figure 3:
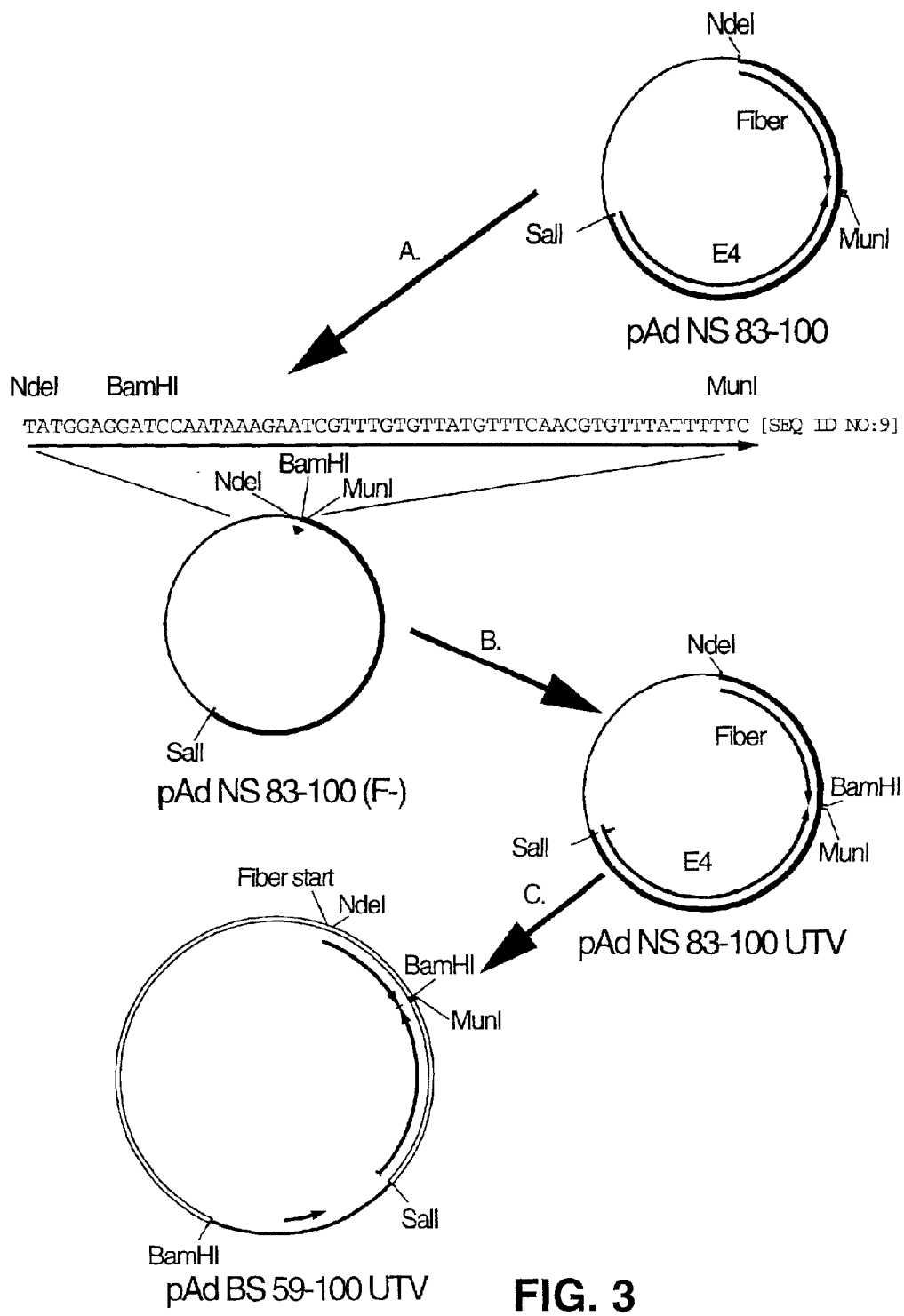
FIG. 3 is a schematic diagram depicting the construction of the adenovirus transfer vector containing chimeric fiber protein pAd BS 59–100 UTV by way of intermediary transfer vectors. In particular, pAd NS 83–100 (also known as p193NS 83–100 or pNS 83–100) is used to derive fiber minus (i.e., F⁻) pAd NS 83–100 (also known as p193NS (ΔF) or pNS (ΔF)) (path A), pAdNS 83 100 (F⁻) is used to derive pAd NS 83–100 UTV (also known as p193NS (F5*), p193 (F5*), or pNS (F5*)) (path B), and pAd NS 83–100 UTV is used to derive pAd BS 59–100 UTV (path C).

The present invention provides, among other things, a recombinant adenovirus comprising a chimeric coat protein, such as a chimeric fiber, penton, and/or hexon protein. The chimeric coat protein comprises a normative amino acid sequence, in addition to, or in place of, a native amino acid sequence. This normative amino acid sequence allows the chimeric fiber (or a vector comprising the chimeric fiber) to more efficiently bind to and enter cells.

Thus, the present invention provides, a chimeric adenovirus coat protein comprising a normative amino acid sequence, wherein the coat protein is able to direct entry into cells of a vector comprising the coat protein that is more efficient than entry into cells of a vector that is identical except for comprising a wild-type adenovirus coat protein rather than the chimeric adenovirus coat protein (i.e., in the absence of the chimeric adenovirus coat protein and in the presence of the wild-type adenovirus coat protein).

Chimeric Coat Protein

A "coat protein" according to the invention preferably comprises a fiber protein (especially an adenoviral fiber protein), a penton protein (especially an adenoviral penton protein), and a hexon protein (especially an adenoviral hexon protein). In particular, a coat protein preferably comprises an adenoviral fiber, penton, or hexon protein. Any one of the serotypes of human or nonhuman adenovirus can be used as the source of the coat protein gene, optimally, however, the adenovirus is an Ad2 or Ad5 adenovirus.

The coat protein is "chimeric" in that it comprises amino acid residues that are not typically found in the protein as isolated from wild-type adenovirus (i.e., comprising the native protein, or wild-type protein). The coat protein thus comprises a "normative amino acid sequence". By "nonnative amino acid sequence" is meant any amino acid sequence that is not found in the native fiber of a given serotype of adenovirus and which preferably is introduced into the fiber protein at the level of gene expression (i.e., by introduction of a "nucleic acid sequence that encodes a normative amino acid sequence").

Such a normative amino acid sequence comprises an amino acid sequence (i.e., has component residues in a particular order) which imparts upon the resultant chimeric protein an ability to bind to and enter cells by means of a novel cell surface binding site (i.e., a "UTV sequence", or Universal Transfer Vector sequence), and/or comprises a sequence incorporated to produce or maintain a certain configuration of the resultant chimeric protein (i.e., a "spacer sequence") between native/nonnative, nonnative/normative, or a native/native sequence. Inasmuch as the normative amino acid sequence is inserted into or in place of an amino acid sequence, and the manipulation of the amino acid sequence of the chimeric coat protein preferably is made at the nucleic acid level, the amino acid sequence that differs in the chimeric coat protein from the wild-type coat protein (i.e., the UTV sequence and the spacer sequence) preferably can comprise an entirely normative amino acid sequence, or a mixture of native and normative amino acids).

A "cell surface binding site" encompasses a receptor (which preferably is a protein, carbohydrate, glycoprotein, or proteoglycan) as well as any oppositely charged molecule (i.e., oppositely charged with respect to the chimeric coat protein, which preferably comprises a normative amino acid sequence that is positively charged, as described further herein) or other type of molecule with which the chimeric coat protein can interact to bind the cell, and thereby promote cell entry. Examples of potential cell surface binding sites include, but are not limited to: negatively charged heparin, heparan sulfate, hyaluronic acid, dermatan sulfate, and chondroitin sulfate moieties, for instance, found on glycosaminoglycans, and which further may contain sialic acid, sulfate, and/or phosphate; sialic acid moieties found on mucins, glycoproteins, and gangliosides; major histocompatibility complex I (MHC I) glycoproteins; common carbohydrate components found in membrane glycoproteins, including mannose, N-acetyl-galactosamine, N-acetyl-glucosamine, fucose, galactose, and the like; and phosphate moieties, for instance, on nucleic acids. However, a chimeric coat protein according to the invention, and methods of use thereof, is not limited to any particular mechanism of cellular interaction (i.e., interaction with a particular cell surface binding site) and is not to be so construed.

Furthermore, such a cell surface binding site is "novel" inasmuch as the site is one that previously was inaccessible to interaction with an adenoviral coat protein (i.e., wild-type adenoviral coat protein such as fiber protein), or was accessible only at a very low level, as reflected by the reduced efficiency of entry of a wild-type adenoviral coat protein-containing vector as compared with a vector comprising a chimeric adenovirus coat protein such as fiber protein according to the invention. Moreover, the binding site is novel in that it is present on the majority of, if not all, cells, regardless of their origin. This is in contrast to the cellular binding site with which wild-type adenoviral fiber protein is presumed to interact, which ostensibly is present only on a subset of cells, or is only accessible on a subset of cells, as reflected by the reduced efficiency of entry of a wild-type adenoviral fiber-containing vector.

"Efficiency of entry" can be quantitated by several means. In particular, efficiency of entry can be quantitated by introducing a chimeric coat protein into a vector, preferably a viral vector, and monitoring cell entry (e.g., by vector-mediated delivery to a cell of a gene such as a reporter gene) as a function of multiplicity of infection (MOI)). In this case, a reduced MOI required for cell entry of a vector comprising a chimeric adenoviral coat protein as compared with a vector that is identical except for comprising a wild-type adenoviral coat protein rather than said chimeric adenovirus coat protein, indicates "more efficient" entry.

Similarly, efficiency of entry can be quantitated in terms of the ability of vectors containing chimeric or wild-type coat proteins, or the soluble chimeric or wild-type coat proteins themselves, to bind to cells. In this case, increased binding exhibited for the vector containing a chimeric adenoviral coat protein, or the chimeric coat protein itself, as compared with the identical vector containing a wild-type coat protein instead, or the wild-type coat protein itself, is indicative of an increased efficiency of entry, or "more efficient" entry.

A nonnative amino acid sequence according to the invention preferably is inserted into or in place of an internal coat protein sequence. Alternately, preferably a normative amino acid sequence according to the invention is at or near the C-terminus of a protein. In particular, when a coat protein according to the invention is a fiber protein, desirably a normative amino acid sequence is at or near the C-terminus of the protein. When a coat protein according to the invention is a penton or hexon protein, preferably a normative amino acid sequence is within an exposed loop of the protein, e.g., as described in the following Examples, particularly within a hypervariable region in loop 1 and/or loop 2 of the adenovirus hexon protein (Crawford-Miksza et al., *J. Virol*., 70, 1836–1844 (1996)). Thus, desirably a nonnative amino acid sequence is in a region of a coat protein that is capable of interacting with and binding a cell.

Furthermore, the method of the invention can be employed to create adenoviral vectors that contain UTV or UTV-like sequences in an extended (or spiked) structure, particularly in hexon and/or penton base protein, so as to result in lengthened hexon and/or penton base proteins, wherein the amino acid insertion projects outward from the protein as it is present in a virion capsid. In particular, such spiked coat proteins can be incorporated into a recombinant adenovirus along with a "short-shafted fiber" (further described herein), wherein the shaft of the fiber has been shortened, and, optionally, the knob of the fiber protein has been replaced with a knob (including the trimerization domain) of another serotype adenoviral vector from which the remainder of the fiber protein derived.

Accordingly, the short-shafted fiber protein preferably can be incorporated into an adenovirus having a chimeric penton base protein that comprises a UTV or UTV-like sequence, or having a "spiked" chimeric penton base protein that furthermore optionally can incorporate a UTV or UTV-like sequence. Also, the short-shafted fiber protein can be incorporated into an adenovirus having a chimeric hexon protein that comprises a UTV or UTV-like sequence, or having a "spiked" chimeric hexon protein that furthermore optionally can incorporate a UTV or UTV-like sequence.

Optimally, the nonnative amino acid sequence is linked to the protein by another normative amino acid sequence, i.e., by an intervening spacer sequence. A spacer sequence is a sequence that intervenes between the native protein sequence and the nonnative sequence, between a normative sequence and another normative sequence, or between a native sequence and another native sequence. A spacer sequence preferably is incorporated into the protein to ensure that the normative sequence comprising the cell surface binding site projects from the three dimensional structure of the chimeric protein (especially the three dimensional structure of the chimeric protein as it exists in nature, i.e., as part of a capsid) in such a fashion so as to be able to interact with and bind to cells. When a spacer sequence is inserted into or replaces an internal coat protein sequence, one or more spacer sequences may be present in the chimeric coat protein.

An intervening spacer sequence can be of any suitable length, preferably from about 3 to about 400 amino acids for a spacer sequence added to derive a "spiked" coat protein (as further described in the following Examples), and preferably from about 3 to about 30 amino acids for any other application described herein. A spacer sequence can comprise any amino acids. Optimally, the spacer sequence does not interfere with the functioning of the coat protein in general, and the functioning of the other normative amino acid sequence (i.e., the UTV or UTV-like sequence) in particular.

The nonnative amino acid sequence which is not a spacer sequence, i.e., the UTV sequence, also can be of any suitable length, preferably from about 3 to about 30 amino acids (although, optionally, as for the spacer sequence, the UTV sequence can be longer, e.g., up to about 400 amino acids). These amino acids preferably are any positively charged residues that are capable of binding to negatively charged moieties present on the surface of a eukaryotic cell, and optimally are capable of binding to negatively charged moieties that are present on the surface of the majority of (if not all) eukaryotic cells. In particular, such a negatively charged moiety present on the surface of a eukaryotic cell to which the UTV sequence binds includes the aforementioned "cell surface binding site".

Desirably the normative amino acid sequence comprises amino acids selected from the group consisting of lysine, arginine and histidine. Alternately, these amino acids can be negatively charged residues that are capable of binding to positively charged cell surface binding sites, e.g., desirably the normative amino acid sequence comprises amino acids selected from the group consisting of aspartate and glutamate.

Thus, the normative amino acid sequence of a coat protein preferably comprises a sequence selected from the group consisting of SEQ ID NO:1 (i.e., Lys Lys Lys Lys Lys Lys Lys Lys), SEQ ID NO:2 (i.e., Arg Arg Arg Arg Arg Arg Arg Arg), and SEQ ID NO:3 (i.e., Xaa Xaa Xaa Xaa Xaa Xaa Xaa Xaa, wherein "Xaa" comprises Lys or Arg), and wherein 1, 2, 3, 4, or 5 residues of the sequence may be deleted at the C-terminus thereof. When the coat protein is a fiber protein, preferably the protein comprises a sequence selected from the group consisting of SEQ ID NO:1, SEQ ID NO:2, SEQ ID NO:3, SEQ ID NO:4 (i.e., Gly Ser Asn Lys Glu Ser Phe Val Leu Lys Lys Lys Lys Lys Lys), and SEQ ID NO:5 (i.e., Ala Gly Ser Asn Lys Asn Lys Glu Ser Phe Val Leu Lys Lys Lys Lys Lys Lys), and wherein 1, 2, 3, 4, or 5 residues of the sequence may be deleted at the C-terminus thereof.

Also, sequences that bind that bind to heparin may be involved in binding to a heparin-like receptor (Sawitzky et al., *Med. Microbiol. Immunol*., 182, 285–92 (1993). Similarly, so-called "heparin binding sequences" may mediate the interaction of the peptide or protein in which they are contained with other cell surface binding sites, such as with cell surface heparan sulfate proteoglycan (Thompson et al., *J. Biol. Chem*., 269, 2541–9 (1994)). Thus, preferably the normative amino acid sequence (i.e., the UTV sequence) comprises these sequences, as well as additional sequences that are capable of recognizing a negatively charged moiety broadly represented on the surface of eukaryotic cells.

In particular, preferably the normative amino acid sequence comprises two basic amino acids (frequently Arg) located about 20 Å apart, facing in opposite directions of an alpha helix (Margalit et al., *J. Biol. Chem*., 269, 19228–31 (1993); Ma et al., *J. Lipid Res.,* 35, 2049–2059 (1994)). Other basic amino acids desirably are dispersed between these two residues, facing one side, while nonpolar residues face the other side, forming an amphipathic structure, which optimally comprises the motif XBBXBX [SEQ ID NO:49] or XBBBXXBX [SEQ ID NO:50], where B is a basic amino acid (e.g., Lys, Arg, etc.), and X is any other amino acid.

Also, preferably the UTV nonnative amino acid sequence comprises: the sequence LIGRKKT [SEQ ID NO:51], LIGRK [SEQ ID NO:52] or LIGRR [SEQ ID NO:53], which are common heparin binding motifs present in fibronectin and heat shock proteins (Hansen et al., *Biochim. Biophys. Acta*, 1252, 135–45 (1995)); insertions of 7 residues of either Lys or Arg, or mixtures of Lys and Arg (Fromm et al., *Arch. Biochem. Biophys*., 323, 279–87 (1995)); the common basic C-terminal region of IGFBP-3 and IGFBP-5 of about 18 amino acids and which comprises a heparin binding sequence (Booth et al., *Growth Regul*., 5, 1–17 (1995)); either one or both of the two hyaluronan (HA) binding motifs located within a 35 amino acid region of the C-terminus of the HA receptor RHAMM (Yang et al., *J. Cell Biochem*., 56, 455–68 (1994)); a synthetic peptide (Ala347-Arg361) modeled after the heparin-binding form of *Staphylococcus aureus* vitronectin comprising heparin-binding consensus sequences (Liang et al., *J. Biochem*., 116, 457–63 (1994)); any one or more of five heparin binding sites between amino acid 129 and 310 of bovine herpesvirus 1 glycoprotein gIII or any one of four heparin binding sites between amino acids 90 and 275 of pseudorabies virus glycoprotein gIII (Liang et al., *Virol*., 194, 233–43 (1993)); amino acids 134 to 141 of pseudorabies virus glycoprotein gIII (Sawitzky et al., *Med. Microbiol. Immunol.,* 182, 285–92 (1993); heparin binding regions corresponding to charged residues at positions 279–282 and 292–304 of human lipoprotein lipase (Ma et al., supra); a synthetic 22 residue peptide, N22W, with a sequence NVSPPRRARVT-DATETTITISW [SEQ ID NO:54] or residues TETTITIS [SEQ ID NO:55] of this synthetic peptide modeled after fibronectin and which exhibit heparin binding properties (Ingham et al., *Arch. Biochem. Biophys*., 314, 242–246 (1994)); GVEFVCCP [SEQ ID NO:56] motif present in the ectodomain zinc binding site of the Alzheimer beta-amyloid precursor protein (APP), as well as various other APP-like proteins, which modulates heparin affinity (Bush et al., *J. Biol. Chem*., 229, 26618–21 (1994)); 8 amino acid residue peptides derived from the cross-region of the laminin A chain (Tashiro et al., *Biochem. J*., 302, 73–9 (1994)); synthetic peptides based on the heparin binding regions of the serine protease inhibitor antithrombin III including peptides F123-G148 and K121-A134 (Tyler-Cross et al., *Protein Sci*., 3, 620–7 (1994)); a 14 K N-terminal fragment of APP and a region close to the N-terminus (i.e., residues 96–110) proposed as heparin binding regions (Small et al., *J. Neurosci*., 14, 2117–27 (1994)); a stretch of 21 amino acids of the heparin binding epidermal growth factor-like growth factor (HB-EGF) characterized by a high content of lysine and arginine residues (Thompson et al., *J. Biol. Chem*., 269, 2541–9 (1994)); a 17 amino acid region comprising the heparin binding region of thrombospondin and corresponding to a hep 1 synthetic peptide (Murphy-Ullrich et al., *J. Biol. Chem*., 268, 26784–9 (1993)); a 23 amino acid sequence (Y565-A587) of human von Willebrand factor that binds heparin (Tyler-Cross et al., *Arch. Biochem. Biophys*., 306, 528–33 (1993)); the fibronectin-derived peptide PRARI [SEQ ID NO:57](and larger peptides comprising this motif, such as WQPPRARI [SEQ ID NO:58]) that binds heparin (Woods et al., *Mol. Biol. Cell.*, 4, 605–613 (1993); the heparin binding region of platelet factor 4 (Sato et al., *Jpn. J. Cancer Res.*, 84, 485–8 (1993); and the K18K sequence in the fibroblast growth factor receptor tyrosine kinase transmembrane glycoprotein (Kan et al., *Science*, 259, 1918–21 (1993)).

Moreover, the UTV sequence can comprise other sequences that are described in the Examples which follow. Thus, preferably the UTV sequence is selected from the group consisting of [SEQ ID NO:19 , [SEQ ID NO:2], [SEQ ID NO:3], [SEQ ID NO:4], [SEQ ID NO:5], [SEQ ID NO:20], [SEQ ID NO:22], [SEQ ID NO:24], [SEQ ID NO:26], [SEQ ID NO:28], [SEQ ID NO:30], [SEQ ID NO:32],[SEQ ID NO:34], [SEQ ID NO:36], [SEQ ID NO:38], [SEQ ID NO:40], [SEQ ID NO:42], [SEQ ID NO:46], [SEQ ID NO:48], [SEQ ID NO:49], [SEQ ID NO:50], [SEQ ID NO:5], [SEQ ID NO:52], [SEQ ID NO:53], [SEQ ID NO:54], [SEQ ID NO:55], [SEQ ID NO:56], [SEQ ID NO:57], [SEQ ID NO:58], [SEQ ID NO:73], [SEQ ID NO:74], [SEQ ID NO:76], [SEQ ID NO:78],[SEQ ID NO:90], and [SEQ ID NO:93]. These sequences also can be employed wherein 1, 2, or 3 residues of the sequence are deleted at the C- or N-terminus. Also, inasmuch as a spacer sequence can be any sequence of amino acids that does not interfere with the functioning of the protein, according to the invention, any of the aforementioned UTV sequences also can comprise spacer sequences.

It also is preferable that the nonnative amino acid sequence comprise amino acid sequences that are "equivalents" of any of the aforementioned sequences (i.e., are "UTV-like sequences"). An equivalent can be a sequence that carries out the same function (with perhaps minor differences in effectiveness), and yet may differ slightly in terms of its amino acid sequence, or other structural features. In particular, an equivalent sequence is one that comprises one or more conservative amino acid substitutions of the sequence. A "conservative amino acid substitution" is an amino acid substituted by an alternative amino acid of similar charge density, hydrophilicity/hydrophobicity, size, and/or configuration (e.g., Val for Ile). In comparison, a "nonconservative amino acid substitution" is an amino acid substituted by an alternative amino acid of differing charge density, hydrophilicity/hydrophobicity, size, and/or configuration (e.g., Val for Phe).

Nucleic Acid Encoding a Chimeric Coat Protein

As indicated previously, preferably the normative amino acid sequence is introduced at the level of DNA. Accordingly, the invention preferably also provides an isolated and purified nucleic acid encoding a coat protein according to the invention, wherein the nucleic acid sequence that encodes the nonnative amino acid sequence comprises a sequence of SEQ ID NO:6 (i.e., GGA TCC AA), which is located prior to the polyadenylation site. Similarly, the invention preferably provides an isolated and purified nucleic acid comprising a sequence selected from the group consisting of SEQ ID NO:7 (i.e., GGA TCC AAT AAA GAA TCG TTT GTG TTA TGT) and SEQ ID NO:8 (i.e., GCC GGA TCC AAC AAG AAT AAA GAA TCG TTT GTG TTA), [SEQ ID NO:19], [SEQ ID NO:21], [SEQ ID NO:23], [SEQ ID NO:25], [SEQ ID NO:27], [SEQ ID NO:29], [SEQ ID NO:31], [SEQ ID NO:33], [SEQ ID NO:35], [SEQ ID NO:37], [SEQ ID NO:39], [SEQ ID NO:41], [SEQ ID NO:45], [SEQ ID NO:47], [SEQ ID NO:72], [SEQ ID NO:75], [SEQ ID NO:77], and [SEQ ID NO:89]. The invention further provides conservatively modified variants of these nucleic acids.

A "conservatively modified variant" is a variation on the nucleic acid sequence that results in a conservative amino acid substitution. In comparison, a "nonconservatively modified variant" is a variation on the nucleic acid sequence that results in a nonconservative amino acid substitution. The means of making such modifications are well known in the art, are described in the Examples which follow, and also can be accomplished by means of commercially available kits and vectors (e.g., New England Biolabs, Inc., Beverly, MA; Clontech, Palo Alto, Calif.). Moreover, the means of assessing such substitutions (e.g., in terms of effect on ability to bind and enter cells) are described in the Examples herein.

The means of making such a chimeric coat protein, particularly the means of introducing the sequence at the level of DNA, is well known in the art, is illustrated in FIG. 2 for a representative chimeric protein, and is described in the Examples that follow. Briefly, the method comprises introducing a sequence (preferably the sequence of SEQ ID NO:6 or a conservatively modified variant thereof) into the sequence of the coat protein. In one preferred embodiment described in the Examples which follow, the introduction is made prior to any stop codon or polyadenylation signal so as to induce a frameshift mutation into the resultant protein, such that the chimeric protein incorporates additional amino acids.

Generally, this can be accomplished by cloning the fiber sequence into a plasmid or some other vector for ease of manipulation of the sequence. Then, restriction sites flanking the sequence at which the frameshift mutation is to be introduced are identified. A double-stranded synthetic oligonucleotide is created from overlapping synthetic single-stranded sense and antisense oligonucleotides (e.g., from the sense and antisense oligonucleotides, respectively, TAT GGA GGA TCC AAT AAA GAA TCG TTT GTG TTA TGT TTC AAC GTG TTT ATT TTT C [SEQ ID NO:9] and AAT TGA AAA ATA AAC ACG TTG AAA CAT AAC ACA AAC GAT TCT TTA TTG GAT CCT CCA [SEQ ID NO:10], as illustrated in FIG. 4) such that the double-stranded oligonucleotide incorporates the restriction sites flanking the target sequence. The plasmid or other vector is cleaved with the restriction enzymes, and the oligonucleotide sequence having compatible cohesive ends is ligated in to the plasmid or other vector, to replace the wild-type DNA. Other means of in vitro site-directed mutagenesis such as are known to those skilled in the art, and can be accomplished (in particular, using PCR), for instance, by means of commercially available kits, can be used to introduce the mutated sequence into the coat protein coding sequence.

Once the sequence is introduced into the chimeric coat protein, the nucleic acid fragment encoding the sequence can be isolated, e.g., by PCR amplification using 5' and 3' primers. For instance, with respect to a chimeric fiber protein, the fragment can be isolated by PCR using the primer TCCC CCCGGG TCTAGA TTA GGA TCC TTC TTG GGC AAT GTA TGA [SEQ ID NO:11], and the primer CGT GTA TCC ATA TGA CAC AGA [SEQ ID NO:12], as illustrated in FIG. 4. Use of these primers in this fashion results in an amplified chimeric fiber-containing fragment that is flanked by restriction sites (i.e., in this case NdeI and BamHI sites) that can be used for convenient subcloning of the fragment. Other means of generating a chimeric coat protein also can be employed.

Thus, the frameshift mutation can be introduced into any part of a coat protein coding sequence. With respect to SEQ ID NO:6, for instance, this sequence can be placed at the region of the coat protein gene that codes for the C-terminus of the protein (i.e., can be added immediately prior to the TAA stop codon), or can be placed earlier into the coding region, such as between codons coding for Ala (i.e., A) and Gln (i.e., Q) to produce the aforementioned coding sequence of SEQ ID NO:8, which encodes a chimeric protein comprising the sequence of SEQ ID NO:5. Similarly, this approach can be employed to introduce a frameshift even earlier in the coding sequence, e.g., either inserted into or in place of an internal (i.e., native) coat protein sequence.

Moreover, the double-stranded oligonucleotide can also incorporate a further restriction site that also can be employed in manipulating the sequence. For instance, the sequence of SEQ ID NO:6 introduced in the vector comprises a modified BamHI site, i.e., the site is "modified" in that it adds additional nucleotides onto the palindromic recognition sequence. This sequence also can be synthesized to comprise any other restriction site convenient for DNA manipulations. When incorporated into the coat protein coding sequence, the sequence not only introduces a frame shift mutation, but also can be used to introduce other coding sequences into the coat protein gene. In particular, the coding sequences introduced in this fashion can comprise codons for lysine, arginine and histidine, or codons for aspartate and glutamate, either alone, or in any combination. Furthermore, a new translation stop codon can follow these codons for the amino acids, allowing a chimeric protein to be produced that only incorporates a given number of additional amino acids in the nonnative amino acid sequence. The codons for the amino acids and the translation stop codon can be introduced into the frameshift mutation-inducing novel restriction site incorporated into the coat protein by synthesizing oligonucleotides comprising these sequences that are flanked by the restriction site as previously described (e.g., that comprise 5' and 3' BamHI sites), or by other such means that are known to those skilled in the art.

The size of the DNA used to replace the native receptor binding sequence may be constrained, for example, by impeded folding of the fiber or improper assembly of the penton base/fiber complex. DNA encoding the aforementioned amino acid sequences (e.g., lysine, arginine, histidine, aspartate, glutamate, and the like) is preferred for insertion into the fiber gene sequence in which the native receptor binding sequence has been deleted or otherwise mutated. Moreover, other DNA sequences, such as those that encode amino acids for incorporation into spacer sequences, preferably are used to replace the native coat protein coding sequence.

Vector Comprising a Chimeric Coat Protein

A "vector" according to the invention is a vehicle for gene transfer as that term is understood by those skilled in the art. Four types of vectors encompassed by the invention are plasmids, phages, viruses, and liposomes. Plasmids, phages, and viruses can be transferred to a cell in their nucleic acid form, and liposomes can be employed to transfer nucleic acids. Hence, the vectors that can be employed for gene transfer are referred to herein as "transfer vectors".

Preferably, a vector according to the invention is a virus, especially a virus selected from the group consisting of nonenveloped viruses, i.e., nonenveloped RNA or DNA viruses. Also, a virus can be selected from the group consisting of enveloped viruses, i.e., enveloped RNA or DNA viruses. Such viruses preferably comprise a coat protein. Desirably, the viral coat protein is one that projects outward from the capsid such that it is able to interact with cells. In the case of enveloped RNA or DNA viruses, preferably the coat protein is in fact a lipid envelope glycoprotein (i.e., a so-called spike or peplomer).

In particular, preferably a vector is a nonenveloped virus (i.e., either a RNA or DNA virus) from the family Hepadnaviridae, Parvoviridae, Papovaviridae, Adenoviridae, or Picornaviridae. A preferred nonenveloped virus according to the invention is a virus of the family Hepadnaviridae, especially of the genus *Hepadnavirus*. A virus of the family Parvoviridae desirably is of the genus *Parvovirus* (e.g., parvoviruses of mammals and birds) or *Dependovirus* (e.g., adeno-associated viruses (AAVs)). A virus of the family Papovaviridae preferably is of the subfamily *Papillomavirinae* (e.g., the papillomaviruses including, but not limited to, human papillomaviruses (HPV) 1–48) or the subfamily Polyomavirinae (e.g., the polyomaviruses including, but not limited to, JC, SV40 and BK virus). A virus of the family Adenoviridae desirably is of the genus *Mastadenovirus* (e.g., mammalian adenoviruses) or *Aviadenovirus* (e.g., avian adenoviruses). A virus of the family Picornaviridae is preferably a hepatitis A virus (HAV), hepatitis B virus (HBV), or a non-A or non-B hepatitis virus.

Similarly, a vector can be an enveloped virus from the family Herpesviridae or Retroviridae, or can be a Sindbis virus. A preferred enveloped virus according to the invention is a virus of the family Herpesviridae, especially of the subfamily or genus *Alphaherpesvirinae* (e.g., the herpes simplex-like viruses), *Simplexvirus* (e.g., herpes simplex-like viruses), *Varicellavirus* (e.g., varicella and pseudorabies-like viruses), *Betaherpesvirinae* (e.g., the cytomegaloviruses), *Cytomegalovirus* (e.g., the human cytomegaloviruses), *Gammaherpesvirinae* (e.g., the lymphocyte-associated viruses), and *Lymphocryptovirus* (e.g., EB-like viruses).

Another preferred enveloped virus is a RNA virus of the family Retroviridae (i.e., preferably is a retrovirus), particularly a virus of the genus or subfamily *Oncovirinae, Spumavirinae, Spumavirus, Lentivirinae*, and *Lentivirus*. A RNA virus of the subfamily Oncovirinae is desirably a human T-lymphotropic virus type 1 or 2 (i.e., HTLV-1 or HTLV-2) or bovine leukemia virus (BLV), an avian leukosis-sarcoma virus (e.g., Rous sarcoma virus (RSV), avian myeloblastosis virus (AMV), avian erythroblastosis virus (AEV), Rous-associated virus (RAV)-1 to 50, RAV-0), a mammalian C-type virus (e.g., Moloney murine leukemia virus (MuLV), Harvey murine sarcoma virus (HaMSV), Abelson murine leukemia virus (A-MuLV), AKR-MuLV, feline leukemia virus (FeLV), simian sarcoma virus, reticuloendotheliosis virus (REV), spleen necrosis virus (SNV)), a B-type virus (e.g., mouse mammary tumor virus (MMTV)), or a D-type virus (e.g., Mason-Pfizer monkey virus (MPMV), "SAIDS" viruses). A RNA virus of the subfamily *Lentivirus* is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or terms "AIDS virus" or "human immunodeficiency virus" are used herein to refer to these HIV viruses, and HIV-related and -associated viruses, generically. Moreover, a RNA virus of the subfamily *Lentivirus* preferably is a Visna/maedi virus (e.g., such as infect sheep), a feline immunodeficiency virus (FIV), bovine lentivirusu, simian immunodeficiency virus (SIV), an equine infectious anemia virus (EIAV), or a caprine arthritis-encephalitis virus (CAEV).

An especially preferred vector according to the invention is an adenoviral vector (i.e., a viral vector of the family Adenoviridae, optimally of the genus *Mastadenovirus*). Desirably such a vector is an Ad2 or Ad5 vector, although other serotype adenoviral vectors can be employed. The adenoviral vector employed for gene transfer can be wild-type (i.e., replication competent). Alternately, the adenoviral vector can comprise genetic material with at least one modification therein, which can render the virus replication deficient. The modification to the adenoviral genome can include, but is not limited to, addition of a DNA segment, rearrangement of a DNA segment, deletion of a DNA segment, replacement of a DNA segment, or introduction of a DNA lesion. A DNA segment can be as small as one nucleotide and as large as 36 kilobase pairs (i.e., the approximate size of the adenoviral genome) or, alternately, can equal the maximum amount which can be packaged into an adenoviral virion (i.e., about 38 kb). Preferred modifications to the adenoviral genome include modifications in the E1, E2, E3 or E4 region. Similarly, an adenoviral vector can be a cointegrate, i.e., a ligation of adenoviral sequences, with other sequences, such as other virus or plasmid sequences.

In terms of a viral vector (e.g., particularly a replication deficient adenoviral vector), such a vector can comprise either complete capsids (i.e., including a viral genome such as an adenoviral genome) or empty capsids (i.e., in which a viral genome is lacking, or is degraded, e.g., by physical or chemical means). Along the same lines, since methods are available for transferring viruses, plasmids, and phages in the form of their nucleic acid sequences (i.e., RNA or DNA), a vector (i.e., a transfer vector) similarly can comprise RNA or DNA, in the absence of any associated protein such as capsid protein, and in the absence of any envelope lipid. Similarly, since liposomes effect cell entry by fusing with cell membranes, a transfer vector can comprise liposomes (e.g., such as are commercially available, for instance, from Life Technologies, Bethesda, Md.), with constitutive nucleic acids encoding the coat protein. Thus, according to the invention whereas a vector "comprises" a chimeric adenoviral coat protein, a transfer vector "encodes" a chimeric adenoviral coat protein; liposome transfer vectors in particular "encode" in the sense that they contain nucleic acids which, in fact, encode the protein.

A vector according to the invention can comprise additional sequences and mutations, e.g., some within the coat protein itself. For instance, a vector according to the invention further preferably comprises a nucleic acid comprising a passenger gene.

A "nucleic acid" is a polynucleotide (DNA or RNA). A "gene" is any nucleic acid sequence coding for a protein or a nascent RNA molecule. A "passenger gene" is any gene which is not typically present in and is subcloned into a vector (e.g., a transfer vector) according to the present invention, and which upon introduction into a host cell is accompanied by a discernible change in the intracellular environment (e.g., by an increased level of deoxyribonucleic acid (DNA), ribonucleic acid (RNA), peptide or protein, or by an altered rate of production or degradation thereof). A "gene product" is either an as yet untranslated RNA molecule transcribed from a given gene or coding sequence (e.g., mRNA or antisense RNA) or the polypeptide chain (i.e., protein or peptide) translated from the mRNA molecule transcribed from the given gene or coding sequence. Whereas a gene comprises coding sequences plus any non-coding sequences, a "coding sequence" does not include any non-coding (e.g., regulatory) DNA. A gene or coding sequence is "recombinant" if the sequence of bases along the molecule has been altered from the sequence in which the gene or coding sequence is typically found in nature, or if the sequence of bases is not typically found in nature. According to this invention, a gene or coding sequence can be wholly or partially synthetically made, can comprise genomic or complementary DNA (cDNA) sequences, and can be provided in the form of either DNA or RNA.

Non-coding sequences or regulatory sequences include promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs, even from a position downstream of a transcribed region. According to the invention, a coding sequence is "operably linked" to a promoter (e.g., when both the coding sequence and the promoter constitute a passenger gene) when the promoter is capable of directing transcription of that coding sequence.

Accordingly, a "passenger gene" can be any gene, and desirably is either a therapeutic gene or a reporter gene. Preferably a passenger gene is capable of being expressed in a cell in which the vector has been internalized. For instance, the passenger gene can comprise a reporter gene, or a nucleic acid sequence which encodes a protein that can in some fashion be detected in a cell. The passenger gene also can comprise a therapeutic gene, for instance, a therapeutic gene which exerts its effect at the level of RNA or protein. For instance, a protein encoded by a transferred therapeutic gene can be employed in the treatment of an inherited disease, such as, e.g., the cystic fibrosis transmembrane conductance regulator cDNA for the treatment of cystic fibrosis. The protein encoded by the therapeutic gene may exert its therapeutic effect by resulting in cell killing. For instance, expression of the gene in itself may lead to cell killing, as with expression of the diphtheria toxin A gene, or the expression of the gene may render cells selectively sensitive to the killing action of certain drugs, e.g., expression of the HSV thymidine kinase gene renders cells sensitive to antiviral compounds including acyclovir, gancyclovir and FIAU (1-(2-deoxy-2-fluoro-$\beta$-D-arabinofuranosil)-5-iodouracil).

Moreover, the therapeutic gene can exert its effect at the level of RNA, for instance, by encoding an antisense message or ribozyme, a protein which affects splicing or 3' processing (e.g., polyadenylation), or can encode a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Accordingly, the use of the term "therapeutic gene" is intended to encompass these and any other embodiments of that which is more commonly referred to as gene therapy and is known to those of skill in the art. Similarly, the recombinant adenovirus can be used for gene therapy or to study the effects of expression of the gene in a given cell or tissue in vitro or in vivo.

The recombinant adenovirus comprising a chimeric coat protein such as a fiber protein and the recombinant adenovirus that additionally comprises a passenger gene or genes capable of being expressed in a particular cell can be generated by use of a transfer vector, preferably a viral or plasmid transfer vector, in accordance with the present invention. Such a transfer vector preferably comprises a chimeric adenoviral coat protein gene sequence as previously described. The chimeric coat protein gene sequence comprises a nonnative sequence in place of the native sequence, which has been deleted, or in addition to the native sequence.

A recombinant chimeric coat protein gene sequence (such as a fiber gene sequence) can be moved from an adenoviral transfer vector into baculovirus or a suitable prokaryotic or eukaryotic expression vector for expression and evaluation of receptor or protein specificity and avidity, trimerization potential, penton base binding, and other biochemical characteristics.

Accordingly, the present invention also provides recombinant baculoviral and prokaryotic and eukaryotic expression vectors comprising a chimeric adenoviral coat protein gene sequence (preferably a fiber gene sequence), which also are "transfer vectors" as defined herein. The chimeric coat protein gene sequence (e.g., fiber gene sequence) includes a nonnative sequence in addition to or in place of a native amino acid sequence, and which enables the resultant chimeric coat protein (e.g., fiber protein) to bind to a binding site other than a binding site bound by the native sequence. By moving the chimeric gene from an adenoviral vector to baculovirus or a prokaryotic or eukaryotic expression vector, high protein expression is achievable (approximately 5–50% of the total protein being the chimeric fiber).

A vector according to the invention further can comprise, either within, in place of, or outside of the coding sequence of a coat protein additional sequences that impact upon the ability of a coat protein such as fiber protein to trimerize, or comprise a protease recognition sequence. A sequence that impacts upon the ability to trimerize is one or more sequences that enable trimerization of a chimeric coat protein that is a fiber protein. A sequence that comprises a protease recognition sequence is a sequence that can be cleaved by a protease, thereby effecting removal of the chimeric coat protein (or a portion thereof) and attachment of the recombinant adenovirus to a cell by means of another coat protein. When employed with a coat protein that is a fiber protein, the protease recognition site preferably does not affect fiber trimerization or receptor specificity of the fiber protein. For instance, in one embodiment of the present invention, preferably the fiber protein, or a portion thereof, is deleted in by means of a protease recognition sequence, and then the novel cell surface binding site is incorporated into either the penton base or hexon coat protein, preferably with use of a spacer sequence as previously described.

In terms of the production of vectors and transfer vectors according to the invention, transfer vectors are constructed using standard molecular and genetic techniques such as are known to those skilled in the art. Vectors (e.g., virions or virus particles) are produced using viral vectors. For instance, a viral vector comprising a chimeric coat protein according to the invention can be constructed by providing to a cell that does not comprise any E4 complementing sequences: (1) a linear vector comprising the chimeric fiber and the wild-type E4 gene, and (2) a linear vector that is E4$^-$, as illustrated in FIG. 3. As described in the Examples which follow, this methodology results in recombination between the sequences, generating a vector that comprises a portion of the initial E4$^-$ vector and a portion of the E4$^+$ vector, particularly the region comprising the chimeric fiber sequences.

Similarly, the fiber chimera-containing particles are produced in standard cell lines, e.g., those currently used for adenoviral vectors. Following production and purification, the particles in which fiber is to be deleted are rendered fiberless through digestion of the particles with a sequence-specific protease, which cleaves the fiber proteins and releases them from the viral particles to generate fiberless particles. For example, thrombin recognizes and cleaves at known amino acid sequences that can be incorporated into the vector (Stenflo et al., *J. Biol. Chem.*, 257, 12280–12290 (1982)). Similarly, deletion mutants lacking the fiber gene can be employed in vector construction, e.g., H2dl802, H2dl807, and H2dl1021 (Falgout et al., *J. Virol.*, 62, 622–625 (1988)). These fiberless particles have been shown to be stable and capable of binding and infecting cells (Falgout et al., supra). These resultant particles then can be targeted to specific tissues via the penton base or other coat protein, preferably such other coat protein that comprises one or more nonnative amino acid sequences according to the invention.

Alternately, recombinant adenovirus comprising chimeric fiber protein having further modifications can be produced by the removal of the native knob region, which comprises receptor-binding and trimerization domains, of the fiber protein and its replacement with a nonnative trimerization domain (Peteranderl et al., *Biochemistry*, 31, 12272–12276 (1992)) and a nonnative amino acid sequence according to the invention. A recombinant adenovirus comprising a chimeric fiber protein also can be produced by point mutation in the knob region and the isolation of clones that are capable of trimerization. In either case, and also with respect to the removal and replacement of the native receptor-specific binding sequence as described above, new protein binding domains can be added onto the C-terminus of the fiber protein or into exposed loops of the fiber protein by inserting one or more copies of the nucleic acid sequence encoding the nonnative amino acid sequence into the appropriate position. Preferably, such a fiber protein is able to trimerize, so that it is able to bind to penton base protein.

The method described above for generating chimeric fiber protein also can be used to make other chimeric coat proteins, e.g., chimeric hexon or penton protein. For example, the RGD amino acid sequence of the penton base protein is replaced at the DNA level with an amino acid binding sequence for a given receptor, receptor-specific antibody domain or epitope. Alternatively, the RGD amino acid sequence is rendered inactive at the DNA level by mutation of the RGD amino acid sequence, such as by insertional mutagenesis, for example, or rendered conformationally inaccessible in the penton base protein, such as by insertion of a DNA sequence into or adjacent to the adenoviral penton base gene sequence, wherein "gene sequence" refers to the complete penton base gene sequence as well as any lesser gene sequences that are capable of being expressed as functional penton base protein. Preferably, the DNA sequence is inserted near the gene sequence encoding the RGD amino acid sequence, so as to move the gene sequence encoding the RGD amino acid sequence within the penton base gene sequence such that in the chimeric penton base protein the RGD amino acid sequence is conformationally inaccessible for binding to a receptor. In the latter case, the inserted nonpenton base gene sequence that causes the conformational inaccessibility of the RGD amino acid sequence in the penton base protein is preferably one that encodes an amino acid sequence that is specific for binding to a receptor, a receptor-specific antibody domain or epitope. Removal, inactivation, or the rendering of the RGD amino acid sequence conformationally inaccessible alters or eliminates the ability of the penton base molecule to bind an $\alpha_v$ integrin receptor.

Illustrative Uses

The present invention provides a chimeric protein that is able to bind to cells and mediate entry into cells with high efficiency, as well as vectors and transfer vectors comprising same. The chimeric coat protein itself has multiple uses, e.g., as a tool for studies in vitro of adenovirus binding to cells (e.g., by Scatchard analysis as shown previously by Wickham et al. (1993), supra), to block binding of adenovirus to receptors in vitro (e.g., by using antibodies, peptides, and enzymes, as described in the Examples), and to protect against adenoviral infection in vivo by competing for binding to the binding site by which adenovirus effects cell entry.

A vector comprising a chimeric coat protein also can be used in strain generation and as a means of making new vectors. For instance, the nonnative amino acid sequence can bind to nucleic acids, and can be introduced intracellularly as a means of generating new vectors via recombination. Similarly, a vector can be used in gene therapy. For instance, a vector of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly. Diseases that are candidates for such treatment include, for example, cancer, e.g., melanoma, glioma or lung cancers; genetic disorders, e.g., cystic fibrosis, hemophilia or muscular dystrophy; pathogenic infections, e.g., human immunodeficiency virus, tuberculosis or hepatitis; heart disease, e.g., preventing restenosis following angioplasty or promoting angiogenesis to reperfuse necrotic tissue; and autoimmune disorders, e.g., Crohn's disease, colitis or rheumatoid arthritis.

In particular, gene therapy can be carried out in the treatment of diseases, disorders, or conditions associated with different tissues that ostensibly lack high levels of the receptor to which wild-type adenovirus fiber protein binds, and thus for which current adenoviral-mediated approaches to gene therapy are less than optimal (e.g., for delivery to monocyte/macrophages, fibroblasts, neuronal, smooth muscle, and epithelial cells). Tissues comprised of these cells (and diseases, disorders, or conditions associated therewith) include, but are not limited to: endothelia (e.g., angiogenesis, restenosis, inflammation, and tumors); neuronal tissue (e.g., tumors and Alzheimer's disease); epithelium (e.g., disorders of the skin, cornea, intestine, and lung); hematopoietic cells (e.g., human immunodeficiency virus (HIV-1, HIV-2), cancers, and anemias); smooth muscle (e.g., restenosis); and fibroblasts (e.g., inflammation).

Moreover, instead of transferring a therapeutic gene, a reporter gene, or some type of marker gene can be transferred instead using the vectors (particularly the adenoviral vectors) of the invention. Marker genes and reporter genes are of use, for instance, in cell differentiation and cell fate studies, as well as potentially for diagnostic purposes. Moreover, a standard reporter gene such as a β-galactosidase reporter gene, a gene encoding green fluorescent protein (GFP), or a β-glucuronidase gene can be used in vivo, e.g., as a means of assay in a living host, or, for instance, as a means of targeted cell ablation (see, e.g., Minden et al., BioTechniques, 20, 122–129 (1996); Youvan, Science, 268, 264 (1995); U.S. Pat. No. 5,432,081; Deonarain et al., Br. J. Cancer, 70, 786–794 (1994)).

Similarly, it may be desirable to transfer a gene to use a host essentially as a means of production in vivo of a particular protein. Along these lines, transgenic animals have been employed, for instance for the production of recombinant polypeptides in the milk of transgenic bovine species (e.g., PCT International Application WO 93/25567). Other "non-therapeutic" reasons for gene transfer include the study of human diseases using an animal model (e.g., use of transgenic mice and other transgenic animals including p53 tumor suppressor gene knockouts for tumorigenic studies, use of a transgenic model for impaired glucose tolerance and human Alzheimer's amyloid precursor protein models for the study of glucose metabolism and pathogenesis of Alzheimer's disease, respectively, etc.)

These aforementioned illustrative uses are by no means comprehensive, and it is intended that the present invention encompasses such further uses which flow from, but are not explicitly recited, in the disclosure herein. Similarly, there are numerous advantages associated with the use of the various aspects of the present invention.

For instance, use of a universal targeting vector according to the invention is advantageous inasmuch as: (1) the vector can potentially be used for all cells and tissues; (2) only one vector is required for use in all cell lines, there is no need for co-transfecting an independent vector; (3) the vector is capable of effecting gene delivery with an efficiency that is increased over that observed for vectors comprising wild-type fiber protein; (4) the vector, unlike prior vectors, does not target specific cells, but instead increases transduction efficiency in what appears to be a global fashion; (5) the vector is capable of mediating gene transfer when employed at a reduced dose (i.e., multiplicity of infection (MOI)) as compared with vector comprising wild-type fiber protein, and thus likely reduces the dosage-related drawbacks that accompany currently available adenoviral vectors; and (6) the vector can be propagated and maintained using currently available cell lines.

The ability of a universal targeting vector such as a universal targeting adenovirus vector to potentially bind to and enter all or most tissues has several advantages. These advantages include increased gene delivery efficiency to multiple tissues, the availability of a single vector capable of delivering genes to all tissues, and simplified production of necessary components for gene delivery. Moreover, such a universal targeting vector comprises a potential to deliver exogenous DNA into cells by "piggy backing" the DNA on the vector by means of a protein/DNA interaction.

Further potential advantages of such a universal targeting vector include a substantially increased efficiency of delivery (e.g., increased by 10- to 100-fold) into cells expressing low levels of fiber receptor to which wild-type fiber protein binds, as well as increased efficiency into cells or tissues expressing fiber receptor to which wild-type fiber binds. Moreover the reduced dosage at which the vectors are employed should result in a decrease in adenovirus-associated inflammation, the humoral response to adenovirus, and the cytotoxic T-lymphocyte response to adenovirus.

Furthermore, the vector is advantageous in that it can be isolated and purified by conventional means. Since changes in the vector are made at the genome level, there are no cumbersome and costly post-production modifications required, as are associated with other vectors (see, e.g., Cotten et al., supra; Wagner et al., supra). Similarly, special receptor-expressing cells lines are not required. A UTV vector can be propagated to similar titers as a wild-type vector lacking the fiber modification.

Means of Administration

The vectors and transfer vectors of the present invention can be employed to contact cells either in vitro or in vivo. According to the invention "contacting" comprises any means by which a vector is introduced intracellularly; the method is not dependent on any particular means of introduction and is not to be so construed. Means of introduction are well known to those skilled in the art, and also are exemplified herein.

Accordingly, introduction can be effected, for instance, either in vitro (e.g., in an ex vivo type method of gene therapy or in tissue culture studies) or in vivo by electroporation, transformation, transduction, conjugation or triparental mating, (co-)transfection, (co-)infection, membrane fusion with cationic lipids, high velocity bombardment with DNA-coated microprojectiles, incubation with calcium phosphate-DNA precipitate, direct microinjection into single cells, and the like. Similarly, the vectors can be introduced by means of cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., PCT patent application WO 95/21259) can be employed in the present invention. Other methods also are available and are known to those skilled in the art.

According to the invention, a "host" (and thus a "cell" from a host) encompasses any host into which a vector of the invention can be introduced, and thus encompasses an animal, including, but not limited to, an amphibian, bird, fish, insect, reptile, or mammal. Optimally a host is a mammal, for instance, rodent, primate (such as chimpanzee, monkey, ape, gorilla, orangutan, or gibbon), feline, canine, ungulate (such as ruminant or swine), as well as, in particular, human.

Inasmuch as a universal targeting vector ostensibly enters all cells, a cell can be any cell into which such a vector can enter. In particular, a universal targeting vector can be employed for gene transfer to a cell that expresses low or undetectable levels of fiber receptor, including, but not limited to, an endothelial, smooth muscle, neuronal, hematopoietic, or fibroblast cell.

One skilled in the art will appreciate that suitable methods of administering a vector (particularly an adenoviral vector) of the present invention to an animal for purposes of gene therapy (see, for example, Rosenfeld et al., *Science*, 252, 431–434 (1991); Jaffe et al., *Clin. Res.*, 39(2), 302A (1991); Rosenfeld et al., *Clin. Res.*, 39(2), 311 A (1991); Berkner, *BioTechniques*, 6, 616–629 (1988)), chemotherapy, and vaccination are available, and, although more than one route can be used for administration, a particular route can provide a more immediate and more effective reaction than another route. Pharmaceutically acceptable excipients also are well-known to those who are skilled in the art, and are readily available. The choice of excipient will be determined in part by the particular method used to administer the recombinant vector. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

A vector or transfer vector of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, a vector or transfer vector of the present invention can be made into suppositories by mixing with a variety of bases such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, the dose should be sufficient to effect a therapeutic response.

As previously indicated, a vector or a transfer vector of the present invention also has utility in vitro. Such a vector can be used as a research tool in the study of adenoviral attachment and infection of cells and in a method of assaying binding site-ligand interaction. Similarly, the recombinant coat protein comprising a nonnative amino acid sequence in addition to or in place of a native receptor binding sequence can be used in receptor-ligand assays and as adhesion proteins in vitro or in vivo, for example.

The following examples further illustrate the present invention and, of course, should not be construed as in any way limiting its scope.

EXAMPLE 1

This example describes an investigation of the levels of adenovirus receptor in different cells, as determined by the ability of wild-type adenovirus to bind to the cells.

For these experiments, the ability of adenovirus comprising wild-type fiber to bind to cells derived from various tissues was assessed. Adenovirus particles of an Ad5 strain were labeled with [$^3$H]-thymidine as previously described (see, e.g., Wickham et al., *Cell*, 73, 309–319 (1993)). Subsaturating levels of thymidine-labeled adenovirus were added to 200 µl of 10$^6$ cells preincubated about 30 to 60 minutes with or without 20 µg/ml of soluble fiber protein. The cells were incubated with the virus for 1 hour at 4° C. and then washed 3 times with cold phosphate buffered saline (PBS). The remaining cell-associated counts were measured in a scintillation counter. Specific binding was measured by subtracting the cell-associated counts (i.e., counts per minute (cpm)) in the presence of fiber from the cell-associated counts in the absence of fiber. Binding in the presence of fiber was never more than 2% of the total input of radioactive virus particles. Results were obtained as the average of triplicate measurements.

As illustrated in FIG. 1, a substantial number of the cells derived from different tissues expressed little or no fiber receptor, as indicated by a relative inability of wild-type adenovirus to bound to these cells. Cells of epithelial origin (i.e., "receptor-plus" cells including Chang, HeLa, and A549 cells) bound high levels of adenovirus. In comparison, non-epithelial cells (i.e., "receptor-minus" cells such as monocyte/macrophages, fibroblasts, neuronal, smooth muscle, and epithelial cells) exhibited about 10-fold or more reductions in virus binding as compared to epithelial-like cells.

These results confirm the previously unrecognized relative inability of adenovirus to bind to and hence enter receptor-minus non-epithelial cells, as compared with receptor-plus epithelial cells. Presumably this inability is due to the low representation of receptors for wild-type adenoviral fiber protein on these cells.

EXAMPLE 2

This example describes the construction of an adenoviral vector comprising a chimeric coat protein, particularly a chimeric adenoviral fiber protein.

To overcome the transduction limitation imposed by the presence of only a limited number of fiber receptors on clinically relevant tissues such as non-epithelial tissue, a modified adenovirus vector was constructed as depicted in FIGS. 2A and 2B to derive a vector that is referred to herein as a "universal transfer vector", or UTV. In particular, a frameshift mutation was created in a gene encoding an adenoviral coat protein, in this case, in the fiber gene. In wild-type adenovirus, the unmodified fiber gene contains a nested translational stop signal (TAA) and transcriptional polyadenylation signal (AATAAA). The polyadenylation signal directs the addition of a polyA tail onto the 3' end of the transcript. The polyA tail typically comprises anywhere from about 20 to about 200 nucleotides. Following transcription and exit from the nucleus, the TAA stop signal directs termination of translation by the ribosome.

In comparison, the modified fiber gene of a UTV vector lacks an in-frame translational "stop" signal. Following normal transcription and addition of the polyA extension onto the mRNA, in the absence of the stop codon, the ribosome continues translation of the transcript into the polyA region. Inasmuch as the codon AAA codes for the amino acid lysine, the resultant chimeric fiber gene translation product produced by a UTV contains an addition of a string of polylysine residues at the C-terminus, i.e., Lys Lys Lys Lys Lys Lys Lys Lys [SEQ ID NO:1]. It is possible that a cellular process acts to limit the length of the polylysine string, since the polylysine residues typically comprise from about 3 to about 30 residues in the chimeric fiber protein. Whatever the case, however, the polylysine protein modification, as well as further modifications described herein, allows the UTV to efficiently attach to cells lacking high levels of the receptor for wild-type adenoviral fiber protein (i.e., receptor-minus cells).

In terms of vector construction and characterization, standard molecular and genetic techniques, such as the generation of strains, plasmids, and viruses, gel electrophoresis, DNA manipulations including plasmid isolation, DNA cloning and sequencing, Western blot assays, and the like, were performed such as are known to those skilled in the art, and as are described in detail in standard laboratory manuals (e.g., Maniatis et al., *Molecular Cloning: A Laboratory Manual*, 2nd ed. (Cold Spring Harbor, N.Y., 1992); Ausubel et al., *Current Protocols in Molecular Biology*, (1987)). Restriction enzymes and other enzymes used for molecular manipulations were purchased from commercial sources (e.g., Boehringer Mannheim, Inc., Indianapolis, Ind.; New England Biolabs, Beverly, Mass.; Bethesda Research Laboratories, Bethesda, Md.), and were used according to the recommendations of the manufacturer. Cells employed for experiments (e.g., cells of the transformed human embryonic kidney cell line 293 (i.e., CRL 1573 cells) and other cells supplied by American Type Culture Collection) were cultured and maintained using standard sterile culture reagents, media and techniques, as previously described (Erzerum et al., *Nucleic Acids Research*, 21, 1607–1612 (1993)).

Accordingly, the frameshift mutation of the fiber stop codon was created by introducing a modified BamHI site (i.e., GGATCCAA [SEQ ID NO:6]) into an adenoviral transfer vector. This was done as illustrated in FIG. 3 by starting with the transfer plasmid pAd NS 83–100 (which also is known as p193NS 83–100 or pNS 83–100). pAd NS 83–100 was constructed by cloning the Ad5 NdeI to SalI fragment, which spans the 83–100 map unit region of the Ad5 genome containing the fiber gene, into the plasmid pNEB 193 (New England Biolabs, Beverly, Mass.).

The NdeI-MunI fragment of pAd NS 83–100 was replaced with a synthetic oligonucleotide comprising a BamHI site, which was flanked by a 5' NdeI site and a 3' MunI site to facilitate cloning. The double-stranded synthetic oligonucleotide fragment was created from overlapping synthetic single-stranded sense and antisense oligonucleotides, i.e., respectively, the sense primer TAT GGA GGA TCC AAT AAA GAA TCG TTT GTG TTA TGT TTC AAC GTG TTT ATT TTT C [SEQ ID NO:9], and the antisense primer AAT TGA AAA ATA AAC ACG TTG AAA CAT AAC ACA AAC GAT TCT TTA TTG GAT CCT CCA [SEQ ID NO:10], as illustrated in FIGS. 4A and 4B, respectively. The ends of the overlapping oligomers were made to have overhangs compatible for direct cloning into the NdeI and MunI sites.

The resultant transfer plasmid, pAd NS 83–100 (F) (which also is known as p193NS (ΔF) or pNS (ΔF)), lacks all but the first 50 base pairs of the coding sequence for the fiber gene (i.e., is "fiber-minus"). The vector furthermore contains the entire adenovirus E4 coding sequence. The plasmid retains the AATAAA polyadenylation signal included in the synthetic NdeI/MunI oligonucleotide, and also incorporates the new BamHI restriction site.

The mutated fiber gene was incorporated into the fiber-minus pAd NS 83–100 plasmid using synthetic sense and antisense oligonucleotide primers to amplify the fiber gene with use of the polymerase chain reaction (PCR) while incorporating a modified BamHI site following the last codon of the fiber gene to create the mutant fiber gene. This incorporated modified BamHI site also serves to code for the amino acids glycine and serine, resulting in a chimeric nucleic acid sequence of GGA TCC AAT AAA GAA TCG TTT GTG TTA TGT [SEQ ID NO:7]. The modified fiber gene thus codes for an extension to the resultant chimeric fiber protein of Gly Ser Asn Lys Glu Ser Phe Val Leu Lys Lys Lys [SEQ ID NO:4], wherein the length of the polylysine string can vary. The synthetic oligonucleotides employed for fiber amplification were the primer TCCC CCCGGG TCTAGA TTA GGA TCC TTC TTG GGC AAT GTA TGA [SEQ ID NO:1], and the primer CGT GTA TCC ATA TGA CAC AGA [SEQ ID NO:12], as illustrated in FIGS. 4C and 4D, respectively.

The amplified gene product was then cut with the restriction enzymes NdeI and BamHI, and was cloned into the NdeI/BamHI sites of the fiber-minus plasmid pAd NS 83-100 to create the transfer vector pAd NS 83–100 UTV (which also is known as p193NS (F5*), p193 (F5*), or pNS (F5*)). The entire NdeI to SalI adenovirus sequence of pAd NS 83–100 UTV was cloned into the fiber-minus plasmid pAd BS 59–100 to create pAd BS 59–100 UTV (which also is known as p193NS (F5*), p193 (F5*), or pNS (F5*).

The UTV adenovirus vector was created through homologous recombination in 293 cells. Namely, the E4+ pAd BS 59–100 UTV transfer vector was linearized with SalI, and was transfected into 293 cells that were previously infected with the adenovirus vector, A2F. The A2F vector was derived from a GV10 vector. The Ad5-based vector GV10 contains the lacZ gene under the control of the Rous sarcoma virus promoter (i.e., comprises RSV lacZ). The insertion of the reporter gene in GV10 is made within the E1 region (i.e., the vector is E1−). The GV10 vector also contains a deletion of the E3 region, but is E4+. In comparison with GV10 (i.e., RSV lacZ E1− E3− E4+), A2F further comprises a deletion of the essential E4 adenovirus genes, but is E3+ (i.e., RSV lacZ E1− E3+ E4$^1$ ).

The 293 cells contain an E1 complementing sequence, but do not contain an E4 complementing sequence. The lack of an E4 complementing sequence prevents replication of the E4− A2F vector in the 293 cell line. However, upon co-introduction of A2F virus and pAd BS 59–100 UTV in 293 cells, homologous recombination takes place between the UTV transfer vector and the A2F adenoviral genome, producing an E3+ E4+ adenovirus genome comprising a chimeric fiber protein, which is capable of replication in 293 cells. This particular resultant UTV vector was designated GV10 UTV.

The GV10 UTV vector was isolated using standard plaque isolation techniques with 293 cells. Following three successive rounds of plaque-purification, the GV10 UTV vector contained the fiber mutation and was free of any contamination by the E4− A2F vector. The presence of the chimeric fiber sequences in the GV10 UTV vector was confirmed by sequencing the fiber mRNA using reverse transcriptase-polymerase chain reaction (RT-PCR), which validated the presence of a polyadenine tail in the chimeric fiber mRNA.

Figure 5:
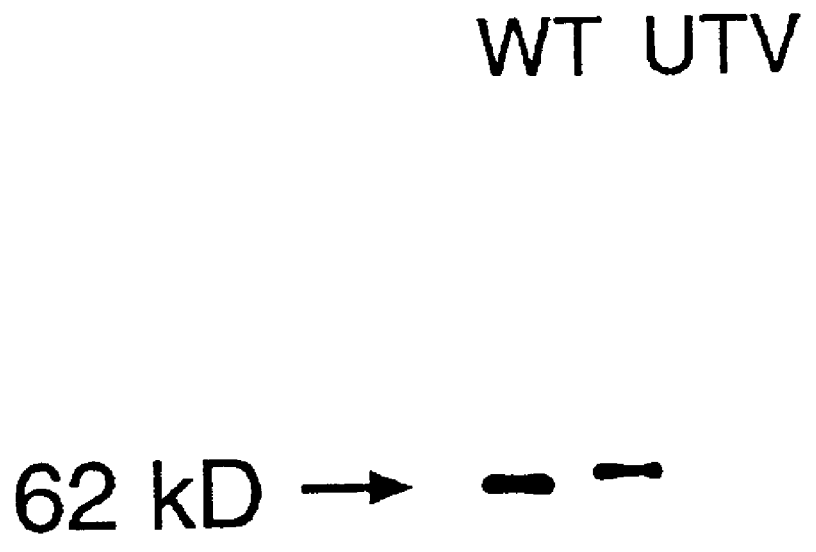

Similarly, the production of a chimeric fiber protein by the vector was confirmed by Western blot. To accomplish this, 293 cells were infected at a multiplicity of infection (MOI) of 5 with either GV10 comprising wild-type adenoviral fiber protein or with GV10 UTV comprising chimeric fiber protein. At two days post-infection, the cells were washed and then lysed in PBS by three freeze-thaw cycles. The lysates were cleared by centrifugation and loaded onto a 10% sodium dodecyl sulfate/polyacrylamide gel. Following electrophoresis, the proteins were transferred onto nitrocellulose and detected by chemiluminescence using a polyclonal antibody to fiber. The Western blot is depicted in FIG. 5. As can be seen from this figure, the migration of the proteins indicates that the chimeric UTV fiber is about 1.5 to about 2.0 kilodaltons larger than the unmodified 62 kilodalton WT fiber protein.

These results confirm that the method identified herein can be employed to introduce modifications into the fiber protein to produce a chimeric fiber protein. Similar techniques can be employed to introduce modifications into the hexon or penton proteins, or to introduce similar modifications (e.g., the addition of a string of amino acids comprised of arginine, lysine and/or histidine, or comprised of aspartate and/or glutamate, or the addition of any of these sequences into a coding region of the coat proteins).

EXAMPLE 3

This example describes the binding to cells of an adenoviral vector comprising a chimeric coat protein such as a chimeric fiber protein as compared with a wild-type adenoviral vector, either in the presence or absence of added soluble wild-type fiber protein For these experiments, the cells identified in Example 1 to which adenovirus binds with either high efficiency (i.e. receptor-plus cells) or low efficiency (i.e., receptor-minus cells) were employed. The epithelial cell line A549 was used as representative of receptor-plus cells, and the fibroblast cell line HS 68 was used as representative of receptor-minus cells. Confluent monolayers of either A549 or HS 68 cells were preincubated at 4° C. with concentrations of soluble fiber protein ranging from 0 to about 10 µg/ml. The GV10 UTV vector comprising chimeric fiber protein (UTV) or GV10 vector comprising wild-type fiber protein (WT) were labeled with tritiated thymidine as described in Example 1. About 20,000 cpm of [$^3$H]-thymidine labeled GV10 UTV or GV10 vector were then incubated with the cells for about 2 hours at 4° C. The cells were washed three times with cold PBS, and the cell-associated cpm were determined by scintillation counting. Results were obtained as the average of duplicate measurements and are presented in FIGS. 6A and 6B for the A549 and HS 68 cell lines, respectively.

Figure 6A:
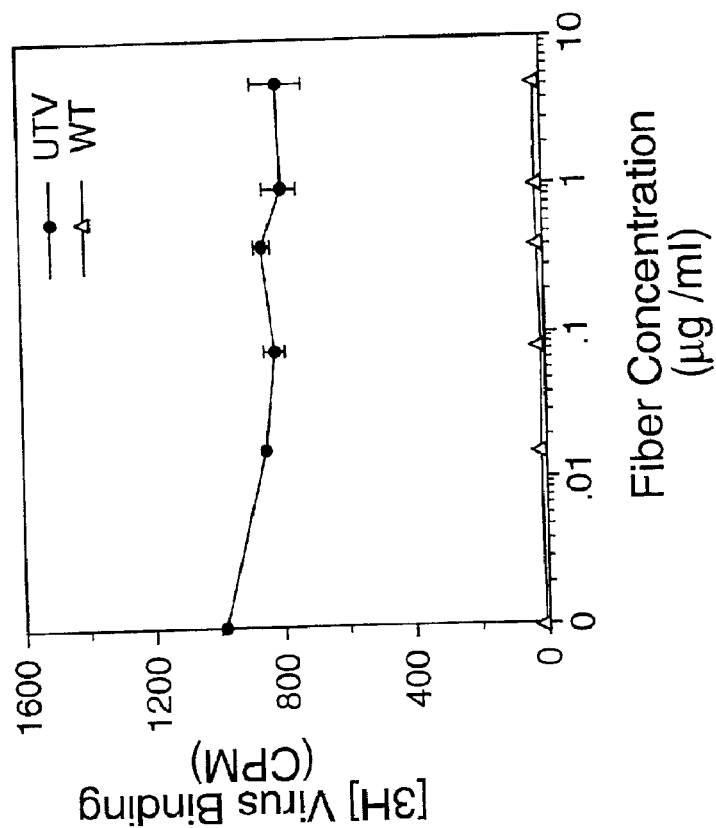
FIGS. 6A–B are graphs depicting a comparison of the binding of an adenoviral vector comprising wild-type fiber protein (i.e., GV10, open triangle) and adenoviral vector comprising chimeric fiber protein (i.e., GV10 UTV, filled circle) to a receptor-plus (A549, FIG. 6A) and a receptor-minus (HS 68, FIG. 6B) cell.
Figure 6B:
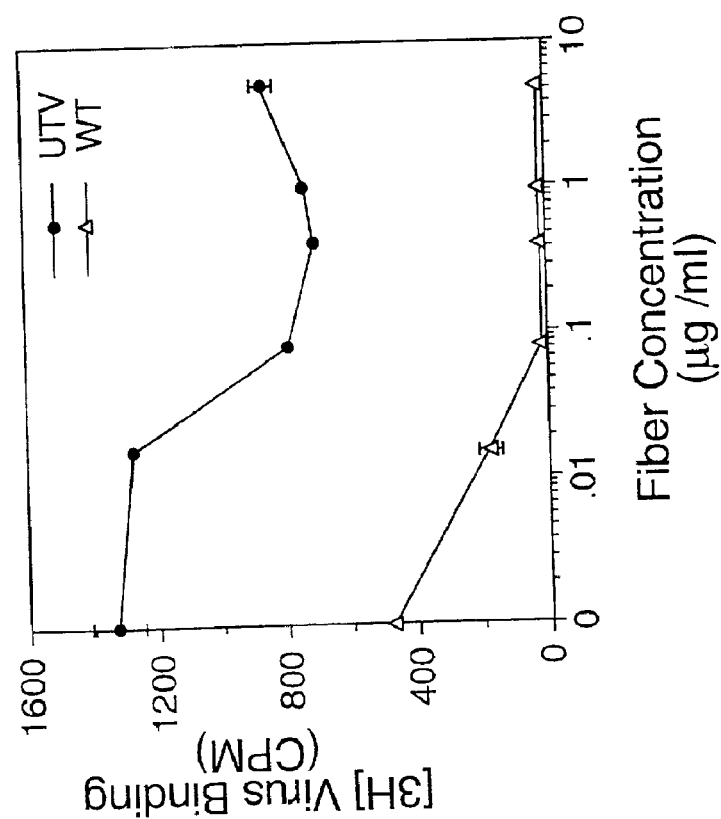

As can be seen in FIGS. 6A–B, the GV10 UTV vector chimeric fiber protein was able to bind both receptor-plus (FIG. 6A) and receptor-minus (FIG. 6B) cells with high efficiency. In comparison, the GV10 vector comprising wild-type fiber was more effective at binding to receptor-plus cells. In particular, radiolabeled GV10 UTV bound to cells expressing detectable levels of fiber receptor (i.e., A549 alveolar epithelial cells) about 2- to 2.5-fold better than GV10. Whereas all of the binding of the GV10 vector was inhibited by competing recombinant fiber protein, only about 40% of the GV10 UTV vector was inhibited by the addition of competing fiber. No detectable binding of GV10 vector comprising wild-type adenoviral fiber to HS 68 human foreskin fibroblast cells lacking fiber receptor was observed. In comparison, the GV10 UTV vector efficiently bound to HS 68 cells, and the addition of competing fiber protein had no effect on binding.

These results confirm that binding of the GV10 UTV vector comprising a chimeric coat protein (i.e., a chimeric fiber protein) does not occur via the wild-type adenoviral fiber receptor, and instead occurs via a heretofore unrecognized fiber receptor. Moreover, the results confirm that incorporation of a chimeric coat protein such as a chimeric fiber protein into an adenoviral vector results in an improved adenoviral vector. Namely, the modification comprised by the GV10 UTV vector enables it overcome the aforementioned relative inability of wild-type adenovirus to bind to receptor-minus cells, in particular, non-epithelial cells, and also allows the modified vector to bind to receptor-plus cells with an increased efficiency.

EXAMPLE 4

This example describes an investigation of the ability of various soluble factors, and inhibitors of these soluble factors, to block binding of adenovirus comprising chimeric fiber protein to receptor-minus HS 68 fibroblast cells.

For these experiments, the inhibition of GV10 UTV binding by various negatively charged molecules including salmon sperm DNA, mucin, chondroitin sulfate, and heparin, was assessed. Chondroitin sulfate and heparin are negatively charged molecules which get their charge from sulfate groups. Mucin is negatively charged due to the presence of sialic acid moieties, and DNA is negatively charged due to its incorporation of phosphate moieties. About 20,000 cpm of UTV in 250 µl of binding buffer (i.e., Dulbecco's Modified Eagle Media (D-MEM) was incubated at room temperature for about 30 minutes with concentrations of negatively charged molecules ranging from about $1\times10^{-3}$ to about $1\times10^{4}$ µg/ml. Following incubation, the mixtures were chilled on ice, and were then added to prechilled HS 68 cells plated in 24 well plates. The cells were incubated for about 1 hour, and then the cells were washed three times with PBS. Cell-associated cpm were determined by scintillation counting, and reported as the average of duplicate measurements.

Figure 7:
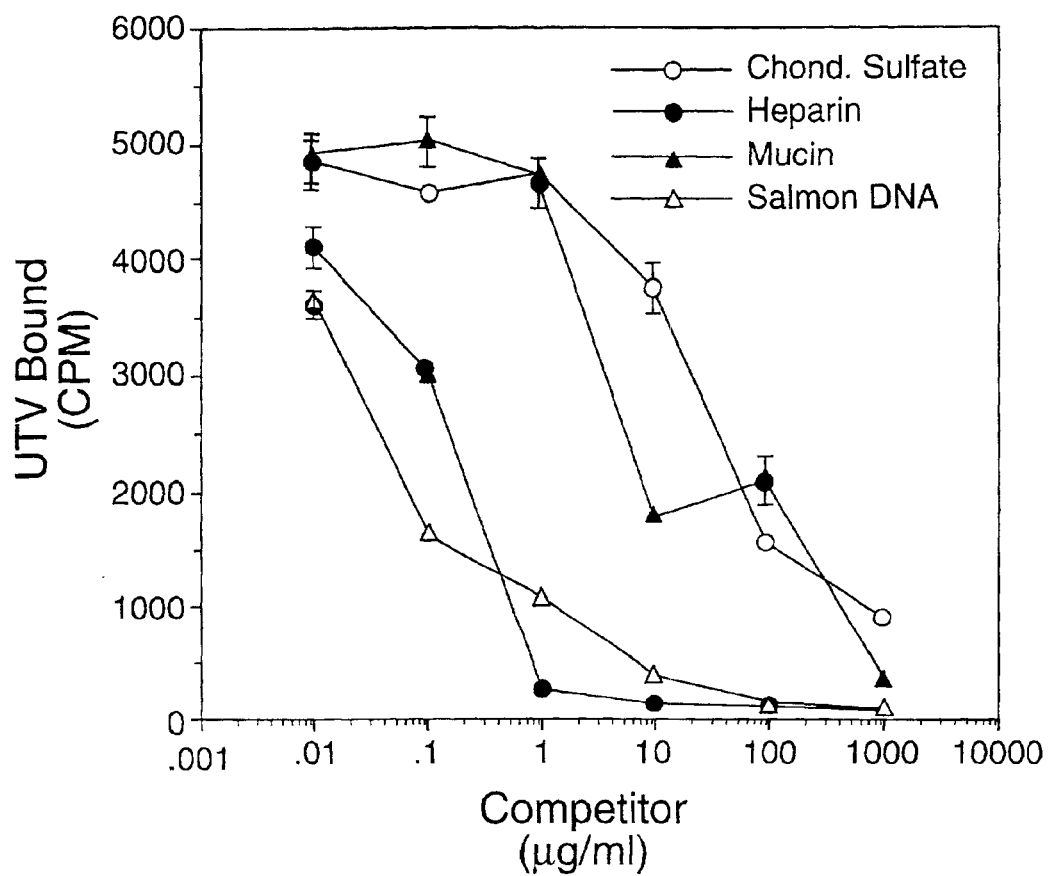
FIG. 7 is a graph of UTV bound (counts per minute (CPM)) versus amount of competitor (µg/ml) for inhibition of binding of chimeric adenoviral fiber protein to receptor-minus cells (i.e., HS 68 fibroblasts) by the soluble factors chondroitin sulfate (open circle); heparin (filled circle); mucin (filled triangle); and salmon sperm DNA (open triangle).

As indicated in FIG. 7, whereas the presence of competing wild-type fiber protein had no effect on binding of a GV10 UTV vector (i.e., comprising chimeric fiber) to HS 68 cells, negatively-charged competing molecules were able to block GV10 UTV binding. All four molecules were able to inhibit GV10 UTV binding to HS 68 cells, although heparin and DNA were most effective. These molecules have no significant effect on the binding of a GV10 vector (i.e., comprising wild-type fiber) to cells expressing high levels of fiber receptor (i.e., A549 cells; data not shown).

These results confirm that negatively charged molecules are able to block binding of the GV10 UTV vector to cells mediated by chimeric fiber protein. This inhibition presumably is due to the binding of the negatively charged molecules to the positively charged polylysine residues present on the GV10 UTV fiber. Accordingly, the impact of enzymes which cleave these negatively charged molecules on binding to cells of the GV10 UTV vector was assessed.

HS 68 cells were plated in 24 well plates, and were preincubated with the dilutions of heparinase (Sigma, St. Louis, Mo.), chondroitinase (Sigma), and sialidase (Boehringer Mannheim, Inc.) ranging from about 0.0001 to 1 for 45 minutes at 37° C., followed by 15 minutes at 4° C. Whereas chondroitinase cleaves chondroitin sulfate, heparinase cleaves heparin and heparin sulfate, and sialidase cleaves sialic acid. The initial starting concentrations for dilutions were as follows: heparinase, 25 U/ml (U=0.1 µmole/hour, pH=7.5, 25° C.); chondroitinase, 2.5 U/ml (U=1.0 µmole/minute, pH=8.0, 37° C.); and sialidase 0.25 U/ml (U=1.0 µmole/minute, pH=5.5, 37° C.). Following incubation, the cells were washed three times with cold PBS, and were then incubated with 20,000 cpm of labeled GV10 UTV vector for about 1 hour at 4° C. The cells were then washed three times with cold PBS, and the cell-associated cpm were determined by scintillation counting. The results were reported as the average of duplicate measurements.

Figure 8:
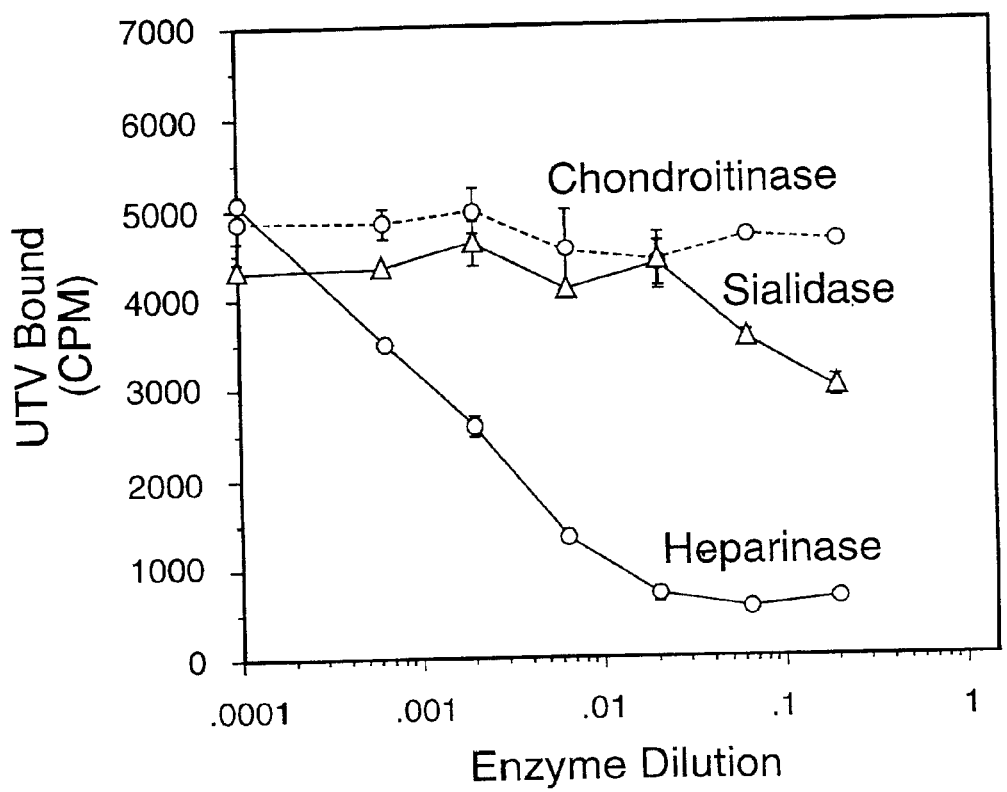
FIG. 8 is a graph of UTV bound (CPM) versus enzyme dilution for inhibition of binding of chimeric adenoviral fiber protein to receptor-minus cells (i.e., HS 68 fibroblasts) by the enzymes chondroitinase (open circles, stippled lines); heparinase (open circles, solid lines); and sialidase (triangles, solid lines).

As illustrated in FIG. 8, pretreatment of HS 68 cells with enzymes that remove negatively charged molecules from the cell surface confirms that the GV10 UTV vector comprising the chimeric fiber protein interacts with negatively charged sites on the cell surface. In particular, heparinase and sialidase were both able to reduce GV10 UTV binding, although heparinase was more effective than sialidase on HS 68 cells.

Thus, these results confirm that a vector comprising chimeric fiber protein (e.g. a GV10 UTV vector), unlike wild-type adenovirus, interacts in a novel fashion with negatively charged molecules on the cell surface to effect cell entry. These results further demonstrate that a vector comprising negatively charged residues (e.g., aspartate and glutamate) instead of positively charged molecules (e.g., lysine) similarly can be employed to bind to and effect cell entry via positively charged molecules present on the cell surface.

EXAMPLE 5

This example evaluate gene delivery to different types of cells mediated by an adenoviral vector comprising chimeric coat protein such as chimeric fiber protein (e.g., GV10 UTV) as compared to gene delivery mediated by adenovirus comprising wild-type coat protein such as fiber protein (e.g., GV10).

For these experiments, the relative levels of lacZ gene delivery by a vector containing the wild-type fiber protein (i.e., GV10) as compared with vector containing chimeric fiber protein (i.e., GV10 UTV) were compared in epithelial-like cells (i.e., HeLa, A549, HepG2 and H700 T cells), smooth muscle cells (i.e., HA SMC and HI SMC cells), endothelial cells (i.e., HUVEC and CPAE cells), fibroblast cells (i.e., HS 68 and MRC-5 cells), glioblastoma cells (i.e., U118 cells) and monocyte macrophages (i.e., THP-1 cells). Approximately $2\times10^5$ cells were inoculated one day prior to transduction by adenovirus into 24 multiwell plates. Each well was then infected at an MOI of 1 with GV10 (i.e., comprising wild-type adenoviral fiber protein) or with GV10 UTV (i.e., comprising chimeric adenoviral fiber) in a 250 µl volume for about one hour. The wells were then washed and incubated for two days, after which the lacZ activity of the cell lysates was determined. The results were reported as the average of duplicate measurements.

Figure 9:
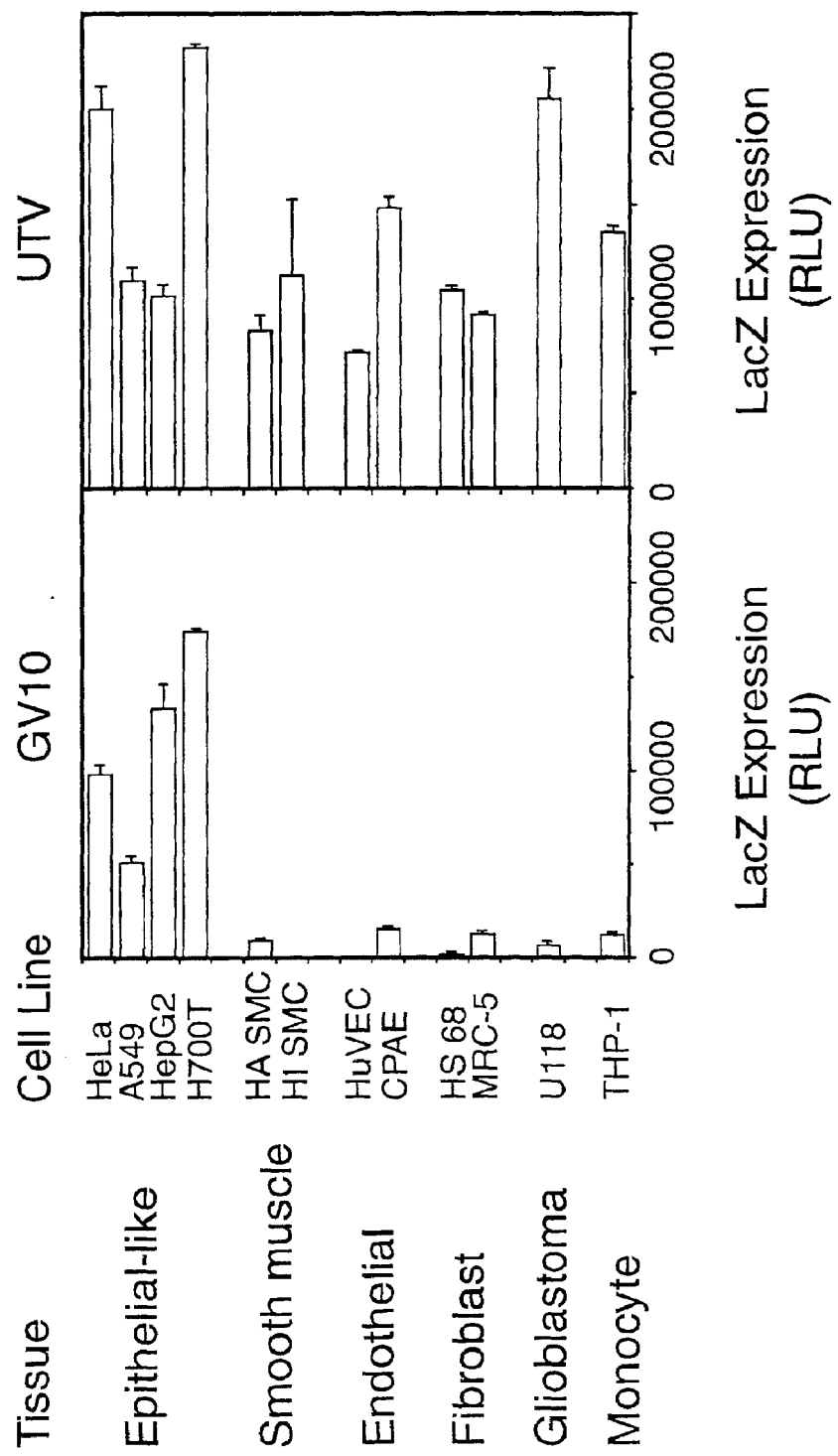
FIG. 9 is a bar graph depicting a comparison of transfer of a lacZ reporter gene by an adenoviral vector comprising wild-type fiber protein (i.e., GV10) and an adenoviral vector comprising chimeric fiber protein (i.e., GV10 UTV) as assessed by resultant reporter gene expression (i.e., relative light units (RLU)) in various receptor-plus and receptor-minus cells.

As illustrated in FIG. 9, the use of the GV10 UTV vector to transfer a reporter gene to a panel of cell lines confirms that the presence of the chimeric fiber protein (UTV) increases lacZ gene delivery to cells expressing low or undetectable levels of fiber receptor (i.e., receptor-minus cells) from about 5- to about 300-fold as compared with wild-type vector (GV10). In cells expressing high levels of the fiber receptor (i.e., receptor-plus cells), the incorporation of the chimeric fiber protein in the GV10 UTV vector results in an increase in gene delivery of up to about 3-fold.

This reduction in expression observed with transduction of receptor-minus non-epithelial cells as compared with receptor-plus epithelial cells by adenovirus comprising a wild-type fiber protein (i.e., GV10) directly correlates with the relative ability of the vector to bind these different cell types, as reported in Example 3. These results support the view that the low expression of receptors for wild-type adenovirus fiber protein is a significant limiting factor to their efficient transduction by current adenovirus vectors.

Similarly, the ability of the chimeric coat protein (i.e., chimeric fiber protein) to augment gene transfer in vivo was assessed. Three BALB/c mice were inoculated intranasally with about $1\times10^8$ pfu of GV10 in 50 µl of a saline solution comprising 10 mM MgCl₂ and 10 mM Tris (pH 7.8). Another three mice received the same dose of GV10 UTV, and two mice received the saline solution alone. The animals were sacrificed at two days post-administration, and the lungs were assayed for lacZ activity. The lungs were prepared for analysis by snap-freezing the lung in liquid nitrogen, grinding the tissue with a mortar and pestle, and lysing the ground tissue in 1.0 ml of lacZ reporter lysis buffer (Promega Corp., Madison, Wis.). A fluorometric assay was used to monitor lacZ activity, and the results of the experiments were reported as the average activity measured from each group of animals.

Figure 10:
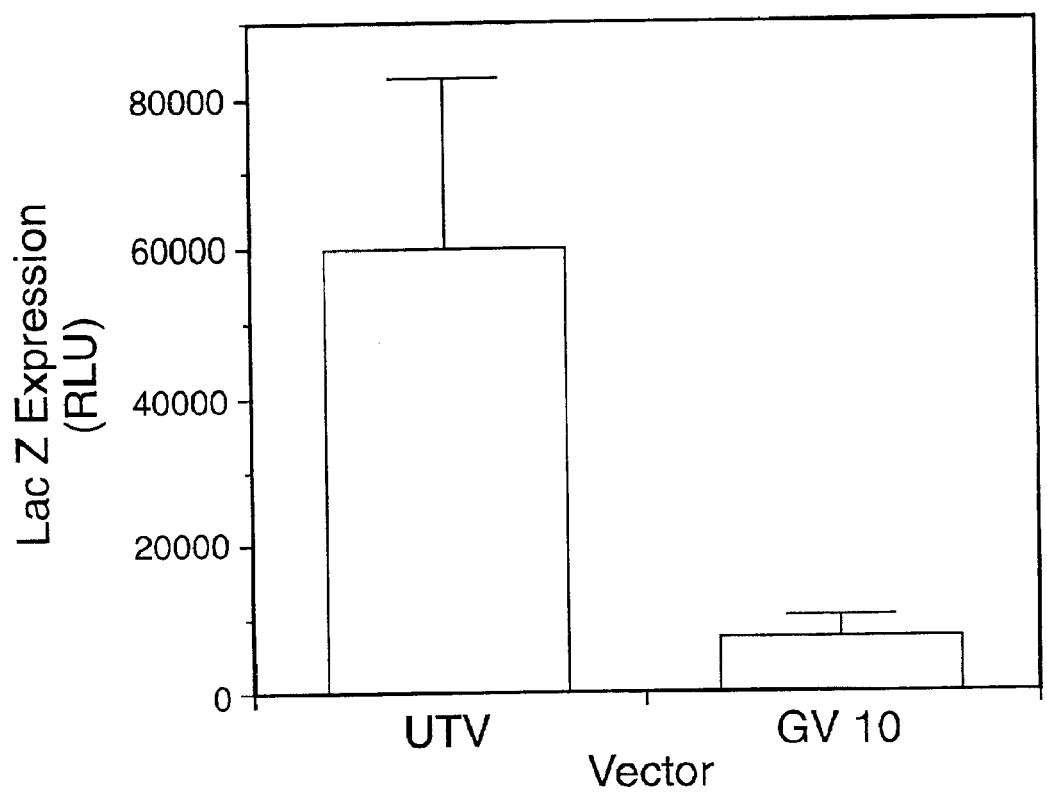
FIG. 10 is a bar graph depicting a comparison of transfer of a lacZ reporter gene by an adenoviral vector comprising wild-type fiber protein (i.e., GV10) and an adenoviral vector comprising chimeric fiber protein (i.e., GV10 UTV) as assessed by resultant reporter expression (i.e., relative light units (RLU)) in mouse lung.

The results of these experiments are illustrated in FIG. 10. As can be seen from this Figure, gene transfer in vivo mediated by the GV10 UTV vector comprising chimeric fiber protein (UTV) as compared with a vector comprising wild-type fiber protein (GV10) resulted in an average of 8-fold higher delivery to mouse lung.

These results thus confirm that incorporation of a chimeric coat protein (in this case, a chimeric fiber protein) in an adenoviral vector substantially increases the efficiency of vector-mediated gene delivery both in vitro and in vivo as compared to an adenovirus vector comprising wild-type fiber protein. Moreover, the results support the conclusion that low fiber receptor expression is a significant factor contributing to the suboptimal delivery observed in the lung and in other tissues. Also, the results confirm the superiority of the GV10 UTV vector, as well as other similar UTV vectors, over other currently available adenoviral vectors for gene transfer (e.g., delivery of the CFTR gene) to the lung and other tissues.

EXAMPLE 6

This example evaluates the ability of a vector according to the invention comprising a chimeric coat protein (e.g., a chimeric fiber protein) to interact with passenger DNA by means of a protein/DNA interaction, and to thereby carry the DNA into the cell in a "piggy-back" fashion.

For these experiments, an adenoviral vector comprising wild-type fiber (i.e., GV10) and an adenoviral vector comprising chimeric fiber (i.e., GV10 UTV) were used to assess gene transfer to receptor-plus epithelial cells (i.e., 293, A549, and H700 T cells). In control experiments, the cells were transduced with the vectors as previously described. In the experimental condition, the vectors were incubated with the plasmid pGUS, which comprises a β-glucuronidase reporter gene, such that the chimeric adenoviral fiber protein was able to complex with the plasmid DNA. Specifically, about 5×10⁷ active particles (i.e., fluorescence focus units (ffu)) of GV10 or GV10 UTV were incubated for 1 hour with about 2.5 μg of plasmid pGUS DNA. The mixture was then added to about 2×10⁵ of the indicated cells in 250 μl of DMEM containing 10% fetal bovine serum. Both β-glucuronidase and β-galactosidase activity were then assessed by fluorometric assay at 10 days post-transduction. β-glucuronidase expression in cells was monitored similarly to the β-galactosidase assay for lacZ expression, by monitoring the generation of a blue color when β-glucuronidase catalyzes a reaction with the substrate X-glu.

Figure 11:
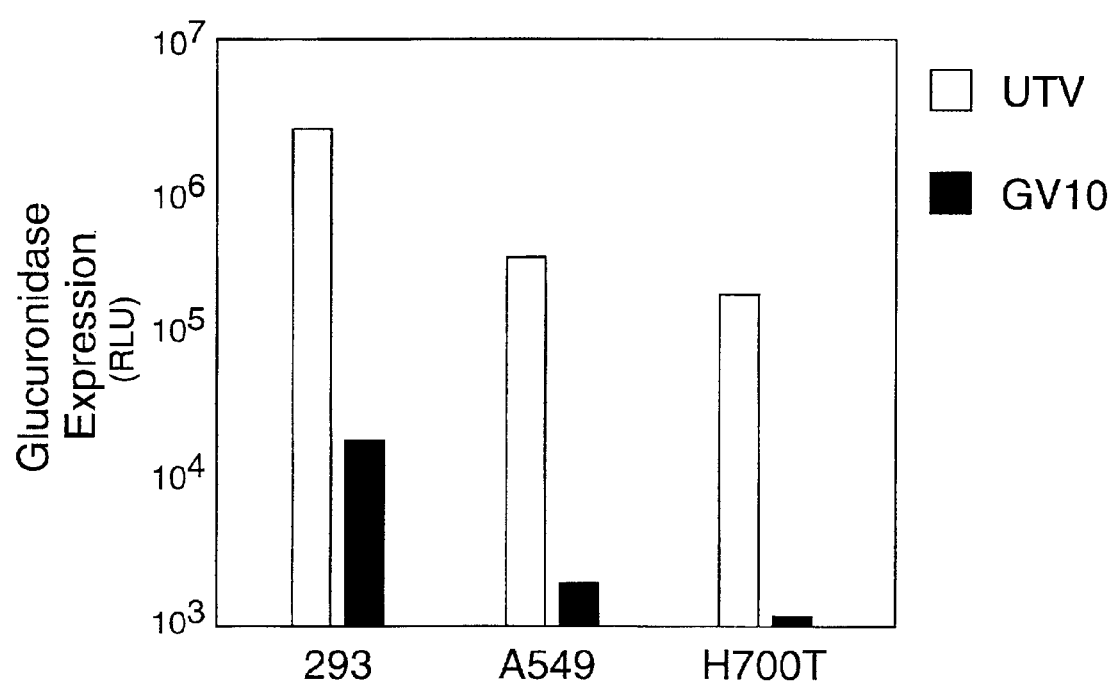
FIG. 11 is a bar graph depicting the transfer of a reporter gene (i.e., contained in pGUS) by an adenoviral vector comprising wild-type fiber protein (i.e., GV10, solid bars) and an adenoviral vector comprising chimeric fiber (i.e., GV10 UTV, open bars) potentially bound via a protein/DNA interaction into 293 cells, A549 cells, and H700 T cells.

The results of these experiments are illustrated in FIG. 11. Comparable levels of lacZ expression were obtained when either a GV10 vector (i.e. comprising wild-type fiber protein) or a GV10 UTV vector (i.e. comprising chimeric fiber protein) were employed to transfer the reporter gene in cis to epithelial cells. In comparison, the wild-type vector was able to transfer intracellularly the plasmid pGUS at only a relatively low level in all epithelial cells, as assessed by β-glucuronidase gene expression. This basal level of gene transfer likely was accomplished by means of receptor-mediated uptake (RME) of bystander molecules, as previously described (PCT patent application WO 95/21259). However, with use of a GV10 UTV vector comprising a chimeric fiber protein, transfer of the pGUS plasmid was substantially increased. In the case of gene transfer to 293 cells, pGUS plasmid-directed β-glucuronidase expression exceeded expression observed following GV10 UTV-vector mediated transfer of a cis-linked reporter gene.

These results confirm that a vector comprising a chimeric coat protein such as a chimeric fiber protein according to the invention demonstrates increased transfer of a nucleic acid that is not located in cis with the vector. Ostensibly, this enhanced gene transfer is effected by the occurrence of a protein/DNA interaction between the negatively charged residues on the chimeric fiber (e.g., residues of the polylysine string), resulting in binding to the vector of the nucleic acid; however, other means of enhancement also are possible.

EXAMPLE 7

This example describes the construction of further plasmids containing UTV or UTV-like sequences in the C-terminus of the fiber protein.

Figure 12:
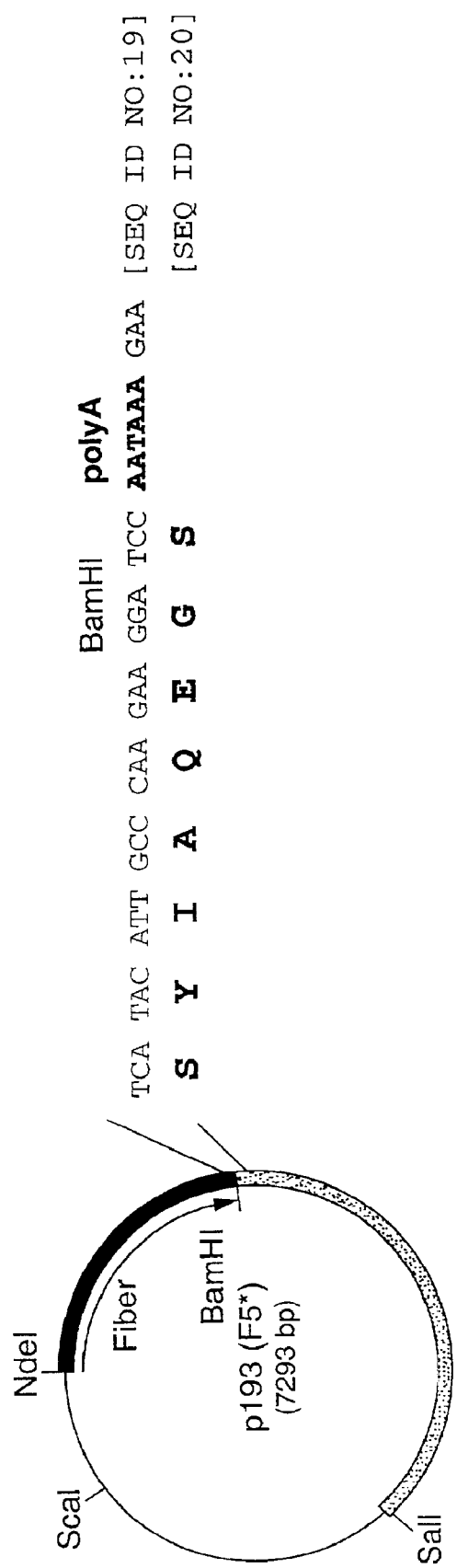
FIG. 12 is a diagram that further depicts the plasmid p193 (F5*) (described as pAd NS 83–100 UTV in FIG. 3, and also known as p193 (F5*) or pNS (F5*)) used to construct adenovirus fiber chimeras, and the sequence of the C-terminus of the mutated fiber protein present in the plasmid (polyadenylation site emboldened).
Figure 13:
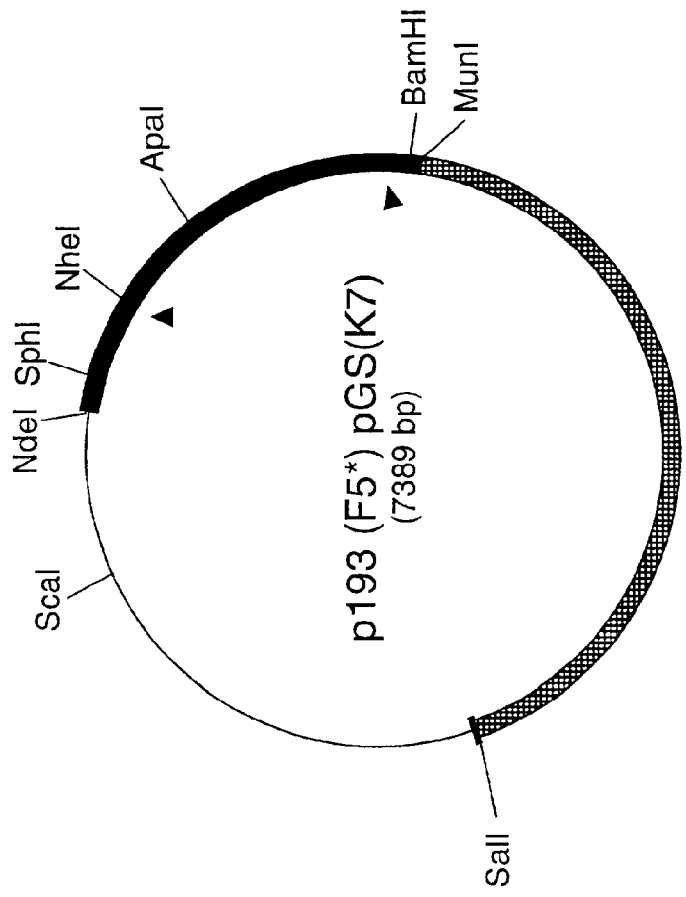
FIG. 13 is a diagram that depicts plasmid p193NS (F5*) pGS(K7) (also known as p193 (F5*) pGS(K7) or pNS (F5*) pK7) used to construct adenovirus fiber chimeras.

The transfer plasmid, p193(F5*) (FIG. 12; also known as p193NS (F5*), pNS (F5*), and pAd NS 83–100 UTV) described in Example 2 was employed as a starting point for the construction of these further plasmids containing chimeric adenovirus fiber proteins. As depicted in FIG. 12, p193 (F5*) contains a mutated fiber gene with a BamHI site between the last fiber protein codon and the frameshifted fiber protein stop codon. The further mutant transfer plasmids constructed as described herein contain sequences in the fiber C-terminus encoding an amino acid glycine/serine repeat linker, a targeting sequence, and a stop codon. These plasmids were made by cloning synthetic oligonucleotides into the BamHI site of p193(F5*) to create the transfer plasmid p193NS (F5*) pGS(K7)(also known as p193 (F5*) pGS(K7) or pNS (F5*) pK7) depicted in FIG. 13.

Thus, the sequence of the wild-type Ad5 fiber gene is:

TCA TAC ATT GCC CAA GAA TAA AAA AGAA [SEQ ID NO:59]

Ser Tyr Ile Ala Gln Glu  [SEQ ID NO:60]

wherein "TAA" is a termination codon, and the polyadenylation sequence is emboldened. The C-terminus of the mutated fiber gene present in p193(F5*) is:

[SEQ ID NO:19]
TCA TAC ATT GCC CAA GAA <u>GGA TCC</u> AATAAA GAA

[SEQ ID NO:20]
Ser Tyr Ile Ala Gln Glu Gly Ser wherein the underlined sequence indicates the mutated BamHI site introduced into the fiber protein, and the polyadenylation sequence is emboldened. In comparison, the amino acid sequence of the C-terminus of the fiber gene present in p193NS (F5*) pGS(K7) is:

<u>G S</u> G S G S G S G S KKKKKKK  [SEQ ID NO:22]

wherein the underlined sequence indicates the mutated BamHI site introduced into the fiber protein, and the emboldened sequence indicates the polylysine string added to the C-terminus. This amino acid sequence is encoded by the nucleic acid sequence: GGA TCA GGA TCA GGT TCA GGG AGT GGC TCT AAA AAG AAG AAA AAG AAG AAG TAA [SEQ ID NO:21], wherein "TAA" is a termination codon.

The overlapping synthetic oligonucleotides used to make the transfer plasmid p193NS (F5*) pGS(K7) were: pK7s (sense), GA TCA GGA TCA GGT TCA GGG AGT GGC TCT AAA AAG AAG AAA AAG AAG AAA TAA G [SEQ ID NO:61]; pK7a (antisense), GA TCC TTA CTT CTT CTT TTT CTT CTT TTT AGA GCC ACT CCC TGA ACC TGA TCC T [SEQ ID NO:62]. The sense and antisense oligonucleotides were mixed in equimolar ratios and cloned into the BamHI site of p193NS (F5*) to create p193NS (F5*) pGS(pK7). Verification of the correctly-oriented insert in p193NS (F5*) pGS(pK7) was performed by PCR using the pK7s sense primer and the downstream antisense oligonucleotide primer A5a32938, CAGGTTGAATAC-TAGGGTTCT [SEQ ID NO:63]. The plasmid was also verified to contain the correctly oriented insert by sequencing the DNA sequence in the region of the insert using the A5a32938 primer.

The transfer plasmid p193NS (F5*) was employed in the construction of further mutant transfer plasmids that additionally contain a UTV or UTV-like cell targeting sequence in the C-terminus of the fiber protein. These plasmids include p193NS (F5*) pGS(null) (also known as p193 (F5*) pGS(null) or p193 (F5*) pGS), pBSS 75–100 pGS (null), pBSS 75–100 pGS(RK32), pBSS 75–100 pGS(RK33), and pBSS 75–100 pGS(tat).

To construct p193NS (F5*) pGS(null), the complementary overlapping oligonucleotides pGSs, GATCCGGT-TCAGGATCTGGCAGTGGCTCGACTAGTTAAA [SEQ ID NO:64], and pGSa, GATCTTTAACTAGTCGAGC-CACTGCCAGATCCTGAACCG [SEQ ID NO:65] were constructed for direct ligation into the BamHI-digested p193NS (F5*) plasmid. Verification of the correctly-oriented clone was performed by PCR using the pGSs primer and the downstream antisense oligonucleotide primer A5a32938. The plasmid was also verified to contain the correctly oriented insert by sequencing the DNA sequence in the region of the insert using the A5a32938 primer.

Figure 14:
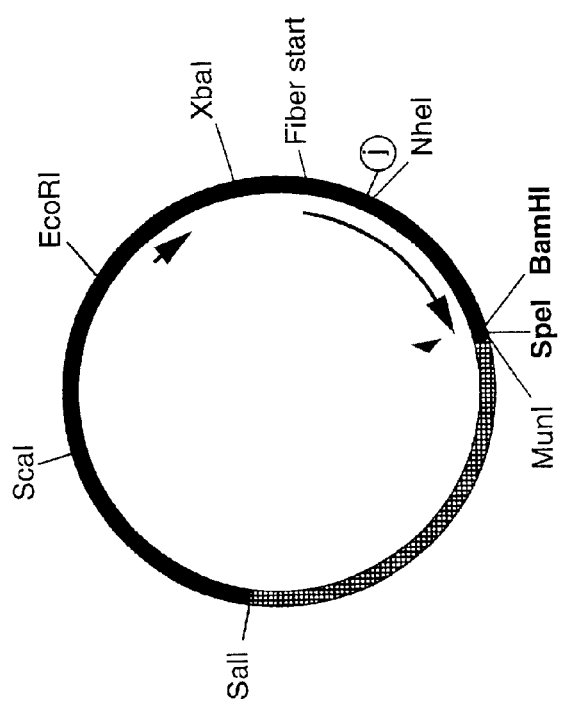
FIG. 14 is a diagram that depicts plasmid pBSS 75–100 pGS(null) (also known as pBSS 75–100 ΔE3 pGS(null)).

The vector pBSS 75–100 pGS(null) (also known as pBSS 75–100 ΔE3 pGS(null)) depicted in FIG. 14 was constructed by replacing the NheI to SalI fragment from pBSS 75–100 with the corresponding fragment from p193NS (F5*) pGS (null). The SpeI site that is not within the fiber chimera gene was then eliminated by partially restricting the plasmid with SpeI, filling in with Klenow fragment and then religating the vector. The resultant vector comprises the relevant nucleic acid sequence: GCCCAAGAAGGATCCGGTTCAG-GATCTGGCAGTGGCTCGACTAGTTAA [SEQ ID NO:23] (wherein "TAA" is a termination codon), which codes for the amino acid sequence Ala Gln Glu Gly Ser Gly Ser Gly Ser Gly Ser Gly Ser Thr Ser [SEQ ID NO:24].

Figure 15:
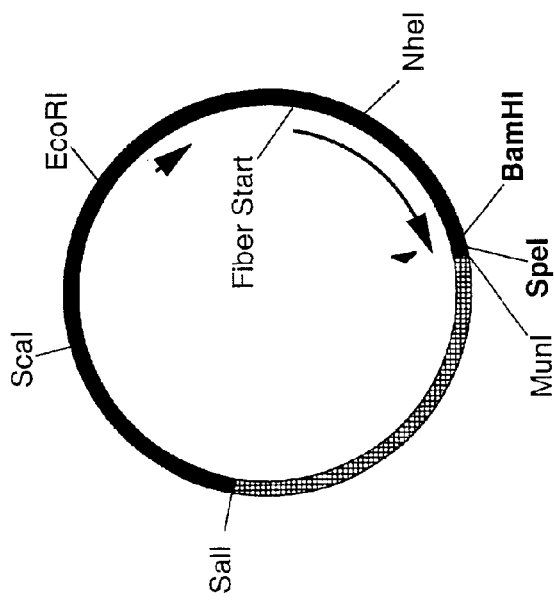
FIG. 15 is a diagram that depicts plasmid pBSS 75–100 pGS(RK32) (also known as pBSS 75–100 ΔE3 pGS(RKKK)₂ or pBSS 75–100 ΔE3 pGS(RKKK2)).

The inserts of plasmids pBSS 75–100 pGS(RK32) (also known as pBSS 75–100 ΔE3 pGS(RKKK)$_2$ or pBSS 75–100 ΔE3 pGS(RKKK2)), pBSS 75–100 pGS(RK33) (also known as pBSS 75–100 ΔE3 pGS(RKKK)$_3$ or pBSS 75–100 ΔE3 pGS(RKKK3)), and pBSS 75–100 pGS(tat), were constructed for direct ligation into the SpeI-digested pBSS 75–100 pGS(null) plasmid. To construct pBSS 75–100 pGS (RK32) depicted in FIG. 15, the complementary overlapping oligonucleotides, RK32s, CTAGAAAGAAGAAACG-CAAAAAGAAGA [SEQ ID NO:66] and RK32a, CTAGTCTTCTTTTGCGTTTCTTCTTT [SEQ ID NO:67] were employed. The resultant vector comprises the relevant nucleic acid sequence: GCCCAAGAAGGATCCG-GTTCAGGATCTGGCAGTGGCTCGACTA-GAAAGAAGAA ACGCAAAAAGAAGACTAGTTAA [SEQ ID NO:25] (wherein "TAA" is a termination codon), which codes for the amino acid sequence Ala Gln Glu Gly Ser Gly Ser Gly Ser Gly Ser Gly Ser Thr Arg Lys Lys Lys Arg Lys Lys Lys Thr Ser [SEQ ID NO:26].

Figure 16:
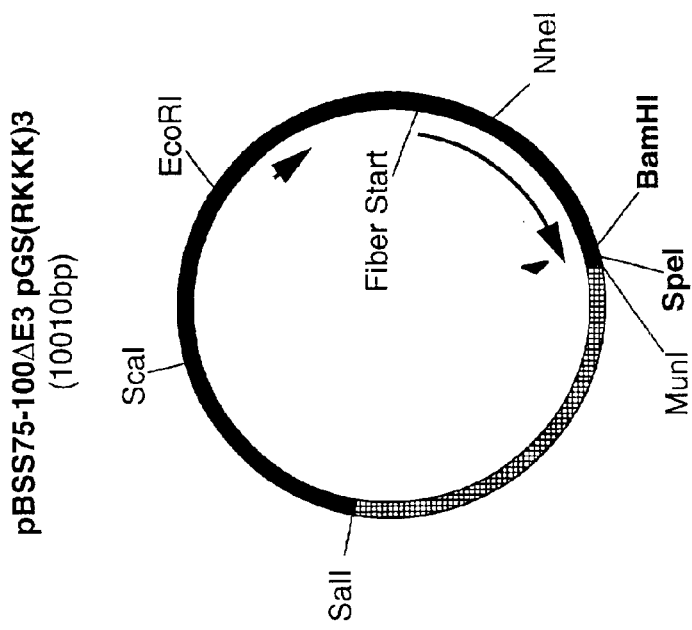
FIG. 16 is a diagram that depicts plasmid pBSS 75–100 pGS(RK33) (also known as pBSS 75–100 ΔE3 pGS(RKKK)₃ or pBSS 75–100 ΔE3 pGS(RKKK3)).
Figure 17:
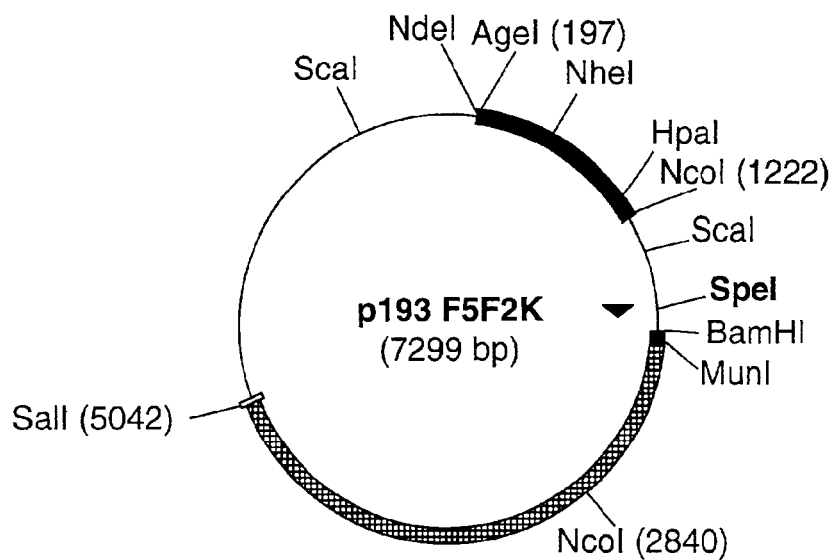
FIG. 17 is a diagram that depicts plasmid p193NS F5F2K (also known as p193 F5F2K).

To construct pBSS 75–100 pGS(RK33) depicted in FIG. 16, the complementary overlapping oligonucleotides, RK33s, CTAGAAAGAAGAAGCGCAAAAAAAAA-GAAAGAAGAAGA [SEQ ID NO:68] and RK33a, CTAGTCTTCTTCTTTCTTTTTTTTTGCGCTTCTTC-TTCTTT [SEQ ID NO:69], were employed. The resultant vector comprises the relevant nucleic acid sequence: GCCCAAGAAGGATCCGGTTCAGGATCTG-GCAGTGGCTCGACTAGAAAGAAGAAGCG-CAAAAAAAAAGAAAGAAGAAGACTAGTTAA [SEQ ID NO:27] (wherein "TAA" is a termination codon), which codes for the amino acid sequence Ala Gln Glu Gly Ser Gly Ser Gly Ser Gly Ser Gly Ser Thr Arg Lys Lys Lys Arg Lys Lys Lys Arg Lys Lys Lys Thr Ser [SEQ ID NO:28].

To construct pBSS 75–100 pGS(tat) the complementary overlapping oligonucleotides, TATs, CT AGT TAT GGG AGA AAA AAG CGC AGG CAA CGA AGA CGG GCA T [SEQ ID NO:70] and TATa, CT AGA TGC CCG TCT TCG TTG CCT GCG CTT TTT TCT CCC ATA A [SEQ ID NO:71] were employed. The resultant vector comprises the relevant nucleic acid sequence: ACT AGT TAT GGG AGA AAA AAG CGC AGG CAA CGA AGA CGG GCA TCT AGT [SEQ ID NO:72], which codes for the amino acid sequence Thr Ser Tyr Gly Arg Lys Lys Arg Arg Gln Arg Arg Arg Ala Ser Ser [SEQ ID NO:73].

Verification of the correctly-oriented clone was performed by PCR using the sense primers (RK32s, RK33s, or TATs) for each of the three respective plasmids, and using the downstream antisense oligonucleotide primer A5a32938. Each of the plasmids also were verified to contain the correctly-oriented insert by sequencing the DNA sequence in the region of the insert using the A5a32938 primer.

Example 8

This example described the construction of plasmids containing UTV domains in the fiber loop.

Plasmids containing a UTV sequence (and/or a spacer sequence) in an exposed loop of the fiber protein are constructed by incorporating any of the aforesaid sequences (as well as any further UTV-like sequences) into the fiber protein. This is accomplished making use of the plasmid transfer vector p193NS (F5*) to construct the further transfer vector p193NS F5F2K (also called p193 F5F2K) depicted in FIG. 17. Plasmid p193NS F5F2K contains a unique Spe I restriction site within the Ad2 fiber gene encoding an exposed loop in the protein. Namely, the fiber gene present in p193NS F5F2K comprises the fiber sequence:

```
ATT ACA CTT AAT GGC ACT AGT GAA TCC    [SEQ ID NO:29]
Ile Thr Leu Asn Gly Thr Ser Glu Ser    [SEQ ID NO:30]
ACA GAA ACT
Thr Glu Thr
``` wherein the underlined sequence indicates the novel Spe I site introduced into the fiber gene.

This vector was then used to clone targeting sequences into the Spe I site. In particular, a nucleic acid sequence encoding the stretch of 8 basic amino acids RKKKRKKK (Arg Lys Lys Lys Arg Lys Lys Lys [SEQ ID NO:74]) comprising the heparin binding domain were cloned into the Spe I site of p193 F5F2K using overlapping sense and antisense oligonucleotides.

Namely, the (RKKK)₂ sequence comprises, in part, the sequence:

TCT AGA AAA AAA AAA CGC AAG AAG AAG    [SEQ ID NO:75]

Thr Arg Lys Lys Lys Arg Lys Lys Lys    [SEQ ID NO:76]

ACT AGT

Thr Ser.

Figure 18:
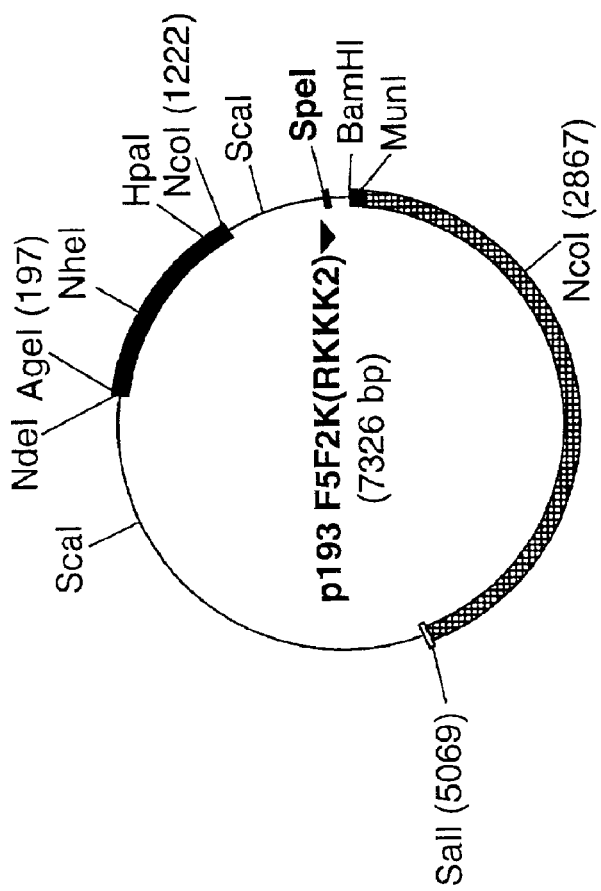
FIG. 18 is a diagram that depicts plasmid p193NS F5F2K (RKKK)₂ (also known as p193NS F5F2K(RKKK2), p193NS F5F2K(RK32), or p193 F5F2K(RKKK2)).

The 27-mer sense oligonucleotide RK32s and 27-mer antisense oligonucleotide RK32a described in Example 7 were employed for cloning the PolyGS(RKKK)₂ sequence comprising the RKKKRKKK [SEQ ID NO:74] peptide motif. The p193NS F5F2K(RKKK)₂ plasmid was constructed by cloning the DNA sequence encoding the binding domain into the Spe I site of p193NS F5FK2. The overlapping sense and antisense oligonucleotides encoding the binding domain were first annealed and then directly ligated into the Spe I restriction site to result in the plasmid p193NS F5F2K(RKKK)₂ depicted in FIG. 18. This plasmid also is known as p193NS F5F2K(RKKK2), p193NS F5F2K (RK32), or p193 F5F2K(RKKK2). The relevant portion of the modified loop of the fiber knob present in p193NS F5F2K(RKKK)₂ is:

ATT ACA CTT AAT GGC ACT AGA AAG AAG    [SEQ ID NO:31]

Ile Thr Leu Asn Gly Thr Arg Lys Lys    [SEQ ID NO:32]

AAA CGC AAA AAG AAG ACT AGT GAA TCC

Lys Arg Lys Lys Lys Thr Ser Glu Ser

ACA GAA ACT

Thr Glu Thr.

Furthermore, a (RKKK)₃ sequence, or other variations of this sequence, can be inserted into p193NS F5F2K. This sequence comprises, in part:

TCT AGA AAG AAG AAG CGC AAA AAA AAA    [SEQ ID NO:77]

Thr Arg Lys Lys Lys Arg Lys Lys Lys    [SEQ ID NO:78]

AGA AAG AAG AAG ACT AGT

Arg Lys Lys Lys Thr Ser.

Figure 19:
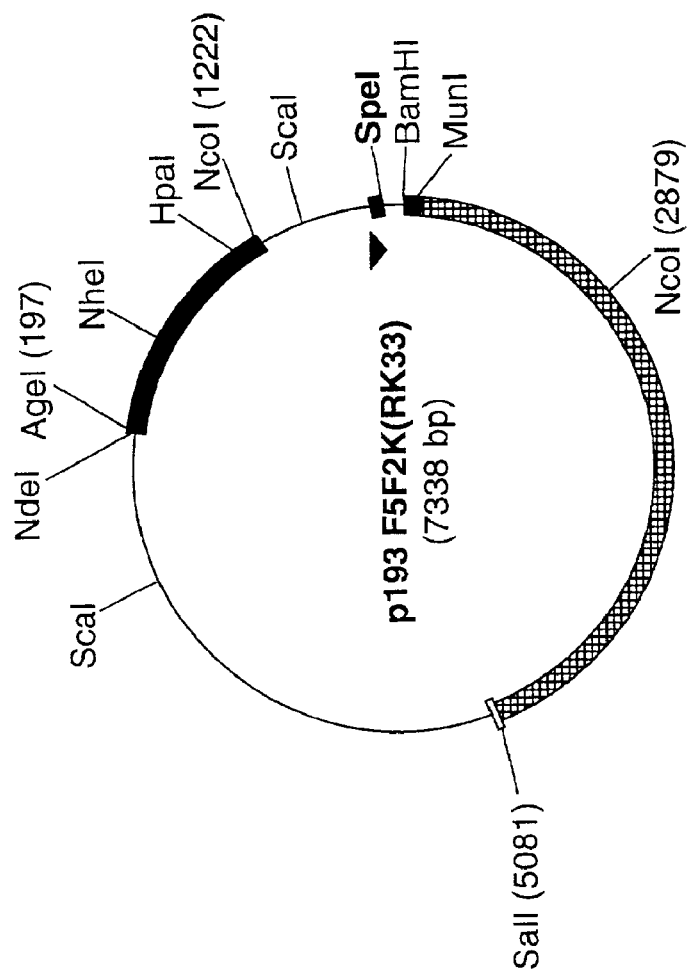
FIG. 19 is a diagram that depicts plasmid p193NS F5F2K (RKKK)₃ (also known as p193NS F5F2K(RKKK3), p193 F5F2K(RKKK3), or p193 F5FK(RK33)).

The sequence can be inserted with use of the 39-mer sense oligonucleotide (RKKK)₃(S) (i.e., comprising the sequence CT AGA AAG AAG AAG CGC AAA AAA AAA AGA AAG AAG AAG A [SEQ ID NO:79]), and the 39-mer antisense oligonucleotide (RKKK)₃(a) (i.e., comprising the sequence CT AGT CTT CTT CTT TCT TTT TTT TTT GCG CTT CTT CTT T [SEQ ID NO:80]). The resultant plasmid p193NS F5F2K(RKKK)₃ is depicted in FIG. 19. This plasmid also is known as p193NS F5F2K(RKKK3), p193 F5F2K(RKKK3), or p193 F5FK(RK33). The relevant portion of the modified loop of the fiber knob present in p193 F5F2K(RKKK)₃ is:

CTT AAT GGC ACT AGA AAG AAG AAG CGC    [SEQ ID NO:33]

Leu Asn Gly Thr Arg Lys Lys Lys Arg    [SEQ ID NO:34]

AAA AAA AAA AGA AAG AAG ACT AGT GAA

Lys Lys Lys Arg Lys Lys Thr Ser Glu

TCC ACA

Ser Thr.

EXAMPLE 9

This example describes the construction of plasmids containing chimeric penton base proteins comprising UTV or UTV-like sequences.

The transfer plasmid pACT (ΔRGD) (also described as plasmid pAT in U.S. Pat. No. 5,559,099) was derived, in part, by manipulating a plasmid containing the unique BamHI/PmeI fragment (13259–21561) of the Ad5 genome, and contains, among other things, a penton base protein comprising a deletion of 8 amino acids constituting the α$_v$ integrin binding domain, and a substitution of the deleted region for amino acids constituting a unique SpeI site, for the convenient insertion of exogenous sequences.

Figure 20:
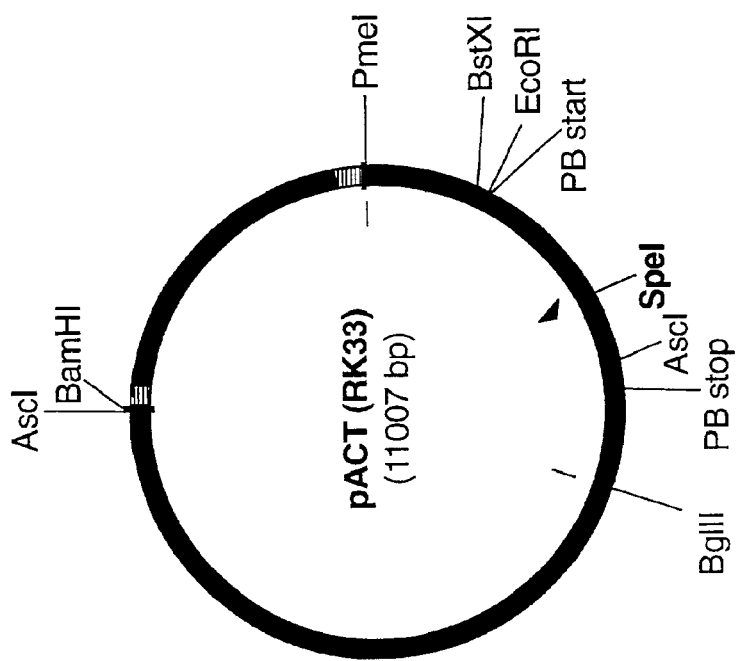
FIG. 20 is a diagram that depicts plasmid pACT (RKKK)₃ (also known as pACT (RKKK3) or pACT (RK33)).

To construct plasmid pACT (RKKK)₃ (also known as pACT (RKKK3) or pACT (RK33)) depicted in FIG. 20, the complementary overlapping oligonucleotides RK33s and RK33a were directly ligated into a SpeI-digested pACT (ΔRGD) plasmid. Verification of the correctly-oriented clone was performed by PCR using the RK33a primer for the plasmid and the upstream sense oligonucleotide primer A5s15002. The plasmid also was verified to contain the correctly oriented insert by sequencing the DNA sequence in the region of the insert using the A5s15002 primer. The relevant portion of the UTV domain that will result in the chimeric penton base protein in pACT (RKKK)₃ is:

AAC GAT ACT AGA AAG AAG AAG CGC AAA    [SEQ ID NO:35]

Asn Asp Thr Arg Lys Lys Lys Arg Lys    [SEQ ID NO:36]

AAA AAA AGA AAG AAG AAG ACT AGT GCC

Lys Lys Arg Lys Lys Lys Thr Ser Ala

ACA

Thr.

Figure 21:
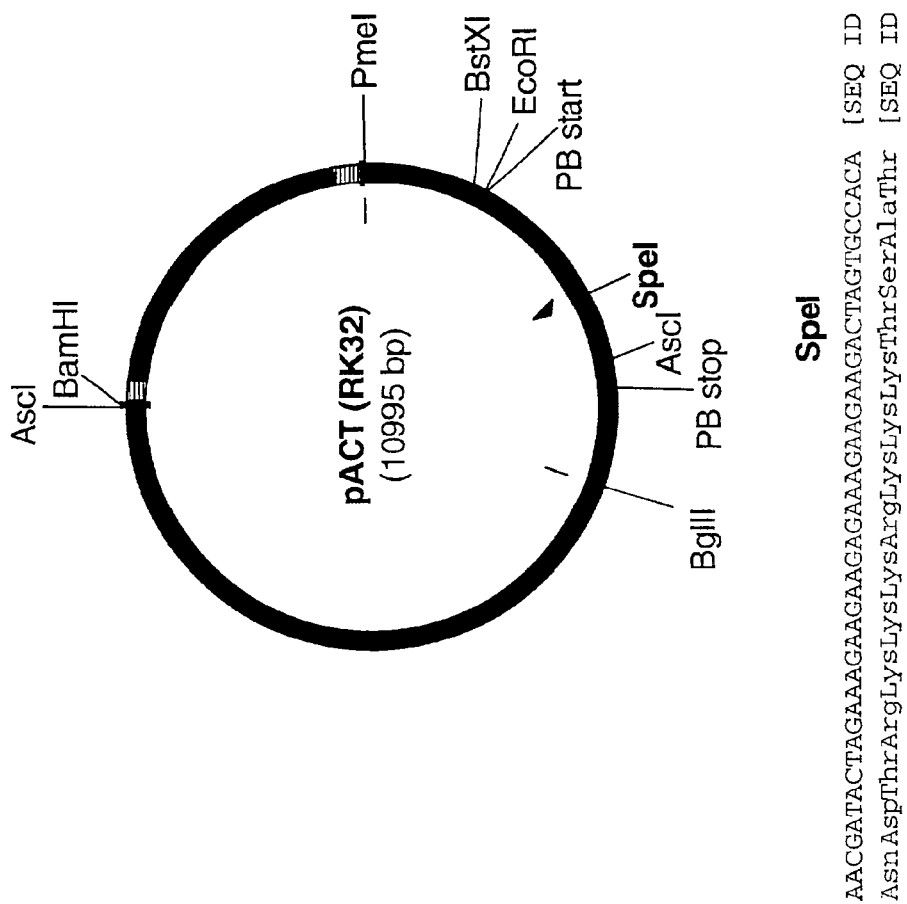
FIG. 21 is a diagram that depicts plasmid pACT (RKKK)₂ (also known as pACT (RKKK2) or pACT (RK32)).

The plasmid pACT (RK32) (which also can be called pACT (RKKK2) or pACT (RKKK)₂) depicted in FIG. 21 similarly can be constructed using the RK32s and RK32a overlapping primers. The relevant portion of the UTV domain present in the chimeric penton base protein in pACT (RKKK)₂ is:

AAC GAT ACT AGA AAG AAG AAG AGA AAG    [SEQ ID NO:37]

Asn Asp Thr Arg Lys Lys Lys Arg Lys    [SEQ ID NO:38]

AAG AAG ACT AGT GCC ACA

Lys Lys Thr Ser Ala Thr.

EXAMPLE 10

This example describes the construction of plasmids containing UTV or UTV-like sequences in the adenovirus hexon protein, and particularly which contain these sequences in an exposed loop of the adenovirus hexon protein.

Figure 22:
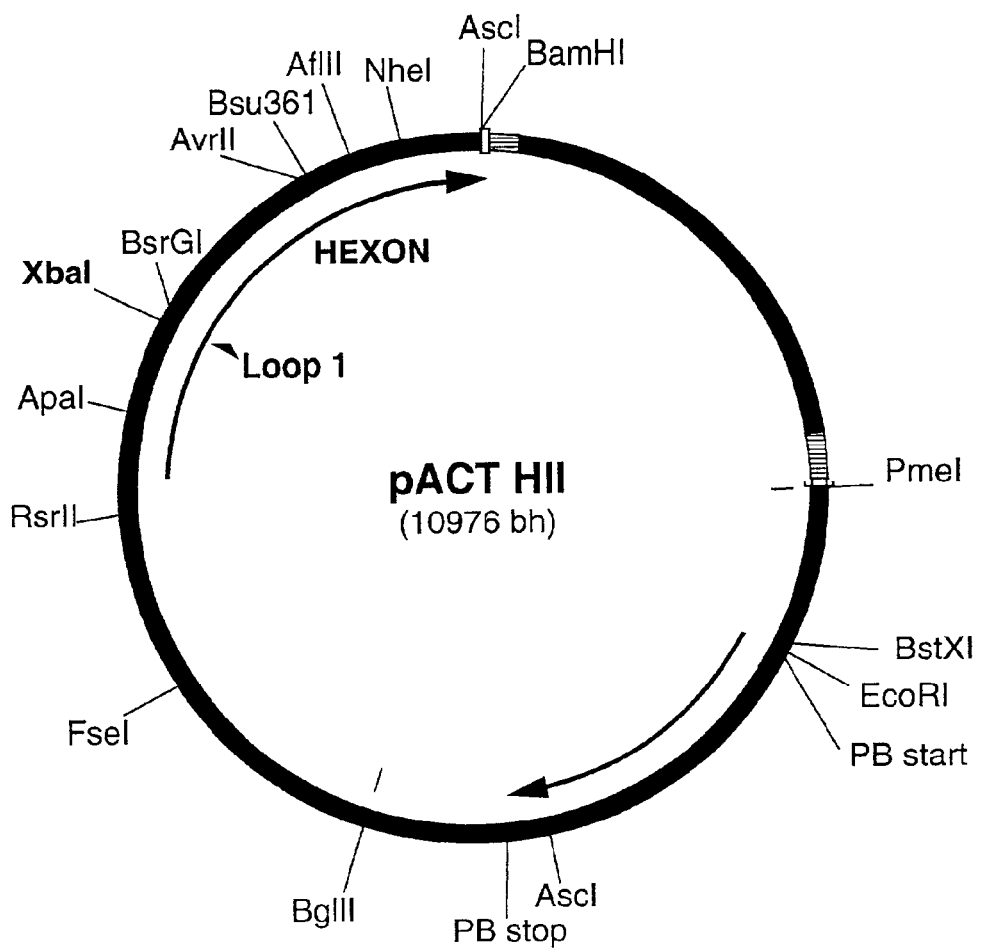
FIG. 22 is a diagram that depicts plasmid pACT H11.

These plasmids can be constructed making use of another transfer plasmid, plasmid pACT H11, depicted in FIG. 22. Plasmid pACT H11 itself is derived from plasmid pACT (comprising from 13259–21561 of the Ad5 genome), which contains the majority of the hexon protein coding sequence (corresponding to about 18842–21700). In particular, pACT H11 can be constructed by incorporating an XbaI site into the loop 1 region of the Ad5 hexon protein. Similar techniques can be used to incorporate an XbaI site, or any other convenient restriction site, into either the loop 1 or the loop 2 region, or into another exposed loop of the hexon protein. Sense and antisense primers can be used to amplify the loop 1 region from Ad5 DNA by PCR, and at the same time introduce a mutation which results in a unique mutated XbaI site in the loop 1 region.

In particular, the sense primer, GGACAGGGGC-CCTACTTTTAAGCCCTACTCTGGCA [SEQ ID NO:81], containing the naturally occurring unique restriction site ApaI that occurs in pACT, and the antisense primer, ATCT-TCACTGTACAATACCACTTTAGGAGT-CAAGTTATCACCTCTAGATGCGGT CGCCT [SEQ ID NO:82], containing the unique restriction site, BsrGI, can be employed. The PCR product, containing the XbaI site can then be cut with BsrGI and ApaI, and cloned back in to pACT to replace the ApaI to BsrGI fragment. The resultant plasmid, pACT H11, contains a unique XbaI site for the insertion of UTV sequences into loop 1 of the hexon. The presence of the XbaI site in the pACT H11 clone can be verified by restriction digestion using XbaI, which should linearize the plasmid.

Part of the unmutated hexon loop 1 amino acid sequence comprises the sequence TEATGNGDNL [SEQ ID NO:83]. In comparison, the mutated hexon loop 1 amino acid sequence following the wild-type TEA residues in pACT H11 (FIG. 22) comprises the sequence TASRGDNL [SEQ ID NO:40] (i.e., encoded by the nucleic acid sequence ACCGCATCTAGAGGTGATAACTTG [SEQ ID NO:39]).

Figure 23:
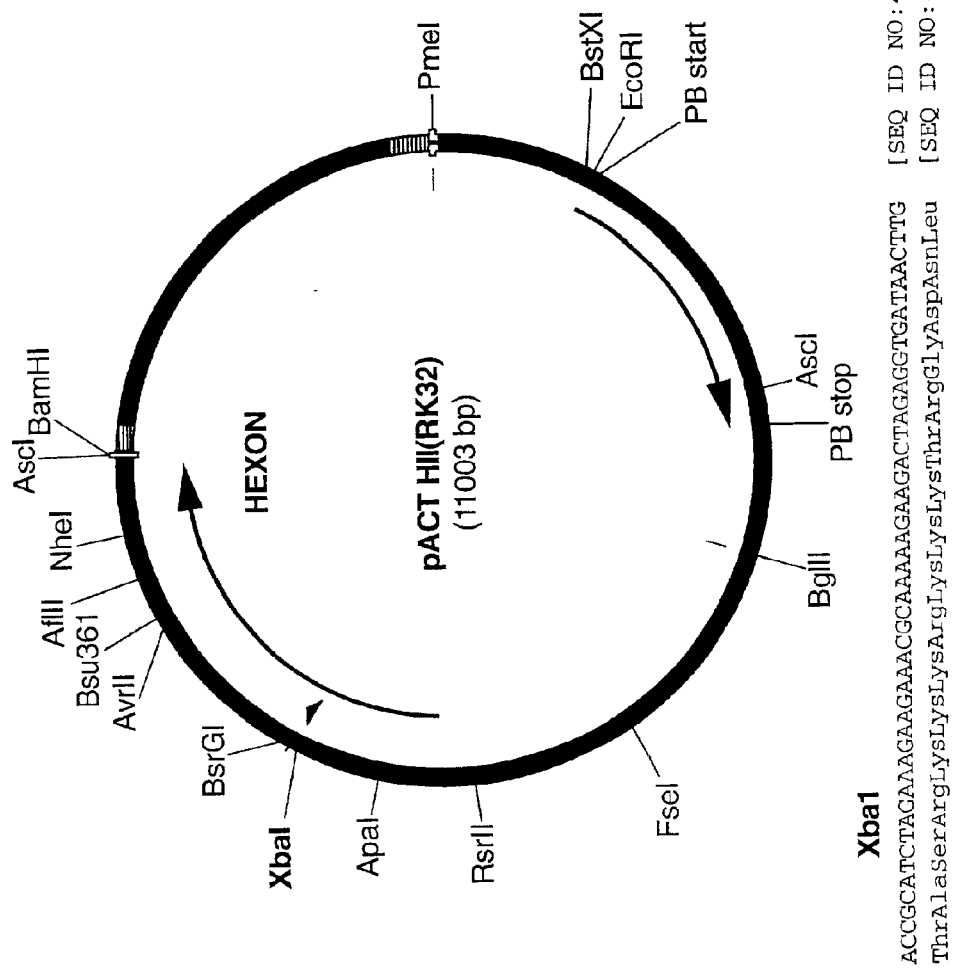
FIG. 23 is a diagram that depicts plasmid pACT H11 (RKKK)₂ (also known as pACT H11 (RKKK2) or pACT H11(RK32)).

The XbaI site of pACT H11 then can be used as a unique site in which to clone universal targeting sequences such as RKKKRKKK [SEQ ID NO:74], for instance, using the overlapping oligonucleotides, RK32s and RK32a. The particular plasmid that results from such manipulations, i.e. pACT H11 (RKKK)$_2$ (or pACT H11 (RK32) or pACT H11 (RKKK2)) is depicted in FIG. 23. This plasmid comprises the sequence:

use of the complementary overlapping oligonucleotides RK33s and RK33a, and directly ligating the PCR product into the XbaI-digested pACT H11 plasmid. Verification of the correctly-oriented clone can be performed by PCR using the RK32 sense primer for the plasmid and an appropriate downstream antisense oligonucleotide primer. The plasmid can be verified to contain the correctly oriented insert by sequencing the DNA sequence in the region of the insert using the downstream antisense primer. Similar approaches can be employed for construction of analogous transfer vectors, particularly the analogous transfer vectors pACT H12 (RKKK)$_2$ and pACT H12 (RKKK)$_3$.

EXAMPLE 11

This example describes the construction of a plasmid having a short-shafted fiber protein. In particular, this example describes the construction of the plasmid, p193 FSF9sK.

Figure 24:
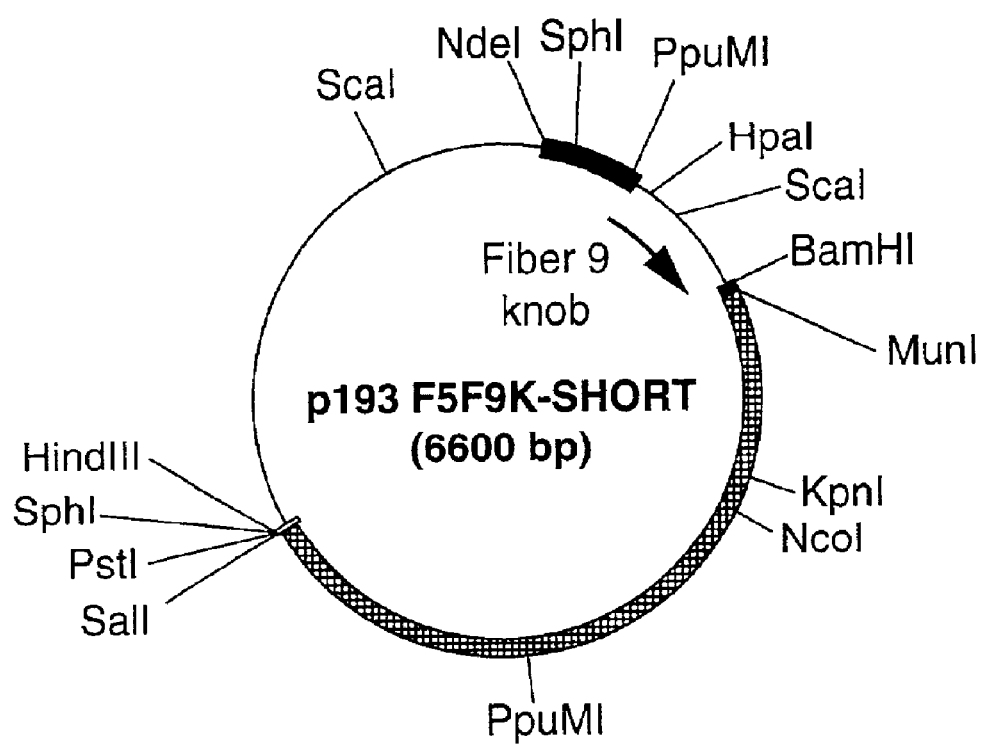
FIG. 24 is a diagram that depicts plasmid p193 F5F9sK (also known as p193 F5F9K-Short).

The plasmid p193 F5F9sK (also known as p193 F5F9K-Short) is depicted in FIG. 24. This vector encodes a chimeric fiber protein wherein approximately two thirds of the Ad5 fiber shaft is deleted and the Ad5 fiber knob is replaced with the Ad9 fiber knob.

The plasmid p193F5F9K-short was constructed from p193NS (F5*). The oligonucleotide primers GGACTAG-TAG CATTTAATAA AAAAGAAGAT AAGCGC [SEQ ID NO:84] and CCGGATCCTC ATTCTTGGGC GATATAGG [SEQ ID NO:85] were used to amplify the Ad9 sequence encoding the last shaft repeat and knob from the fiber gene. The PCR product was then purified, using standard techniques, and digested with the restriction enzymes NheI and BamHI, which allowed cloning of the PCR product into the NheI/BamHI region of the p193NS (F5*) transfer plasmid. The resultant short-shafted fiber protein can be employed in construction of adenoviral vectors, as described below. Furthermore, any one or more of the aforementioned UTV or UTV-like sequences can be incorporated into the short-shafted fiber, and the resultant fiber can be employed for cell delivery.

EXAMPLE 12

This example describes the construction of plasmids containing UTV or UTV-like sequences in an extended structure, particularly in hexon and/or penton base protein, so as to result in lengthened hexon and/or penton base proteins that accordingly are better able to contact cells and participate in cell targeting. The resultant chimeric proteins are "spiked" in the sense that they comprise an insertion of a normative amino acid sequence that will jut out from the virus surface.

```
ACC GCA TCT AGA AAG AAG AAA CGC AAA AAG AAG ACT AGA    [SEQ ID NO:41]

Thr Ala Ser Arg Lys Lys Lys Arg Lys Lys Lys Thr Arg    [SEQ ID NO:42]

GGT GAT AAC TTG

Gly Asp Asn Leu.
```

Other UTV or UTV-like sequences also can be cloned in the loop 1 region of the hexon protein, and/or into the loop 2 region of the hexon protein. For instance, a similar approach can be used to mutate the sequence encoding the hexon loop 2 to make plasmid pACT H12 (not shown) that contains a unique restriction site (such as a XbaI site) into which further UTV sequences can be cloned.

Also, plasmid pACT H11 (RKKK)$_3$ (or pACT H11 (RKKK3) or pACT H11 (RK33)) can be constructed making The primers 1 alpha(s), GGGCTGCAGGCGGCCGCA-GAAGCTGAAGAGGCAGCCACACGGGCTGAGGAGA A [SEQ ID NO:86], and 1 alpha(a), GGGGTGCACACA-GCTTCGGCCTTAGCGTTAGCCTGTTTCTTCTGAGG-CTTCTCGACCT [SEQ ID NO:87], can be used to amplify the region of the penton gene encoding the 32 amino acid α-helical domain that follows the RGD sequence. This 32 amino acid sequence comprises the sequence ATRAEE-DRAEAEAAAEAAAPAAQPEVEKPQKK [SEQ ID NO:88]. The primers used also can encode an additional α-helical sequence on either end, such that, for instance, the final amplified DNA sequence encodes the sequence:

```
CTG CAG GCG GCC GCA GAA GCT GAA GAG GCA GCC ACA CGG GCT GAG [SEQ ID NO:89]

Leu Gln Ala Ala Ala Glu Ala Glu Glu Ala Ala Thr Arg Ala Glu [SEQ ID NO:90]

GAG AAG CGC GCT GAG GCC GAA GCA GCG GCC GAA GCT GCC GCC CCC

Glu Lys Arg Ala Glu Ala Glu Ala Ala Ala Glu Ala Ala Ala Pro

GCT GCG CAA CCC GAC GTC GAG AAG CCT CAG AAG AAA CAG GCT AAC

Ala Ala Gln Pro Glu Val Glu Lys Pro Gln Lys Lys Gln Ala Asn

GCT AAG GCC GAA GCT GTG CAG GCG GCC GCA GAA GCT GAA GAG GCA

Ala Lys Ala Glu Ala Val Gln Ala Ala Ala Glu Ala Glu Glu Ala

GCC ACA CGG GCT GAG GAG AAG CGC GCT GAG GCC GAA GCA GCG GCC

Ala Thr Arg Ala Glu Glu Lys Arg Ala Glu Ala Glu Ala Ala Ala

GAA GCT GCC GCC CCC GCT GCG CAA CCC GAG GTC GAG AAG CCT CAG

Glu Ala Ala Ala Pro Ala Ala Gln Pro Glu Val Glu Lys Pro Gln

AAG AAA CAG GCT AAC GCT AAG GCC GAA GCT GTG CAC

Lys Lys Gln Ala Asn Ala Lys Ala Glu Ala Val His
``` where the emboldened sequence corresponds to the nonpenton sequence encoded by the primers, and the underlined sequence represents the amino acids encoded by the two compatible restriction sites, SfcI and ApaLI. These amino acids also preserve the integrity of an alpha helix according to standard computer programs designed to predict α helix structure.

The PCR product encoding these amino acids can be cut with both SfcI and ApaLI, religated, and then cut again with both enzymes. Ligation of like-site to like-site preserves the site for recutting; however, ligation of the compatible, but unlike sites, destroys the site. Therefore, upon recutting of the ligated product, multiple fragments will be produced which are multiples of the original size of the PCR product. There will be completely recut fragments (approximately 150 bp), approximately 300 bp fragments (having one restriction site destroyed), and approximately 450 bp fragment (having 2 sites destroyed), and so on. The procedure accordingly allows the original sequence encoding 50 amino acids (1 alpha) to be doubled (2alpha), tripled (3alpha), and so on, for cloning large, uninterrupted α-helical regions into a protein to create a larger "spike", or extension of the protein.

Figure 25:
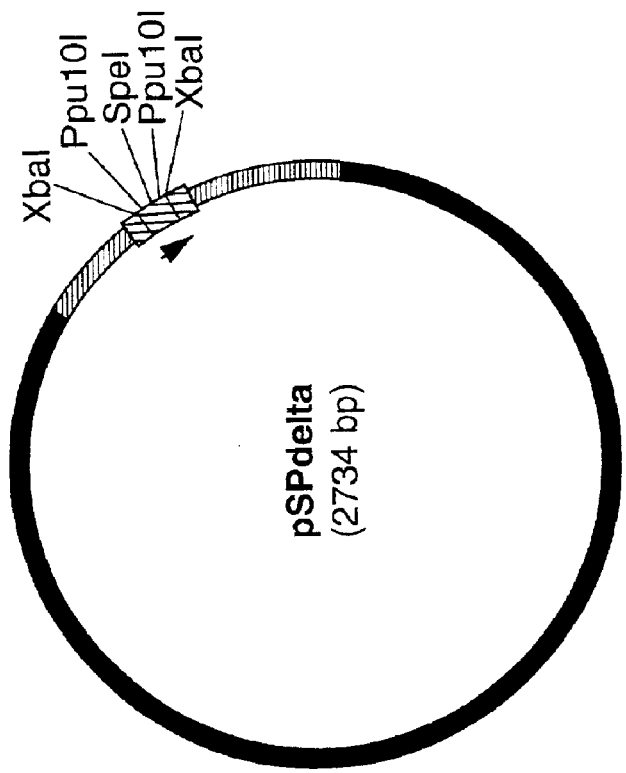
FIG. 25 is a diagram that depicts plasmid pSPdelta.
Figure 26:
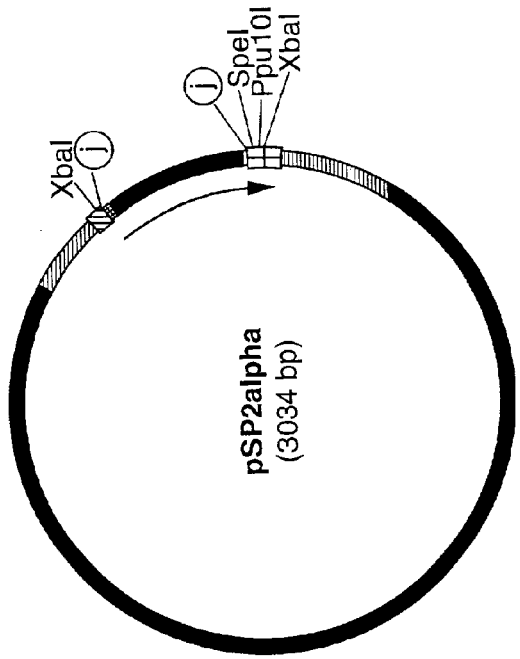
FIG. 26 is a diagram that depicts plasmid pSP2alpha. The "j" indicates destroyed Ppu10I sites in the plasmid.

For instance, the 2alpha double product (i.e., 2alpha2) can be cloned into the first Ppu10I site of the plasmid, pSPdelta (depicted in FIG. 25), to create the plasmid pSP2alpha (depicted in FIG. 26). The plasmid pSPdelta is constructed from the base plasmid pUC19, or any other suitable cloning plasmid. The pSPdelta transfer plasmid can be employed to make further modifications of the penton or hexon protein that allow the UTV sequence (or any other targeting sequence) to be elevated out from the virion surface. This elevation of the targeting sequence in a spiked structure (e.g., a type of "tower") will minimize steric hindrance of the penton and hexon interaction with the cell surface by the fiber protein, and will allow greater access of the chimeric penton and hexon proteins for interacting with the cell surface.

The plasmid pSPdelta contains a unique SpeI cloning site for the incorporation of UTV sequences. The SpeI cloning site is flanked on either side by Ppu10I cloning sites which allow the incorporation of DNA sequences encoding amino acids that will elevate the UTV sequence away from the virion surface. The pSPdelta plasmid was constructed by cloning into the unique XbaI site of pUC19 overlapping oligonucleotides which are designed to insert directly into the XbaI site. In particular, the sense oligonucleotide is: CTAGAGCAGCTATGCATGAAGGGAC-TAGTGGAGAGATGCATGCAGCCT [SEQ ID NO:91]. The antisense, complementary oligonucleotide is: CTA-GAGGCTGCATGCATCTCTCCACTAGTC-CCTTCATGCATAGCTGCT [SEQ ID NO:92]. The oligonucleotides are mixed in equimolar ratios and cloned into the XbaI site of pUC19. The presence of the correct insert can be confirmed by sequencing across the region of the insert, and by cutting the plasmid with Ppu10I. The XbaI sites on either side of the insert allow the convenient removal of this section in later clones.

Figure 27:
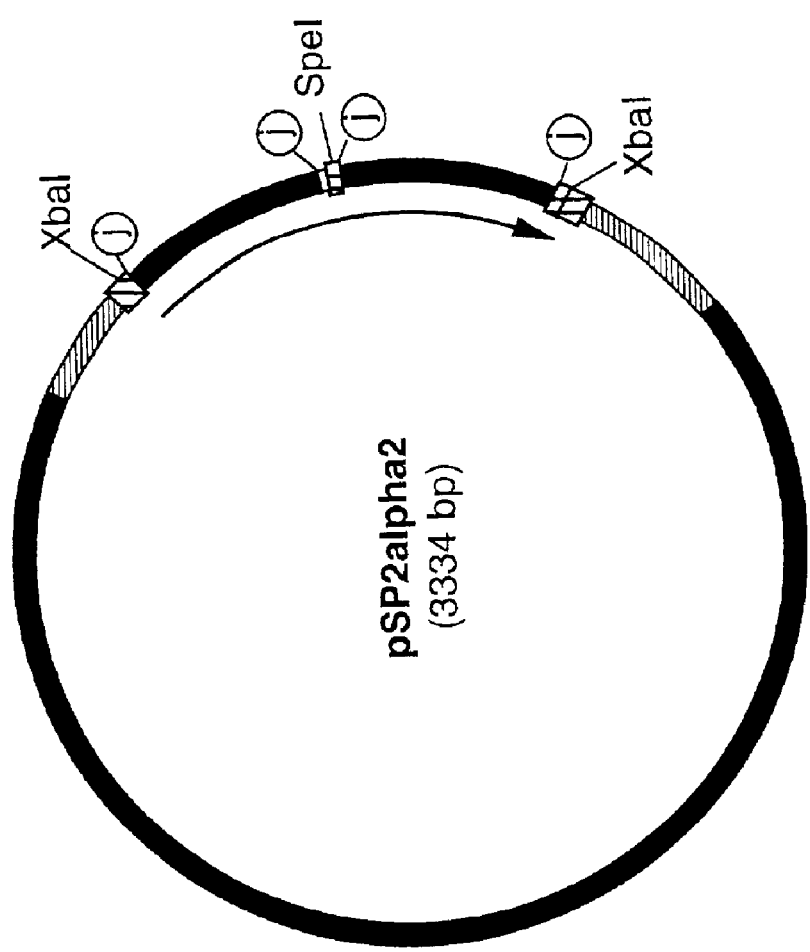
FIG. 27 is a diagram that depicts plasmid pSP2alpha2. The "j" indicates destroyed Ppu10I sites in the plasmid.

Because there are two Ppu10I sites in pSPdelta, the plasmid can be partially restricted upon digestion with Ppu10I so that only a single site is cut. Ligation of the PCR product comprising the ApaLI and SfcI sites into the compatible Ppu10I site will destroy the first Ppu10I site in the plasmid and also destroy the ApaLI and SfcI sites. These destroyed sites are represented in FIG. 26 (showing the pSP2alpha2 plasmid) by a "j". A second doublet product then can be cloned into the remaining Ppu10I site of the pSP2alpha plasmid to produce the plasmid pSP2alpha2 depicted in FIG. 27, which contains an SpeI site for insertion cloning of a UTV sequence, or other similar targeting sequence. Computer analysis of the secondary structure of the anticipated 2alpha2 protein confirms that it will be a complete α helix except for in the region of the SpeI cloning site.

Thus whereas pSPdelta comprises the sequence:
TCT AGA GCA GCT ATG CAT GAA GGG ACT AGT GGA GAC ATG CAT GCA [SEQ ID NO:43]

Ser Arg Ala Ala Met His Glu Gly Thr Ser Gly Glu Met His Ala [SEQ ID NO:44]

GCC TCT AGA

Ala Ser Arg, pSP2alpha comprises the sequence:
TCT AGA GCA GCT ATG CAG GCG GCC GCA GAA GCT GAA GAG GCA [SEQ ID NO:45]

Ser Arg Ala Ala Met Gln Ala Ala Ala Glu Ala Glu Glu Ala [SEQ ID NO:46]

GCC ACA CGG GCT GAG GAG AAG CGC GCT GAG GCC GAA GCA GCG

Ala Thr Arg Ala Glu Glu Lys Arg Ala Glu Ala Glu Ala Ala

GCC GAA GCT GCC GCC CCC GCT GCG CAA CCC GAG GTC GAG AAG

Ala Glu Ala Ala Ala Pro Ala Ala Gln Pro Glu Val Glu Lys

CCT CAG AAG AAA CAG GCT AAC GCT AAG GCC GAA GCT GTG CAG

Pro Gln Lys Lys Gln Ala Asn Ala Lys Ala Glu Ala Val Gln

GCG GCC GCA GAA GCT GAA GAG GCA GCC ACA CGG CCT GAG GAG

Ala Ala Ala Glu Ala Glu Glu Ala Ala Thr Arg Ala Glu Glu

AAG CGC GCT GAG GCC GAA GCA GCG GCC GAA GCT GCC GCC CCC

Lys Arg Ala Glu Ala Glu Ala Ala Ala Glu Ala Ala Ala Pro

GCT GCG CAA CCC GAG GTC GAG AAG CCT GAG AAG AAA CAG GCT

Ala Ala Gln Pro Glu Val Glu Lys Pro Gln Lys Lys GLn Ala

AAC GCT AAG GCC GAA GCT GTG CAT GAA GGG ACT AGT GGA GAG

Asn Ala Lys Ala Glu Ala Val His Glu Gly Thr Ser Gly Glu

ATG CAT GCA GCC TCT AGA

Met His Ala Ala Ser Arg, and pSP2alpha2 comprises the sequence:
TCT AGA GCA GCT ATG CAG GCG GCC GCA GAA GCT GAA GAG GCA GCC [SEQ ID NO:47]

Ser Arg Ala Ala Met Gln Ala Ala Ala Glu Ala Glu Glu Ala Ala [SEQ ID NO:48]

ACA CGG GCT GAG GAG AAG CGC GCT GAG GCC GAA GCA GCG GCC GAA

Thr Arg Ala Glu Glu Lys Arg Ala Glu Ala Glu Ala Ala Ala Glu

GCT GCC GCC CCC GCT GCC CAA CCC GAG GTC GAG AAG CCT CAG AAG

Ala Ala Ala Pro Ala Ala Gln Pro Glu Val Glu Lys Pro Gln Lys

AAA CAG GCT AAC GCT AAG GCC GAA GCT GTG CAG GCG GCC GCA GAA

Lys Gln Ala Asn Ala Lys Ala Glu Ala Val Gln Ala Ala Ala Glu

GCT GAA GAG GCA GCC ACA CGG GCT GAG GAG AAG CGC GCT GAG GCC

Ala Glu Glu Ala Ala Thr Arg Ala Glu Glu Lys Arg Ala Glu Ala

GAA GCA GCG GCC GAA GCT GCC GCC CCC GCT GCG CAA CCC GAG GTC

Glu Ala Ala Ala Glu Ala Ala Ala Pro Ala Ala Gln Pro Glu Val

GAG AAG CCT CAG AAG AAA CAG GCT AAC GCT AAG GCC GAA GCT GTG

Glu Lys Pro Gln Lys Lys Gln Ala Asn Ala Lys Ala Glu Ala Val

CAT GAA GGG ACT AGT GGA GAG ATG CAG GCG GCC GCA GAA GCT GAA

His Glu Gly Thr Ser Gly Glu Met Gln Ala Ala Ala Glu Ala Glu

GAG GCA GCC ACA CGG GCT GAG GAG AAG CGC GCT GAG GCC GAA GCA

```
-continued

Glu Ala Ala Thr Arg Ala Glu Glu Lys Arg Ala Glu Ala Glu Ala
GCG GCC GAA GCT GCC GCC CCC GCT GCG CAA CCC GAG GTC GAG AAG
Ala Ala Glu Ala Ala Ala Pro Ala Ala Gln Pro Glu Val Glu Lys
CCT CAG AAG AAA CAG GCT AAC GCT AAG GCC GAA GCT GTG CAG GCG
Pro Gln Lys Lys Gln Ala Asn Ala Lys Ala Glu Ala Val Gln Ala
GCC GCA GAA GCT GAA GAG GCA GCC ACA CGG GCT GAC GAG AAG CGC
Ala Ala Glu Ala Glu Glu Ala Ala Thr Arg Ala Glu Glu Lys Arg
GCT GAG GCC GAA GCA GCG GCC GAA GCT GCC GCC CCC GCT GCG CAA
Ala Clu Ala Glu Ala Ala Ala Glu Ala Ala Ala Pro Ala Ala Gln
CCC GAG GTC GAG AAG CCT CAG AAG AAA CAC GCT AAC GCT AAG GCC
Pro Glu Val Clu Lys Pro Gln Lys Lys Gln Ala Asn Ala Lys Ala
GAA GCT GTG CAT GCA GCC TCT AGA
Glu Ala Val His Ala Ala Ser Arg.
```

Targeting sequences such as UTV or UTV-like sequences can be cloned into the SpeI site of the plasmid pSP2alpha2. In particular, the RK32s and RK32a overlapping oligonucleotides can be cloned into the SpeI site to create pSP2alpha2 (RKKK)₂ (or, pSP2alpha2 (RK32) or pSPSalpha2 (RKKK2)). The plasmid pSP2alpha2 (RKKK)₃ (or, pSP2alpha2 (RK33) or pSPSalpha2 (RKKK3)) can be similarly constructed. Alternately, the entire 2alpha2 α-helical domain can be removed from the plasmid by restriction with XbaI and cloned into the compatible SpeI site of pACT (ΔRGD) to create pACT 2alpha2 (RKKK)₂ (which also can be called pACT 2alpha2 (RKKK2) or pACT 2alpha2 (RK32)). Similar techniques can be employed to produce pACT 2alpha2 (RKKK)₃ (which also can be called pACT 2alpha2 (RKKK3) or pACT 2alpha2 (RK33)).

Similarly, chimeric hexon proteins that are spiked (i.e., comprise sequences resulting in their extension) can be constructed by cloning the 2alpha2 α-helical domain into the XbaI site of pACT H11 to create pACT H11 2alpha2 (RKKK)₂ (which also can be called pACT H11 2alpha2 (RKKK2) or pACT H11 2alpha2 (RK32)). Similar techniques can be employed to produce pACT H12 2alpha2 (RKKK)₂ (which also can be called pACT H12 2alpha2 (RKKK2) or pACT H12 2alpha2 (RK32)).

EXAMPLE 13

This example describes the construction of further adenoviral vectors, in addition to those previously described, which contain UTV or UTV-like sequences in the adenoviral fiber protein.

Construction of adenovirus vectors containing UTV modifications in the fiber can be accomplished in multiple ways by those skilled in the art. One method to create the UTV fiber vectors from plasmids described above is to first linearize the plasmid DNA with SalI and then transfect this DNA into a 293 packaging cell line that was infected just prior to transfection with an E4-deleted adenovirus. E4-deleted adenovirus vectors are incapable of replicating in cell lines such as the 293 cell line, which only provide the adenovirus E1 regions in trans. Recombination of the plasmids which contain the modified fiber gene and the E4 regions with the E4-deleted DNA results in a replication-competent, E4-containing vector which carries the modified fiber gene.

Accordingly, the plasmids p193NS (F5*) pGS(K7), pBSS 75–100 pGS(null), pBSS 75–100 pGS(RKKK)₂, pBSS 75–100 pGS(RKKK)₃, pBSS 75–100 pGS(tat), p193NS F5F2K(RK32), and p193 F5F9sK were each linearized with SalI and transfected into 293 cells infected 1 hour prior with either the E4-deleted adenovirus vector, GV11 A.Z (which carries the LacZ gene under the control of a cytomegalovirus (CMV) promoter), or GV11A.S (which carries a secretory alkaline phosphatase gene under the control of a CMV promoter). The resultant adenovirus vectors, AdZ.F(pK7), AdZ.F(pGS), AdZ.F(RKKK)₂ (also known as AdZ.F (RKKK2) or AdZ.F(RK32)), AdZ.F(RKKK)₃ (also known as AdZ.F(RKKK3) or AdZ.F(RK33)), AdZ.F(tat), AdZ.F5F2K(RKKK)₂ (also known as AdZ.F5F2K(RKKK2) or AdZ.F5F2K(RK32)), and AdZ.F5F9sK (also known as AdZ.F5F9K-Short) were obtained and were purified through two successive rounds of plaquing on 293 cells.

All the vectors were verified to contain the correct sequence through PCR across the region of the insert, and by restriction analysis of viral DNA obtained from vector-infected 293 cells by Hirt extraction. Western analysis (as previously described) also can be employed to examine protein size, if so desired. Western analysis of fiber protein from vector particles and/or vector-infected cell lysates electrophoresed on a polyacryamide gel should show a corresponding shift in the mobility of the fiber protein compared to unmodified fiber protein that is consistent with the presence of additional amino acid sequences. For instance, Western analysis of AdZ.F(pK7) particles verified that its fiber protein is shifted up compared to that of the AdZ vector comprising unmodified fiber, consistent with the presence of additional amino acids in the AdZ.F(pK7) fiber protein.

Other plasmid maps depicted herein similarly can be made into adenoviral vectors by utilizing the same procedure outlined above (or minor variations thereof).

EXAMPLE 14

This example describes the construction of adenoviral vectors which contain UTV or UTV-like sequences in the adenoviral penton base protein.

The method of making an adenoviral vector comprising a chimeric penton base protein is described, for instance, in Wickham et al., *J. Virol.*, 70, 6831–6838 (1996). A pACT vector described above containing the chimeric penton base protein (e.g., transfer plasmids pACT 2alpha2 (RKKK)$_2$, pACT H12 2alpha2 (RKKK)$_2$, and pACT (ΔRGD)) can be digested, for instance, with BamHI, to linearize the plasmid. Ad5 DNA can be digested with the restriction endonuclease XmnI, which cuts wild-type Ad5 at positions 14561 and 15710 within the Ad5 genome. The two larger fragments are purified away from the smaller 1 kb piece then transfected along with the linearized plasmid into the appropriate cell line (e.g., a 293 cell line) to produce recombinant virus.

Adenoviral vectors produced in this fashion are purified from potentially-contaminating unmodified vectors through two successive rounds of plaque purification on 293 cells. The resultant vectors are then verified to contain the correct sequence in the penton base region through restriction analysis of viral DNA obtained following Hirt extraction of vector-infected 293 cells. Sequencing of PCR products generated by amplifying the region of the insert from the viral DNA can also be used to verify the presence of the insert. Western analysis of the chimeric penton base electrophoresed on a polyacrylamide gel should show a corresponding shift in the mobility of the penton base compared to unmodified penton base that is consistent with the presence of additional amino acid sequences in the chimeric protein.

EXAMPLE 15

This example describes the construction of adenoviral vectors containing UTV or UTV-like sequences in the hexon protein.

To construct the virus AdZ.H(RKKK)$_2$, left and right vector arms are prepared that contain DNA sequences which overlap and will recombine on either side of the PmeI to BamHI pACT H11 (RK32) sequence to create an intact AdZ.H (RK32) genome. To construct the left arm, purified Ad5 DNA is restriction digested with AgeI, which cuts Ad5 at positions 14499, 15283, 19017, 23063, 23656, 23411, and 31102. The 0–14499 fragment then can be employed as the left arm and purified from the other fragments by gel electrophoresis. The right arm can be prepared by digesting Ad5 DNA with DrdI. DrdI cuts Ad5 at positions 5458, 7039, 14004, 15593, 17257, and 21023. The 21023–35938 bp fragment then can be used as the right arm and purified from the other fragments by gel electrophoresis. These two fragments are then transfected with the PmeI/BamHI fragment from pACT H11(RK32) into 293 cells. PmeI cuts at position 13258 in Ad5, and BamHI cuts at position 21562 in Ad5. Similar techniques can be employed to produce AdZ.H (RKKK)$_3$.

EXAMPLE 16

This example describes the construction of vectors containing a short-shafted fiber protein.

The method described herein for construction of an adenovirus from the transfer plasmid p 193 FSF9Kshort can similarly be employed for the construction of other adenoviral vectors from other short-shafted fibers. Namely, the transfer plasmid p 193 F5F9Kshort, which contains the essential E4 region of adenovirus, was cut with SalI and transfected into 293 cells, which had been infected one hour earlier with the adenoviral vector AdSE.E4Gus. AdSE.E4Gus lacks the E4 region of the adenoviral genome, and cannot replicate in 293 cells in the absence of complementation for the E4 genes. Thus, only when the AdSE.E4Gus DNA recombines with the p193 F5F9K short plasmid DNA to obtain the E4 genes is the vector able to replicate in 293 cells. During this recombination event, the newly formed vector also acquires the mutated fiber protein coding sequences encoded by the plasmids. Viable recombinant E4$^+$ adenovirus containing the F5F9Kshort fiber chimera were then isolated by plaquing the transfected cell lysates 5 days after transfection. The resultant vector AdSE.F5F9Kshort was isolated and purified by standard virological techniques involving two successive rounds of plaquing on 293 cells. The vector was verified to contain the correct insert by PCR and restriction analysis of viral DNA. Oligonucleotide primers, which prime on either side of the fiber gene, confirmed that the PCR product was of the correct size for that encoded by a shortened chimeric fiber gene. Restriction analysis of the vector DNA showed that the new vector contained the correct restriction sites that are unique to the Ad9 fiber knob.

EXAMPLE 17

This example describes the construction of adenoviral vectors that contain short-shafted fiber proteins and chimeric penton base proteins incorporating UTV or UTV-like sequences.

For this construction, AdS.F9sK viral DNA can be digested with XmnI, as described above. The plasmid pACTH11 (RK32)is then cut with the restriction enzymes PmeI and BamHI. The restriction digested viral and plasmid DNAs are purified and transfected into 293 cells. The resultant vectors are isolated by two successive rounds of plaque purification on 293 cells, and are verified to contain the correct sequence in the penton base region by restriction analysis of viral DNA obtained from vector-infected 293 cells by Hirt extraction.

Sequencing of PCR products generated by amplifying the region of the insert from the viral DNA also can be used to verify the presence of the insert. Western analysis of the chimeric penton base protein on a polyacrylamide gel should show a corresponding shift in the mobility of the chimeric penton base compared to unmodified penton base that is consistent with the presence of additional nonnative amino acid sequences (and absence of native amino acid sequences).

Other plasmids for which maps are presented herein and which were not made into an adenoviral vector can be made by utilizing the same or a slightly modified version of the procedure outlined above. In particular, the short-shafted fiber protein can be incorporated into an adenovirus having a "spiked" chimeric penton base protein that furthermore optionally can incorporate a UTV or UTV-like sequence.

EXAMPLE 18

This example describes the construction of adenoviral vectors that contain short-shafted fiber proteins and chimeric hexon proteins incorporating UTV or UTV-like sequences.

Viral DNA can be isolated from a short-shafted vector such as AdZ.F9sK and cut with the restriction enzymes described above for making vectors comprising UTV-containing chimeric hexon proteins. All other steps are the same as described, for instance, in Example 17. The resultant vector should contain the short-shafted fiber protein and the chimeric hexon protein incorporating UTV or UTV-like sequences. Moreover, this approach can be employed with a variety of transfer plasmids comprising different chimeric hexon proteins. In particular, the short-shafted fiber protein can be incorporated into an adenovirus having a "spiked" chimeric hexon protein that furthermore optionally can incorporate a UTV or UTV-like sequence.

EXAMPLE 19

This example describes an evaluation of vectors, particularly adenoviral vectors, according to the invention, which comprise UTV or UTV-like sequences.

Figure 28:
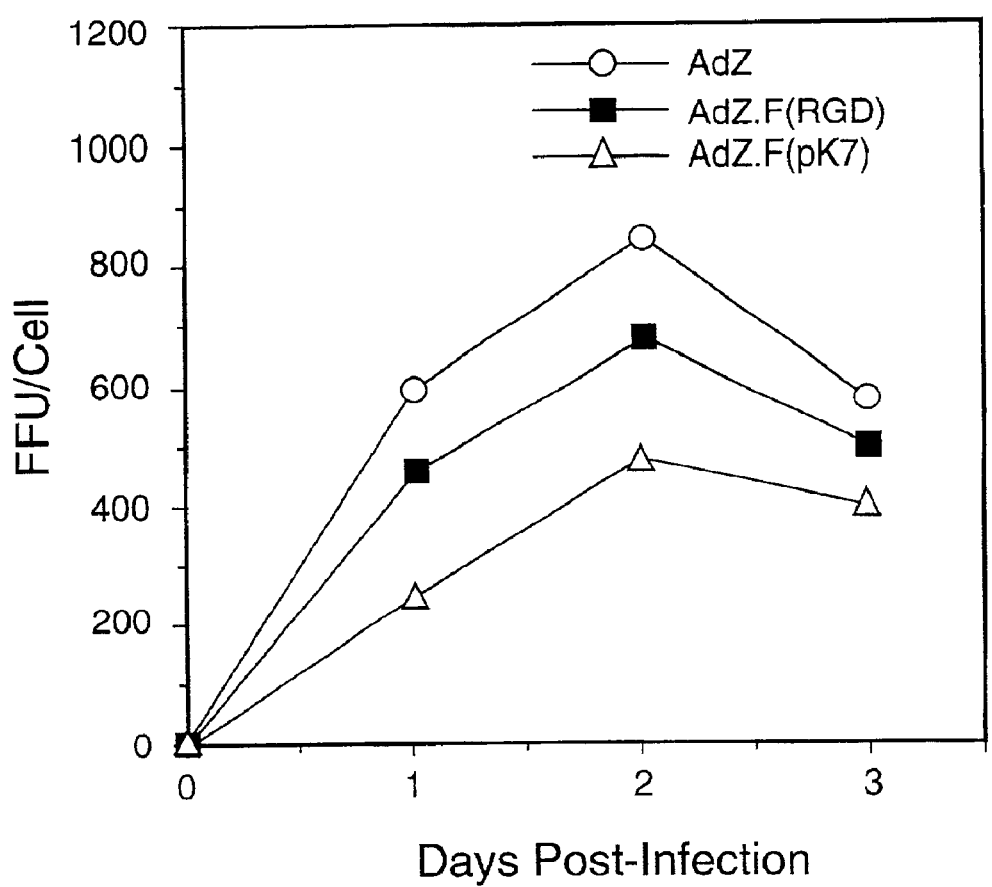
FIG. 28 is a graph of days post-infection versus FFU/cell for 293 cells infected with Ad5 (open circles). AdZ.F(RGD) (closed squares), or AdZ.F(pK7) (open triangles).

For instance, to confirm that the addition of UTV or UTV-like sequences has no effect on virus assembly, the virus growth kinetics of the vectors can be assessed. As representative of a UTV-sequence containing plasmid, the growth behavior of pAd.F(pK7) was monitored and compared to that of wild-type adenovirus (Ad5), as well as the adenoviral vector AdZ.F(RGD), which contains an insertion of a RGD peptide motif present in the sequence SACD-CRGDCFCGTS [SEQ ID NO:93]. For these studies, 293 cells were infected at a multiplicity of infection of 5 active virus particles/cell with either Ad5, AdZ.F(RGD) or AdZ.F (pK7), and the number of infectious particles (fluorescent focus units (FFU)) produced per cell was determined following the harvesting of the cells at 1, 2, and 3 days post infection. The titers of AdZ.F(RGD) or AdZ.F(pK7) were somewhat lower, but not dramatically different than the titer of Ad5. As can be seen in FIG. 28, the peak titers of AdZ.F(RGD) and AdZ.F(pK7) were 80% and 56%, respectively, that of Ad5. These results confirm that the growth kinetics of the two vectors are not substantially affected by the addition of sequences, particularly a UTV or UTV-like sequence, onto the end of the fiber protein. The results also suggest that further vectors comprising UTV or UTV-like sequences will not exhibit aberrant growth behaviour.

Furthermore, vectors containing UTV or UTV-like sequences can be evaluated for their ability to bind to cells or deliver genes to be inhibited by negatively-charged molecules (e.g., heparin, heparan sulfate, chondroitan sulfate, etc.), soluble adenoviral coat proteins, or by pretreatment of cells with agents (e.g., chondroitinase, heparinase, sialidase, etc.) that cleave such negatively-charged moieties (see, e.g., Wickham et al., *Nature Biotechnology*, 14, 1570–1573 (1996), as well as the preceding Examples). Soluble fiber protein will not inhibit the majority of the binding of a UTV vector to a cell (Wickham et al. (1996), supra). These results suggest that the incorporation of UTV or UTV-like sequences into penton, hexon or fiber will not impair the ability of a recombinant adenovirus containing the chimeric coat protein to effect gene delivery.

Also, studies of infection in vivo, or in vitro transfections done in the presence of whole blood, can be employed to confirm that the UTV vectors of the present invention are not limited for systemic delivery due to saturation of the polycations on the recombinant adenoviruses with polyanions in the blood. In the event that such binding impedes the capability of a particular virus for target cell transduction, the virus can be administered in a higher dose, preferably with provision being made to reduce any immune response associated with such a higher dose (e.g., administration of another serotype of adenoviral vector, or techniques described in PCT International Application WO 96/12406; Mastrangeli et al., *Human Gene Therapy*, 7, 79–87 (1996)).

All of the references cited herein, including patents, patent applications, and publications, are hereby incorporated in their entireties by reference to the same extent as if each reference were set forth in its entirety herein.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

---

What is claimed is:

1. A recombinant adenovirus comprising a penton base protein and a fiber protein, wherein the penton base protein and fiber protein lack native binding to a cell surface binding site.

2. The recombinant adenovirus of claim 1, wherein the penton base protein is unable to bind an $\alpha_v$ integrin receptor.

3. The recombinant adenovirus of claim 2, wherein the penton base protein lacks a native RGD sequence.

4. The recombinant adenovirus of claim 1, wherein the fiber protein trimerizes.

5. The recombinant adenovirus of claim 1, wherein the fiber protein lacks the fiber knob.

6. The recombinant adenovirus of claim 5, wherein the fiber protein trimerizes.

7. A recombinant adenovirus comprising (a) a penton base protein that lacks native binding to a cell surface binding site and (b) a nonnative amino acid sequence that binds a cell surface binding site.

8. The recombinant adenovirus of claim 7, wherein the penton base protein is unable to bind an $\alpha_v$ integrin receptor.

9. The recombinant adenovirus of claim 7, wherein the penton base protein lacks a native RGD sequence.

10. The recombinant adenovirus of claim 7, wherein the adenovirus further comprises a fiber protein lacking native binding.

11. The recombinant adenovirus of claim 10, wherein the fiber protein trimerizes.

12. The recombinant adenovirus of claim 10, wherein the nonnative amino acid sequence is inserted into the fiber protein or in place of at least a portion of the fiber protein.

13. The recombinant adenovirus of claim 12, wherein the nonnative amino acid sequence is inserted into a knob region of the fiber protein or in place of at least a portion of a knob region of the fiber protein.

14. The recombinant adenovirus of claim 13, wherein the fiber protein trimerizes.

15. The recombinant adenovirus of claim 13, wherein the nonnative amino acid sequence is inserted into an exposed loop of the adenovirus fiber knob or in place of at least a portion of an exposed loop of the adenovirus fiber knob.

* * * * *